US012252546B2

(12) United States Patent
Poirier et al.

(10) Patent No.: US 12,252,546 B2
(45) Date of Patent: Mar. 18, 2025

(54) ANTI-SIRPa ANTIBODIES AND THEIR THERAPEUTIC APPLICATIONS

(71) Applicant: OSE IMMUNOTHERAPEUTICS, Nantes (FR)

(72) Inventors: Nicolas Poirier, Treillières (FR); Caroline Mary, Sainte-Pazanne (FR); Bernard Vanhove, Rezé (FR); Vanessa Gauttier, Rezé (FR); Virginie Thepenier, Port-Saint-Père (FR); Sabrina Pengam, Nantes (FR)

(73) Assignee: OSE IMMUNOTHERAPEUTICS, Nantes (FR)

( * ) Notice: Subject to any disclaimer, the term of this patent is extended or adjusted under 35 U.S.C. 154(b) by 0 days.

(21) Appl. No.: 17/681,219

(22) Filed: Feb. 25, 2022

(65) Prior Publication Data

US 2022/0281991 A1 Sep. 8, 2022

Related U.S. Application Data

(62) Division of application No. 16/093,062, filed as application No. PCT/EP2017/059071 on Apr. 14, 2017, now Pat. No. 11,279,766.

(60) Provisional application No. 62/322,707, filed on Apr. 14, 2016.

(30) Foreign Application Priority Data

Feb. 17, 2017 (EP) .................... 17305182

(51) Int. Cl.
C12N 15/09 (2006.01)
A61P 35/00 (2006.01)
C07K 16/00 (2006.01)
C07K 16/28 (2006.01)
C12N 5/00 (2006.01)
G01N 33/68 (2006.01)
A61K 39/00 (2006.01)

(52) U.S. Cl.
CPC .......... C07K 16/2896 (2013.01); A61P 35/00 (2018.01); C07K 16/2803 (2013.01); C07K 16/2818 (2013.01); C07K 16/2827 (2013.01); C07K 16/2878 (2013.01); G01N 33/68 (2013.01); A61K 2039/505 (2013.01); A61K 2039/507 (2013.01); C07K 2317/24 (2013.01); C07K 2317/56 (2013.01); C07K 2317/75 (2013.01); C07K 2317/76 (2013.01); C07K 2317/92 (2013.01); C07K 2318/00 (2013.01); C12N 5/00 (2013.01); C12N 15/09 (2013.01); G01N 2333/70596 (2013.01)

(58) Field of Classification Search
None
See application file for complete search history.

(56) References Cited

U.S. PATENT DOCUMENTS

| 2003/0054415 A1 | 3/2003 | Buhring et al. |
| 2010/0215640 A1 | 8/2010 | Clemmons et al. |
| 2010/0233251 A1 | 9/2010 | Von Andrian et al. |
| 2010/0239578 A1 | 9/2010 | Danska et al. |
| 2011/0014119 A1 | 1/2011 | Jaiswal et al. |
| 2012/0039896 A1 | 2/2012 | Clemmons et al. |
| 2012/0070461 A1 | 3/2012 | Singh et al. |
| 2014/0141002 A1 | 5/2014 | Clemmons et al. |
| 2014/0193408 A1* | 7/2014 | Huber .................. A61P 9/10 |
| | | 435/69.6 |
| 2014/0242095 A1 | 8/2014 | Wang et al. |
| 2017/0247464 A1 | 8/2017 | Poirier et al. |
| 2018/0312600 A1 | 11/2018 | Poirier et al. |
| 2021/0040206 A1 | 2/2021 | Poirier et al. |
| 2021/0179728 A1 | 6/2021 | Poirier et al. |

FOREIGN PATENT DOCUMENTS

| CN | 111995682 A | 11/2020 |
| CN | 112010979 A | 12/2020 |
| CN | 112574310 A | 3/2021 |
| EP | 1637598 A1 | 3/2006 |
| WO | 2007005874 A2 | 1/2007 |
| WO | 2009131453 A1 | 10/2009 |
| WO | 2010077634 A1 | 7/2010 |
| WO | 2010130053 A1 | 11/2010 |
| WO | 2012149416 A2 | 11/2012 |
| WO | 2013056352 A1 | 4/2013 |
| WO | 2013079174 A1 | 6/2013 |
| WO | 2013109752 A1 | 7/2013 |
| WO | 2014123580 A1 | 8/2014 |
| WO | 2015048312 A1 | 4/2015 |
| WO | 2015138600 A2 | 9/2015 |
| WO | 2016063233 A1 | 4/2016 |
| WO | 2016205042 A1 | 12/2016 |

(Continued)

OTHER PUBLICATIONS

Wan et al., "Aberrant Regulation of Synovial T Cell Activation by Soluble Costimulatory molecules in Rheumatoid Arthritis", J. Immunol., 2006, pp. 8844-8850, vol. 177.
Wang et al., "Immune Regulation by 4-1BB and 4-1BBL: Complexities and Challenges", Immunol. Rev., 2009, pp. 192-215, vol. 229, No. 1.
Weiskopf et al, "Direct SIRPa Blockade Augments Macrophage Responses to Therapeutic Anticancer Antibodies", Blood Journal, Dec. 2014, vol. 124, No. 21, Abstract.
Willingham et al., "The CD47-Signal Regulatory Protein Alpha (SIRPa) Interaction is a Therapeutic Target for Human Solid Tumors", Proceedings of the National Academy of Sciences, Apr. 2012, pp. 6662-6667, vol. 109, No. 17.

(Continued)

Primary Examiner — Elizabeth C. Kemmerer
Assistant Examiner — Regina M DeBerry
(74) Attorney, Agent, or Firm — Thompson Coburn LLP; William A. Holtz

(57) ABSTRACT

The present invention provides new anti-SIRPa antibodies able to specifically antagonize the interaction between SIRPa and CD47, without affecting the interaction between SIRPg and CD47, and their uses.

23 Claims, 41 Drawing Sheets

Figure 1A:
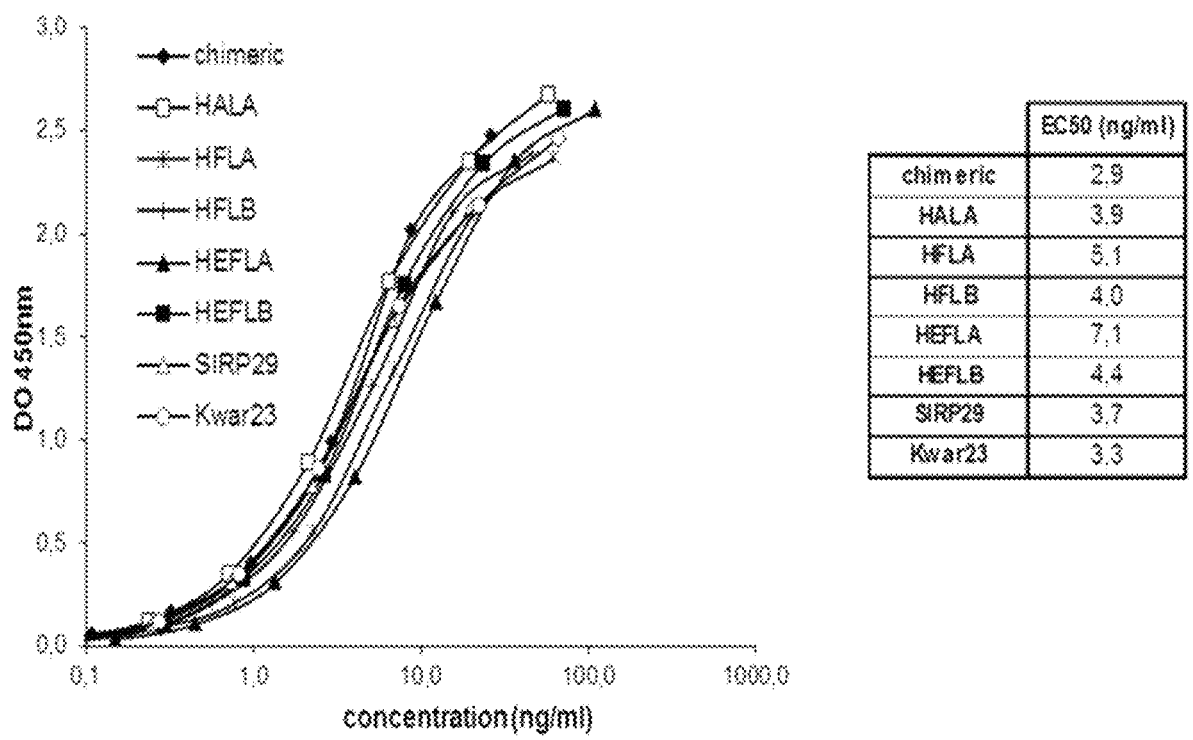

Specification includes a Sequence Listing.

(56) References Cited

FOREIGN PATENT DOCUMENTS

| WO | 2017068164 A1 | 4/2017 |
|---|---|---|
| WO | 2017178653 A2 | 10/2017 |
| WO | 2018057669 A1 | 3/2018 |
| WO | 2018107058 A1 | 6/2018 |
| WO | 2018210793 A2 | 11/2018 |
| WO | 2019023347 A1 | 1/2019 |
| WO | 2019073080 A1 | 4/2019 |
| WO | 2019175218 A1 | 9/2019 |
| WO | 2019183266 A1 | 9/2019 |
| WO | 2019226973 A1 | 11/2019 |
| WO | 2020013170 A1 | 1/2020 |
| WO | 2020033646 A1 | 2/2020 |
| WO | 2020068752 A1 | 4/2020 |
| WO | 2020099653 A1 | 5/2020 |
| WO | 2020102422 A1 | 5/2020 |
| WO | 2020180811 A1 | 9/2020 |
| WO | 2021032078 A1 | 2/2021 |
| WO | 2021185273 A1 | 9/2021 |

OTHER PUBLICATIONS

Willoughby et al., "OX40: Structure and Function—What Questions Remain?", Mol. Immunol., 2017, pp. 13-22, vol. 83.
Yanagita et al., "Anti-SIRP a Antibodies as a Potential New Tool for Cancer Immunotherapy", JCI Insight, Jan. 2017, pp. 1-15, vol. 2, No. 1.
Zak et al., "Structure of the Complex of Human Programmed Death 1, PD-1, and Its Ligand PD-L1", Structure, 2015, pp. 2341-2348, vol. 23, No. 12.
Zhao et al., "CD47-Singal Regulatory Protein—(SIRP) Interactions Form a Barrier for Antibody-Mediated Tumor Cell Destruction", Proceedings of the National Academy of Sciences, Nov. 8, 2011, pp. 18342-18347, vol. 108, No. 45.
Colman, "Effects of Amino Acid Sequence Changes on Antibody-Antigen Interactions", Research in Immunology, 1994, pp. 33-36, vol. 145, No. 1.
International Search Report and Written Opinion for PCT/EP2019/056250 dated Jun. 18, 2019.
International Search Report issued in corresponding international Patent Application No. PCT/IB2015/058124 dated Jan. 19, 2016.
Paul, "Fundamental Immunology", Laboratory of Immunology, National Institute of Allergy and Infectious Diseases, NIH, 1993, Third Edition, Chapter 9, pp. 292-595.
Rudikoff et al., "Single Amino Acid Substitution Altering Antigen-Binding Specificity", Proc. Natl. Acad. Sci. USA, Mar. 1982, pp. 1979-1983, vol. 79.
Written Opinion issued in corresponding International Patent Application No. PCT/IB2015/058124 dated Jan. 19, 2016.
Abe et al., "Blockade of CD47-Signaling Regulatory Protein Alpha Signaling Enhances the Macrophage Phagocytic Activity Against Cancer Cells", Transplantation, Abstract B1139, Jul. 2014. pp. 313, vol. 98, Suppl. 1, World Transplantation Congress.
Alblas et al., "Signal Regulatory Protein Ligation Induces Macrophage Nitric Oxide Production Through JAK/STAT and Phosphatidylinositol 3-Kinase/Racl/NAPDH Oxidase/H2O2-Dependent Pathways", Molecular and Cellular Biology, Aug. 15, 2005, pp. 7181-7192, vol. 25, No. 16.
Ansell, "Targeting Immune Checkpoints in Lymphoma", Current Opinion in Hematology, 2015, pp. 337-342, vol. 22, No. 4.
Barclay et al., "The Interaction Between Signal Regulatory Protein Alpha (SIRPa) and CD47: Structure, Function, and Therapeutic Target", Annual Review of Immunology, 2014, pp. 25-50, vol. 32.
Borch et al., "Reorienting the Immune System in the Treatment of Cancer by Using Anti-PD-1 and Anti-PD-L1 Antibodies", Drug Discovery Today, Sep. 2015, pp. 1127-1134, vol. 20, No. 9.
Brahmer et al., "Safety and Activity of Anti-PD-L1 Antibody in Patients with Advanced Cancer", N. Eng. J. Med., 2012, pp. 2455-2465, vol. 366, No. 26.

Chao et al., "Response: Mechanisms of Targeting CD47-SIRP [Alpha] in Hematologic Malignancies", Blood American Society of Hematology, May 3, 2012, pp. 4334-4335, vol. 119, No. 18.
Crepeau et al., "Challenges and Opportunities in Targeting the CD28/CTLA-4 Pathway in Transplantation and Autoimmunity", Expert Opin. Biol. Ther., 2017, pp. 1001-1012, vol. 17, No. 8.
Gabrilovich et al., "Myeloid-Derived Suppressor Cells as Regulators of the Immune System", Nature Reviews Immunology, Mar. 2009, pp. 162-174, vol. 9, No. 3.
Gauttier et al., "Dual Targeting of Adaptive and Innate Immune Checkpoints Induce Potent Memory Anti-Tumor Response", European Journal of Cancer, Jul. 2016, pp. S216-S217, vol. 61, Supplement 1.
Gilbreth et al., "Crystal Structure of the Human 4-1BB/4-1BBL Complex", J. Biol. Chem., 2018, pp. 9880-9891, vol. 293, No. 25.
Girard et al., "CD80 and CD86 IgC Domains are Important for Quaternary Structure, Receptor Binding and Co-Signaling Function", Immunology Letters, 2014, Article in Press, pp. 1-11.
Hatherly et al., "The Structure of the Macrophage Signal Regulatory Protein (SIRP) Inhibitory Receptor Reveals a Binding Face Reminiscent of That Used by T Cell Receptors", Journal of Biological Chemistry, Mar. 6, 2007, pp. 14567-14575, vol. 282, No. 19.
International Search Report and Written Opinion for PCT/EP2017/059071 dated Jun. 5, 2018.
Ishida et al., "Induced Expression of PD-1, a Novel Member of the immunoglobulin Gene Superfamily, Upon Programmed Cell Death", EMBO J., 1992, pp. 3887-3895, vol. 11, No. 11.
Justice et al., "Using the Mouse to Model Human Disease: Increasing Validity and Reproducibility", Disease, Models & Mechanisms, 2016, pp. 101-103, vol. 9.
Lee et al., "Novel Structural Determinants on SIRP Alpha That Mediate Binding to CD47", Journal of Immunology, Jan. 1, 2007, pp. 7741-7750.
Lin et al., "The PD-1/PD-1L Complex Resembles the Antigen-Binding Fv Domains of Antibodies and T Cell Receptors", PNAS, 2008, pp. 3011-3016, vol. 15, No. 8.
Liu et al., "Functional Elements on SIRP@a IgV Domain Mediate Cell Surface Binding to CD47", Journal of Molecular Bio, Academic Press, Dec. 23, 2006, pp. 680-693, vol. 365, No. 3.
Liu et al., "Signal Regulatory Protein (SIRPalpha), a Cellular Ligand for CD47, Regulates Neutrophil Transmigration," Journal of Biological Chemistry, Mar. 15, 2002, pp. 10028-10036, vol. 277, No. 12.
Makarova-Rusher et al., "The Yin and Yang of Evasion and Immune Activation in HCC", Journal of Hepatology, Jun. 2015, pp. 1420-1429, vol. 62, No. 6.
McCracken et al., "Molecular Pathways: Activating T Cells after Cancer Cell Phagocytosis from Blockade of CD47 "Don't Eat Me" Signals", Clinical Cancer Research, Aug. 2015, pp. 3597-3601, vol. 21, No. 16.
Mosser et al., "Exploring the Full Spectrum of Macrophage Activation", Nature Reviews Immunology, 2008, pp. 958-969, Vo. 8, No. 12.
Nielsen et al., "Alternative Splice Variants of the Human PD-1-Gene", Cell Immunol., 2005, pp. 109-116, vol. 235.
Ochando et al., "Myeloid-derived Suppressor Cells in Transplantation and Cancer", Immunologic Research, Apr. 26, 2012, pp. 275-285, vol. 54, No. 1-3, Humana Press Inc., New York.
Oldenborg et al., "Role of CD47 as a Marker of Self on Red Blood Cells", Science, Jun. 2000, pp. 2051-2054, vol. 288, No. 5473.
Pan et al., "Signal Regulatory Protein [Alpha] is Associated with Tumor-Polarized Macrophages Phenotype Switch and Plays a Pibotal Role in Tumor Progression", Hepatology, Aug. 1, 203, pp. 680-691, vol. 58, No. 2.
Pardoll, "The Blockade of Immune Checkpoints in Cancer Immunotherapy", Nature Reviews Cancer, 2012, pp. 252-264, vol. 12, No. 4.
Peach et al., "Both Extracellular Immunoglobin-Like Domains of CD80 Contains Residues Critical for Binding T-Cell Surface Receptors CTLA-4 and CD28", J. Biol. Chem., 1995, pp. 21181-21187.

(56) References Cited

OTHER PUBLICATIONS

Powles et al., "MPDL3280A (Anti-PD-L1_ Treatment Leads to Clinical Activity in Metastatic Bladder Cancer", Nature, 2014, pp. 558-562, Methods, Extended Data Figures 1-3, and Extended Data Table 1-3, vol. 515, No. 7528.
Reuter, "Diet-Induced Models for Obesity and Type 2 Diabetes", Drug Discovery Today: Disease Models, 2007, pp. 3-8, vol. 4/1.
Seiffert et al., "Signal-Regulatory Protein Alpha (SIRPalpha) but not SIRPbeta is Involved in T-cell Activation, Binds to CD47 with High Affinity, and is Expressed on Immature CD34(+)CD38(-) Hematopoietic Cells", Blood, May 2001, pp. 2741-2749, vol. 97, No. 9.
Sharma et al., "Immune Checkpoint Targeting in Cancer Therapy: Towards Combination Strategies with Curative Potential", Cell, 2015, pp. 205-214, vol. 161, No. 2.
Sim et al., "Discovery of High Affinity, Pan-Allelic, and Pan-Mammalian Reactive Antibodies Against the Myeloid Checkpoint Receptor SIRPa", MABS, 2019, pp. 1036-1052, vol. 11, No. 6.
Srivastava et al., "Targeting MDSCs Enhance Therapeutic Vaccination Responses Against Lung Cancer", Oncoimmunology, Dec. 2012, pp. 1650-1651, vol. 1, No. 9.
Stefanidakis et al., "Endothelial CD47 Interaction with SIRPgamma is Required for Human T-cell Transendothelial Migration under Shear Flow Conditions In Vitro", Blood, Aug. 2008, pp. 1280-1289, vol. 112, No. 4, The American Society of Hematology.
Takenaka et al., "Polymorphism in Sira Modulates Engraftment of Human Hematopoietic Stem Cells", Nature Immunology, Dec. 1, 2007,pp. 1313-1323, vol. 8, No. 12, Nature Publishing Group US, New York.
Topalian et al., "Safety, Activity, and Immune Correlates of Anti-PD-1 Antibody in Cancer", The new England Journal of Medicine, 2012, pp. 2443-2454, vol. 366, No. 26.
Türkbeyler et al., "Prolidase Could Act as a Diagnosis and Treatment Mediator in Lung Fibrosis", Inflammation, Oct. 2012, pp. 1747-1752, vol. 35, No. 5.
Ueda et al., "Association of the T-Cell Regulatory Gene CTLA4 with Susceptibility to Autoimmune Disease", Nature, 2003, pp. 506-511, vol. 423.
UniProt Sequence Accession O75144 for PDCD1_HUMAN; retrieved from the internet site https://uniprot.org/uniprot/ on Mar. 26, 2020.
UniProt Sequence Accession P23510 for PDCD1_HUMAN; retrieved from the internet site https://uniprot.org/uniprot/ on Mar. 26, 2020.
UniProt Sequence Accession P33681 for PDCD1_HUMAN; retrieved from the internet site https://uniprot.org/uniprot/ on Mar. 26, 2020.
UniProt Sequence Accession P41273 for PDCD1_HUMAN; retrieved from the internet site https://uniprot.org/uniprot/ on Mar. 26, 2020.
UniProt Sequence Accession P42081 for PDCD1_HUMAN; retrieved from the internet site https://uniprot.org/uniprot/ on Mar. 26, 2020.
UniProt Sequence Accession Q15116 for PDCD1_HUMAN; retrieved from the internet site https://uniprot.org/uniprot/ on Mar. 26, 2020.
UniProt Sequence Accession Q9NZQ7 for PDCD1_HUMAN; retrieved from the internet site https://uniprot.org/uniprot/ on Mar. 26, 2020.
Vinay et al., "Therapeutic Potential of Anti-CD137 (4-1BB) Monoclonal Antibodies", Expert Opin. Ther. Targets., 2016, pp. 361-373, vol. 20, No. 3.
Vonderheide, "CD47 Blockade as Another Immune Checkpoint Therapy for Cancer", Nature Medicine, Oct. 2015, pp. 1122-1123, vol. 21, No. 10.
Wakabayashi et al., "Prevention of Metastasis by a Polyamine Synthesis Inhibitor in an Animal Bone Metastasis Model", Oncology, 2000, pp. 75-80, vol. 59.
Dugast et al, "Myeloid-Derived Suppressor Cells Accumulate in Kidney Allograft Tolerance and Specifically Suppress Effector T Cell Expansion", The Journal of Immunology, Jun. 15, 2008, pp. 7898-7906, vol. 180, Issue. 12.
English Translation of Decision of Refusal for Japanese App No. 2018-521040, dated Sep. 21, 2021.
English Translation of Decision to Grant for Japanese App No. 2017-520986, dated Apr. 12, 2021.
English Translation of First Office Action for Japanese App No. 2017-520986, dated Aug. 5, 2019.
English Translation of First Office Action for Japanese App No. 2018-521040, dated Oct. 13, 2020.
English Translation of Second Office Action for Japanese App No. 2017-520986, dated May 21, 2020.
Kong et al., "CD47: A Potential Immunotherapy Target for Eliminating Cancer Cells", Clinical and Translational Oncology, 2016, pp. 1051-1055, vol. 18.
Megahed et al., "Reliability of Diagnosis of Melanoma in situ", The Lancet, 2002, pp. 1921-1922, vol. 359.
Solito et al, "Myeloid-Derived Suppressor Cell Heterogeneity in Human Cancers", Ann. N.Y. Acad. Sci. Jun. 2014, pp. 47-65, vol. 1319, Issue. 1.
"Anti-SHPS-1 Antibody, clone P84 clone P84, from rat", Sigma-Aldrich, visited online in 2021, 3 p. URL: https://www.sigmaaldrich.com/catalog/product/mm/mabs164?lang=en&region=NL#.
"Bristol-Myers Squibb Receives Accelerated Approval of Opdivo (nivolumab) from the U.S. Food and Drug Administration", Bristol Myers Squibb, 2014, 5 pages.
"Bristol-Myers Squibb Receives Approval from the U.S. Food and Drug Administration for the Opdivo (nivolumab) + Yervoy (ipilimumab) Regimen in Braf V600 Wild-Type Unresectable or Metastatic Melanoma", Bristol Myers Squibb, 2015, 6 pages.
"FDA Approves YERVOYTM (ipilimumab) for the Treatment of Patients with Newly Diagnosed or Previously-Treated Unresectable or Metastatic Melanoma, the Deadliest Form of Skin Cancer", Bristol Myers Squibb, 2011, 6 pages.
"Merck Receives Accelerated Approval of KEYTRUDA® (pembrolizumab), the First FDA-Approved Anti-PD-1 Therapy", MERCK, 2014, 9 pages.
Albanesi et al., "Cutting Edge: FcyRIII (CD16) and FcyRI (CD64) Are Responsible for Anti-Glycoprotein 75 Monoclonal Antibody TA99 Therapy for Experimental Metastatic B16 Melanoma", The Journal of Immunology, 2012, pp. 5513-5517, vol. 189, No. 12.
Bd Pharmingen, "Purified Rat Anti-Mouse CD172a", Technical Data Sheet, 2008, 2 pages.
Biolegend, "Purified anti-mouse CD172a (SIRPa)", Product Data Sheet, 2012, 2 pages.
Blazar et al., "CD47 (integrin-associated protein) engagement of dendritic cell and macrophage counterreceptors is required to prevent the clearance of donor lymphohematopoietic cells", Journal of Experimental Medicine, 2001, pp. 541-549, vol. 194, No. 4.
Chuang et al., "Central Nervous System Antigen P84 Can Serve as a Substrate for Neurite Outgrowth", Developmental Biology, 1990, pp. 219-232, vol. 137.
Gauttier et al. "Selective SIRPa blockade reverses tumor T cell exclusion and overcomes cancer immunotherapy resistance", The Journal of Clinical Investigation, Nov. 2020, vol. 130, No. 11.
House et al., "Recent technological advances in using mouse models to study ovarian cancer", Frontiers in Oncology, 2014, 7 pages, vol. 4, No. 26.
Jiang et al., "Integrin-associated Protein Is a Ligand for the P84 Neural Adhesion Molecule*", The Journal of Biological Chemistry, 1999, pp. 559-562, vol. 274, No. 2.
Merk, "Anti-SHPS-1, clone P84", Certificate of Analysis, 2014, 2 pages.
Murata et al., "Anti-human SIRPa antibody is a new tool for cancer immunotherapy", Wiley Cancer Science, 2018 , pp. 1300-1308, vol. 109.
Ohnishi et al., "Differential Localization of Src Homology 2 Domain-Containing Protein Tyrosine Phosphatase Substrate-1 and CD47 and Its Molecular Mechanisms in Cultured Hippocampal Neurons", The Journal of Neuroscience, 2005, pp. 2702-2711, vol. 25, No. 10.
Okazawa et al., "Negative Regulation of Phagocytosis in Macrophages by the CD47-SHPS-1 System1", The journal of Immunology, 2005, pp. 2004-2011, vol. 174, No. 4.
Oldenborg et al., "CD47-Signal Regulatory Protein a (SIRP a ) Regulates Fcg and Complement Receptor- mediated Phagocytosis", Journal of Experimental Medicine, 2001, pp. 855-861, vol. 193, No. 7.

(56) References Cited

OTHER PUBLICATIONS

Olsson et al., "Platelet homeostasis is regulated by platelet expression of CD47 under normal conditions and in passive immune thrombocytopenia", BLOOD, May 2005, vol. 105, No. 9.

Stewart, "Keytruda FDA Approval History", Drugs.com, visited on Mar. 15, 2023, 10 pages, URL: https://www.drugs.com/history/keytruda.html.

Teraoka et al., "Expression of Recipient CD47 on Rat Insulinoma Cell Xenografts Prevents Macrophage-Mediated Rejection through SIRPa Inhibitory Signaling in Mice", Plos One, Mar. 2013, 8 pages, vol. 8, No. 3.

Wang et al., "Attenuation of phagocytosis of xenogeneic cells by manipulating CD47", Blood, Jan. 2007, pp. 836-842, vol. 109, No. 2.

Sockolosky et al., "Durable antitumor responses to CD47 blockade require adaptive immune stimulation", Proceedings of the National Academy of Sciences, 2016, pp. E2646-E2654, vol. 113, No. 19.

\* cited by examiner

|  | Association (ka) (1/Ms) | Dissociation (kd) (1/s) | Affinity (KD) (M) |
|---|---|---|---|
| mouse 18D5 | 6,23e4 | 1,20e-5 | 1,93e-10 |
| chimeric | 1,49e5 | 5,14e-5 | 3,44e-10 |
| HFLA | 8,57e5 | 1,86e-4 | 2,17e-10 |
| HFLB | 7,91e5 | 2,49e-4 | 3,15e-10 |
| HEFLA | 5,59e5 | 1,48e-4 | 2,64e-10 |
| HEFLB | 6,54e5 | 1,89e-4 | 2,89e-10 |
| SIRP29 | 4,15e4 | 1,01e-5 | 2,43e-10 |
| Kwar23 | 2,44e5 | 8,95e-5 | 3,67e-10 |
| SE7C2 | 5,98e3 | 0,01 | 1,67e-6 |
| SE5A5 | 2,45e4 | 9,49e-4 | 3,87e-8 |

Figure 2

First experiment

Second experiment

| A | Association (ka) (1/Ms) | Dissociation (kd) (1/s) | Affinity (KD) (M) |
|---|---|---|---|
| mouse 18D5 | 1,58e4 | 1,76e-3 | 1,11e-7 |
| mouse 18D5 with SP-D | 3,797e5 | 1,088e-2 | 2,865e-8 |

Figure 6A

| B | Association (ka) (1/Ms) | Dissociation (kd) (1/s) | Affinity (KD) (M) |
|---|---|---|---|
| SP-D | 2,465e3 | 1,078e-2 | 4,372e-6 |
| SPD with mouse 18D5 | 3,272e3 | 2,405e-3 | 7,35e-7 |

Figure 6B

| | Association (ka) (1/Ms) | Dissociation (kd) (1/s) | Affinity (KD) (M) |
|---|---|---|---|
| Chimeric | 8,837e4 | 1,385e-3 | 1,568e-8 |
| HALA | 1,328e5 | 8,504e-4 | 6,403e-9 |
| HFLA | 7,447e4 | 1,919e-3 | 2,576e-8 |
| HFLB | 6,694e4 | 1,738e-3 | 2,596e-8 |
| HEFLA | 9,827e4 | 1,221e-3 | 1,243e-8 |
| HEFLB | 1,939e4 | 1,711e-3 | 8,69e-8 |
| SIRP29 | 1,078e5 | 8,114e-4 | 7,531e-9 |
| kwar23 | 2,863e5 | 7,935e-4 | 2,772e-9 |

| | Association (ka) (1/Ms) | Dissociation (kd) (1/s) | Affinity (KD) (M) |
|---|---|---|---|
| Chimeric | 4,93e4 | 3,194e-3 | 6,479e-8 |
| HALA | 1,539e5 | 7,093e-3 | 4,609e-8 |
| HFLA | 2,477e5 | 1,18e-2 | 4,764e-8 |
| HFLB | 1,191e5 | 1,234e-2 | 1,036e-7 |
| HEFLA | 2,173e5 | 1,14e-2 | 5,244e-8 |
| HEFLB | 1,92e5 | 1,193e-2 | 6,215e-8 |
| SIRP29 | 1,36e5 | 7,2e-4 | 5,296e-9 |
| kwar23 | 3,57e5 | 7,648e-4 | 2,142e-9 |

|  | Association (ka) (1/Ms) | Dissociation (kd) (1/s) | Affinity (KD) (M) |
|---|---|---|---|
| CD47 alone | 2,193e4 | 1,309e-2 | 5,969e-7 |
| HEFLB +CD47 | 5,372e4 | 5,334e-2 | 9,928e-7 |
| SIRP29 +CD47 | 2,118e4 | 5,525e-2 | 2,572e-6 |
| Kwar23 +CD47 | 4,369e2 | 1,259e-1 | 2,88e-4 |

Figure 9

| | Ctrl Ab II | Humanized 18D5 | SIRP29 (aSIRPa mAb) | Kwar23 (aSIRPa mAb) | Mouse isotype Ctrl | B4B6 (aSIRPb mAb) | LSB2.20 (aSIRPg mAb) | SE5A5 (aSIRPa/b mAb) | B6H12 (aCD47 mAb) | SIRPa-fc |
|---|---|---|---|---|---|---|---|---|---|---|
| Exp 1 HV1 | 0,45 | 1,54 | 73,5 | 80 | 0 | 0,87 | 91,4 | 3,72 | 100 | 72,2 |
| Exp 1 HV2 | 1,12 | 0,84 | 75,2 | 89,3 | 0,016 | 0,25 | 98,4 | 7,69 | 100 | 80,1 |
| Exp 2 HV1 | 0,057 | 0,016 | | | | | | | 99,9 | |
| Exp 2 HV2 | 0,076 | 0,058 | | | | | | | 99,9 | |

RBCs  Platelets

ANTI-SIRPa ANTIBODIES AND THEIR THERAPEUTIC APPLICATIONS

CROSS-REFERENCE TO RELATED APPLICATIONS

This application is a U.S. Divisional Application of U.S. application Ser. No. 16/093,062, filed Oct. 11, 2018, now U.S. Pat. No. 11,279,766, which is a U.S. National Phase Application of PCT/EP2017/059071, filed Apr. 14, 2017, which claims priority to European Patent Application No. 17305182.2, filed Feb. 17, 2017, and U.S. Provisional Patent Application No. 62/322,707, filed Apr. 14, 2016, all of which are incorporated herein by reference in their entireties.

REFERENCE TO SEQUENCE LISTING SUBMITTED ELECTRONICALLY

The content of the electronically submitted sequence listing in ASCII text file (Name 216838_Sequence_listing.txt; Size: 68,608 bytes; and Date of Creation: Sep. 18, 2018) filed with the application is incorporated herein by reference in its entirety.

The invention pertains to the field of immunotherapy. The present invention provides new anti-SIRPa antibodies able to specifically decreases the interaction between SIRPa and CD47 without affecting the interaction between SIRPg and CD47.

Targeting immune checkpoints of the adaptive immunity has shown great therapeutic efficacy to fight numerous cancers, but in a limited proportion of patients. Immune checkpoint on myeloid cells (macrophages, dendritic cells, MDSC, PMN) remain poorly studied while these cells represent the most abundant immune cell type in many solid tumors and are often associated with a poor outcome.

Signal regulatory protein alpha or SIRPa (also designated as SIRPα, CD172a or SHPS-1), is expressed on monocytes, most subpopulations of tissue macrophages, granulocytes, subsets of dendritic cells in lymphoid tissues, some bone marrow progenitor cells, and to varying levels on neurons, with a notably high expression in synapse-rich areas of the brain, such as the granular layer of the cerebellum and the hippocampus. SIRPa is the prototypic member of the SIRP paired receptor family of closely related SIRP proteins. The gene coding for human SIRPa is a polymorphic gene and several variants were described in human population. The most common protein variants are SIRPa v1 and v2 (accession numbers NP_542970 (P78324) and CAA71403). The polymorphisms in human SIRP lead to changes in surface-exposed amino acids, but this does not affect binding to CD47.

Interaction of SIRPa, expressed by myeloid cells, with the ubiquitous receptor CD47 is an important immune checkpoint of the innate response, involved in the regulation of myeloid functions. The SIRPa interaction with CD47 is largely described and provides a downregulatory signal that inhibits host cell phagocytosis. CD47 is widely expressed at lower levels by most healthy cells but it is also overexpressed in some cancer cells. Therefore, CD47 functions as a "don't-eat-me" signal. Both CD47 and SIRPa also engage in many other interactions. One of the best characterized physiological functions of the CD47-SIRPa interaction is its role in the homeostasis of hematopoietic cells, in particular red blood cells and platelets. Because CD47 serves as a "don't-eat-me" signal and, as such, is an important determinant of host cell phagocytosis by macrophages, the potential contribution of CD47-SIRPa interaction in cancer cell clearance has been intensely investigated in recent years. It was shown that abundance of CD47 receptors in tumors is inversely correlated with patient overall survival and constitute an adverse prognostic factor for several cancer types.

The SIRPa/CD47 pathway is nowadays subject to different pharmaceutical developments to enhance macrophages phagocytosis. In fact, like infected cells, cancer cells carry aberrant cargo such as unfamiliar proteins or normal proteins at abnormal levels, yet these cells frequently subvert innate immune control mechanisms by concurrently over-expressing immunoregulatory molecules. It is becoming clear that one such mechanism involves CD47, a protein of "self" expressed by normal cells. CD47 interacts with SIRPa and leads to the transmission of a "don't eat me" signal to phagocytic macrophages, which then leave target cells unaffected. Over-expression of CD47 by cancer cells renders them resistant to macrophages, even when the cancer cells are coated with therapeutic antibodies, and correlates with poor clinical outcomes in numerous solid and hematological cancers. In experimental models, in particular human tumor-xenograft models in immunodeficient mice, blockade of the CD47/SIRPa pathway via agents targeting CD47 was very effective to promote tumor elimination by macrophages and to decrease cancer cell dissemination and metastasis formation. Blockade of the CD47/SIRPa pathway via agents targeting CD47, by enhancing antibody-dependent phagocytosis by macrophages, has been described to synergize with depleting therapeutic anticancer antibodies such as Trastuzumab (anti-Her2), Cetuximab (anti-EGFR), Rituximab (anti-CD20) and Alemtuzumab (anti-CD52).

However, it has recently been shown that agents targeting CD47 (anti-CD47 or SIRPa-Fc) present hematological toxicity (anemia or thrombocytopenia) related to CD47 physiological role.

Besides, CD47 also engages with another member of the SIRP family, SIRP-gamma (also designated as SIRPg, SIRPγ, CD172g or SIRP beta 2) that is present at the surface of human T cells and not on human myeloid cells. SIRPg is the result of a duplication of SIRPb gene in old-world primates nearly 35 million years ago and it is expressed in a restricted manner on T lymphocytes as opposed to SIRPa expression on myeloid cells. SIRPg is absent in mice. It has been shown that the SIRPg-CD47 interaction mediates cell-cell adhesion, enhances superantigen-dependent T-cell-mediated proliferation and co-stimulates T-cell activation (Piccio et al., Blood, 105:6, 2005).

Due to the high similarity of sequences between SIRPa and SIRPg, in particular in the region that interacts with CD47, the anti-SIRPa antibodies disclosed in the prior art also bind SIRPg and have undesirable effects in humans such as an inhibition of the proliferation of T-cells and a decrease of the immune response. Such side effects of anti-CD47 or non-selective anti-SIRPa antibodies could not be predicted since the tests of the known antibodies were performed in mice models, which do not possess the SIRPg gene, and thus such side effects were absent.

There remains therefore a significant need in the art for new and improved agents, in particular antibodies, for safe immunotherapy, notably against cancer, targeting innate immune cells without deleterious impact on T cell immune responses. In particular, there is a need for inhibiting the SIRPa-CD47 interaction without affecting the SIRPg-CD47 interaction. The present inventors have made a significant step forward with the invention disclosed herein.

The purpose of the invention is to fulfill this need by providing new agents, in particular antibodies, which make it possible to solve in whole or part the problems mentioned-above.

Here, the Inventors provide new anti-SIRPa antibodies, in particular humanized antibodies, that antagonize the SIRPa-CD47 interaction but do not specifically bind SIRPg and, thus, do not affect the SIRPg-CD47 interaction.

The antibodies of the invention have in particular the following advantages:
- They avoid hematological toxicity due to restricted expression of SIRPa (no binding to human Red Blood Cells (RBC) and platelets);
- They reduce tumor growth and modify tumor microenvironment in monotherapy;
- They present synergistic effect with checkpoint inhibitors and costimulatory agents;
- They induce durable and robust anti-tumor memory T lymphocytes responses;
- They enable human T cell immune responses, being selective antagonist of SIRPa-CD47 interaction, not disturbing the CD47/SIRPg interaction. Unexpectedly, the inventors provide such selective antibodies despite the high sequence identity between SIRPa and SIRPg sequences.

These new antibodies selected on the basis of these characteristics are particularly promising for numerous therapeutic applications, in particular for the treatment of cancer including inflammatory cancers and cancers with infiltrated myeloid cells (in particular with infiltrated MDSCs and/or TAM cells).

SIRPa Antibodies (with Epitopes)

In an aspect, the invention relates to an anti-SIRPa antibody or antigen-binding fragment thereof or antigen-binding antibody mimetic that specifically binds to at least one peptide comprising or consisting of amino acid sequence selected from the group consisting of SEQ ID NO: 1 (SLIPVGP), SEQ ID NO: 2 (G/ARELIYNQKEGH), SEQ ID NO: 3 (KFRKGSPD[DV]/[T]E), SEQ ID NO: 4 (QHTVSFTCESHGFSPRDITLKWF), SEQ ID NO: 5 (ICE-VAHVTLQG) and SEQ ID NO: 6 (YPQRLQLTWLE) within SIRPa.

Unless defined otherwise, all technical and scientific terms used herein have the same meaning as commonly understood to one skilled in the relevant art.

For convenience, the meaning of certain terms and phrases employed in the specification, examples, and claims are provided.

As used herein, the term "antibody" comprises polyclonal antibodies, monoclonal antibodies or recombinant antibodies.

As used herein, a "monoclonal antibody" is intended to refer to a preparation of antibody molecules, antibodies which share a common heavy chain and common light chain amino acid sequence, in contrast with "polyclonal" antibody preparations which contain a mixture of antibodies of different amino acid sequence. Monoclonal antibodies can be generated by several known technologies like phage, bacteria, yeast or ribosomal display, as well as by classical methods exemplified by hybridoma-derived antibodies. Thus, the term "monoclonal" is used to refer to all antibodies derived from one nucleic acid clone.

The antibodies of the present invention include recombinant antibodies. As used herein, the term "recombinant antibody" refers to antibodies which are produced, expressed, generated or isolated by recombinant means, such as antibodies which are expressed using a recombinant expression vector transfected into a host cell; antibodies isolated from a recombinant combinatorial antibody library; antibodies isolated from an animal (e.g. a mouse) which is transgenic due to human immunoglobulin genes; or antibodies which are produced, expressed, generated or isolated in any other way in which particular immunoglobulin gene sequences (such as human immunoglobulin gene sequences) are assembled with other DNA sequences. Recombinant antibodies include, for example, chimeric and humanized antibodies.

As used herein, a "chimeric antibody" refers to an antibody in which the sequence of the variable domain derived from the germline of a mammalian species, such as a mouse, have been grafted onto the sequence of the constant domain derived from the germline of another mammalian species, such as a human.

As used herein, a "humanized antibody" refers to an antibody in which CDR sequences derived from the germline of another mammalian species, such as a mouse, have been grafted onto human framework sequences.

As used herein, an "antigen-binding fragment of an antibody" means a part of an antibody, i.e. a molecule corresponding to a portion of the structure of the antibody of the invention, that exhibits antigen-binding capacity for SIRPa, possibly in its native form; such fragment especially exhibits the same or substantially the same antigen-binding specificity for said antigen compared to the antigen-binding specificity of the corresponding four-chain antibody. Advantageously, the antigen-binding fragments have a similar binding affinity as the corresponding 4-chain antibodies. However, antigen-binding fragment that have a reduced antigen-binding affinity with respect to corresponding 4-chain antibodies are also encompassed within the invention. The antigen-binding capacity can be determined by measuring the affinity between the antibody and the target fragment. These antigen-binding fragments may also be designated as "functional fragments" of antibodies.

Antigen-binding fragments of antibodies are fragments which comprise their hypervariable domains designated CDRs (Complementary Determining Regions) or part(s) thereof encompassing the recognition site for the antigen, i.e. the extracellular domain of SIRPa, thereby defining antigen recognition specificity.

Each Light and Heavy chain variable domains (respectively VL and VH) of a four-chain immunoglobulin has three CDRs, designated VL-CDR1 (or LCDR1), VL-CDR2 (or LCDR2), VL-CDR3 (or LCDR3) and VH-CDR1 (or HCDR1), VH-CDR2 (or HCDR2), VH-CDR3 (or HCDR3), respectively.

The skilled person is able to determine the location of the various regions/domains of antibodies by reference to the standard definitions in this respect set forth, including a reference numbering system, a reference to the numbering system of KABAT or by application of the IMGT "collier de perle" algorithm. In this respect, for the definition of the sequences of the invention, it is noted that the delimitation of the regions/domains may vary from one reference system to another. Accordingly, the regions/domains as defined in the present invention encompass sequences showing variations in length or localization of the concerned sequences within the full-length sequence of the variable domains of the antibodies, of approximately +/−10%.

Based on the structure of four-chain immunoglobulins, antigen-binding fragments can thus be defined by comparison with sequences of antibodies in the available databases and prior art, and especially by comparison of the location of the functional domains in these sequences, noting that the positions of the framework and constant domains are well defined for various classes of antibodies, especially for IgGs, in particular for mammalian IgGs. Such comparison also involves data relating to 3-dimensional structures of antibodies.

For illustration purpose of specific embodiments of the invention, antigen binding fragments of an antibody that contain the variable domains comprising the CDRs of said antibody encompass Fv, dsFv, scFv, Fab, Fab', F(ab')2. Fv fragments consist of the VL and VH domains of an antibody associated together by hydrophobic interactions; in dsFv fragments, the VH:VL heterodimer is stabilised by a disulphide bond; in scFv fragments, the VL and VH domains are connected to one another via a flexible peptide linker thus forming a single-chain protein. Fab fragments are monomeric fragments obtainable by papain digestion of an antibody; they comprise the entire L chain, and a VH-CH1 fragment of the H chain, bound together through a disulfide bond. The F(ab')2 fragment can be produced by pepsin digestion of an antibody below the hinge disulfide; it comprises two Fab' fragments, and additionally a portion of the hinge region of the immunoglobulin molecule. The Fab' fragments are obtainable from F(ab')2 fragments by cutting a disulfide bond in the hinge region. F(ab')2 fragments are divalent, i.e. they comprise two antigen binding sites, like the native immunoglobulin molecule; on the other hand, Fv (a VHVL dimmer constituting the variable part of Fab), dsFv, scFv, Fab, and Fab' fragments are monovalent, i.e. they comprise a single antigen-binding site. These basic antigen-binding fragments of the invention can be combined together to obtain multivalent antigen-binding fragments, such as diabodies, tribodies or tetrabodies. These multivalent antigen-binding fragments are also part of the present invention.

As used herein, the term "bispecific" antibodies refers to antibodies that recognize two different antigens by virtue of possessing at least one region (e.g. derived from a variable region of a first antibody) that is specific for a first antigen, and at least a second region (e.g. derived from a variable region of a second antibody) that is specific for a second antigen. A bispecific antibody specifically binds to two target antigens and is thus one type of multispecific antibody. Multispecific antibodies, which recognize two or more different antigens, can be produced by recombinant DNA methods or include, but are not limited to, antibodies produced chemically by any convenient method. Bispecific antibodies include all antibodies or conjugates of antibodies, or polymeric forms of antibodies which are capable of recognizing two different antigens. Bispecific antibodies include antibodies that have been reduced and reformed so as to retain their bivalent characteristics and to antibodies that have been chemically coupled so that they can have several antigen recognition sites for each antigen such as BiME (Bispecific Macrophage Enhancing antibodies), BiTE (bispecific T cell engager), DART (Dual affinity retargeting); DNL (dock-and-lock), DVD-Ig (dual variable domain immunoglobulins), HAS (human serum albumin), kih (knobs into holes).

Accordingly, bispecific antibodies of the invention are directed against SIRPa and a second antigen.

In an embodiment, the invention relates to an anti-SIRPa antibody or antigen-binding fragment thereof or antigen-binding antibody mimetic as defined above that is bispecific.

Several researches to develop therapeutic antibodies had led to engineer the Fc regions to optimize antibody properties allowing the generation of molecules that are better suited to the pharmacology activity required of them. The Fc region of an antibody mediates its serum half-life and effector functions, such as complement-dependent cytotoxicity (CDC), antibody-dependent cellular cytotoxicity (ADCC) and antibody-dependent cell phagocytosis (ADCP). Several mutations located at the interface between the CH2 and CH3 domains, such as T250Q/M428L and M252Y/S254T/T256E+H433K/N434F, have been shown to increase the binding affinity to FcRn and the half-life of IgG1 in vivo. However, there is not always a direct relationship between increased FcRn binding and improved half-life. One approach to improve the efficacy of a therapeutic antibody is to increase its serum persistence, thereby allowing higher circulating levels, less frequent administration and reduced doses. Engineering Fc regions may be desired to either reduce or increase the effector function of the antibody. For antibodies that target cell-surface molecules, especially those on immune cells, abrogating effector functions is required. Conversely, for antibodies intended for oncology use, increasing effector functions may improve the therapeutic activity. The four human IgG isotypes bind the activating Fcγ receptors (FcγRI, FcγRIIa, FcγRIIIa), the inhibitory FcγRIII receptor, and the first component of complement (C1q) with different affinities, yielding very different effector functions. Binding of IgG to the FcγRs or C1q depends on residues located in the hinge region and the CH2 domain. Two regions of the CH2 domain are critical for FcγRs and C1q binding, and have unique sequences in IgG2 and IgG4.

As used herein, a "modified antibody" corresponds to a molecule comprising an antibody or an antigen-binding fragment thereof, wherein said monoclonal antibody or functional fragment thereof is associated with a functionally different molecule. A modified antibody of the invention may be either a fusion chimeric protein or a conjugate resulting from any suitable form of attachment including covalent attachment, grafting, chemical bonding with a chemical or biological group or with a molecule, such as a PEG polymer or another protective group or molecule suitable for protection against proteases cleavage in vivo, for improvement of stability and/or half-life of the antibody or functional fragment. With similar techniques, especially by chemical coupling or grafting, a modified antibody can be prepared with a biologically active molecule, said active molecule being for example chosen among toxins, in particular *Pseudomonas* exotoxin A, the A-chain of plant ricin or saporin toxin, especially a therapeutic active ingredient, a vector (including especially a protein vector) suitable for targeting the antibody or functional fragment to specific cells or tissues of the human body, or it may be associated with a label or with a linker, especially when fragments of the antibody are used. PEGylation of the antibody or functional fragments thereof is a particular interesting embodiment as it improves the delivery conditions of the active substance to the host, especially for a therapeutic application. PEGylation can be site specific to prevent interference with the recognition sites of the antibodies or functional fragments, and can be performed with high molecular weight PEG. PEGylation can be achieved through free cysteine residues present in the sequence of the antibody or functional fragment or through added free Cysteine residues in the amino sequence of the antibody or functional fragment.

In an embodiment, the invention relates to an anti-SIRPa antibody or antigen-binding fragment thereof or antigen-binding antibody mimetic as defined above that is modified.

The macromolecules of the invention comprise antibodies and fragments thereof but also comprise artificial proteins, peptides and any chemical compounds with the capacity to bind antigens mimicking that of antibodies, also termed herein antigen-binding antibody mimetic. Such proteins comprise affitins and anticalins. Affitins are artificial proteins with the ability to selectively bind antigens. They are structurally derived from the DNA binding protein Sac7d, found in *Sulfolobus acidocaldarius,* a microorganism belonging to the archaeal domain. By randomizing the amino acids on the binding surface of Sac7d, e.g. by generating variants corresponding to random substitutions of 11 residues of the binding interface of Sac7d, an affitin library may be generated and subjecting the resulting protein library to rounds of ribosome display, the affinity can be directed towards various targets, such as peptides, proteins, viruses and bacteria. Affitins are antibody mimetics and are being developed as tools in biotechnology. They have also been used as specific inhibitors for various enzymes (Krehenbrink et al., J. mol. Biol., 383:5, 2008). The skilled person may readily develop anticalins with the required binding properties using methods know in the art, in particular as disclosed in patent application WO2008068637 and the above-cited publication, in particular the generation of phage display and/or ribosome display libraries and their screening using an antigen as dislosed herein. Anticalins are artificial proteins that are able to bind to antigens, either to proteins or to small molecules. They are antibody mimetic derived from human lipocalins which are a family of naturally binding proteins. Anticalins are about eight times smaller with a size of about 180 amino acids and a mass of about 20 kDa (Skerra, Febs J., 275:11, 2008). Anticalin phage display libraries have been generated which allow for the screening and selection, in particular of anticalins with specific binding properties. The skilled person may readily develop affitins with the required binding properties using methods know in the art, in particular as disclosed in EP patent EP1270725 B1, U.S. Pat. No. 8,536,307 B2, (Schlehuber and Skerra, Biophys. Chem., 96:2-3, 2002) and the above-cited publication, in particular the generation of phage display and/or ribosome display libraries and their screening using an antigen as dislosed herein. Anticalins and affitins may both be produced in a number of expression system comprising bacterial expressin systems. Thus, the invention provides affitins, anticalins and other similar antibody mimetics with the features of the antibodies described herein, in particular with regard to the binding to SIRPa, the inhibition of the interaction between SIRPa and CD47, the non-binding to SIRPg, the non binding to T cells, the non inhibition of the proliferation of T cells, the non inhibition of the interaction between SIRPg and CD47 all of which are contemplated as macromolecules of the invention.

All the embodiments disclosed herein for antibodies or fragments thereof are transposed mutatis mutandis to the macromolecules of the invention, in particular to antigen-binding antibody mimetics.

As used herein, the term "epitope" means the part of an antigen to which the antibody binds. The epitopes of protein antigens can be divided into two categories, conformational epitope and linear epitope. A conformational epitope corresponds to discontinuous sections of the antigen's amino acid sequence. A linear epitope corresponds to a continuous sequence of amino acids from the antigen.

In the invention, the peptides that are present within SIRPa and that are bound by the anti-SIRPa antibodies are constitutive of the epitope specifically recognized by these antibodies.

In an embodiment, the invention relates to an anti-SIRPa antibody or antigen-binding fragment thereof or antigen-binding antibody mimetic that specifically binds to at least two, three, four or five peptides comprising or consisting of amino acid sequence selected from the group consisting of SEQ ID NO: 1 (SLIPVGP), SEQ ID NO: 2 (G/ARELIYNQKEGH), SEQ ID NO: 3 (KFRKGSPD[DV]/[T]E), SEQ ID NO: 4 (QHTVSFT-CESHGFSPRDITLKWF), SEQ ID NO: 5 (ICE-VAHVTLQG) and SEQ ID NO: 6 (YPQRLQLTWLE) within SIRPa.

In an embodiment, the invention relates to an anti-SIRPa antibody or antigen-binding fragment thereof or antigen-binding antibody mimetic that specifically binds to the peptide comprising or consisting of amino acid sequence SEQ ID NO: 3 (KFRKGSPD[DV]/[T]E) within SIRPa and to at least one peptide comprising or consisting of amino acid sequence selected from the group consisting of SEQ ID NO: 1 (SLIPVGP), SEQ ID NO: 2 (G/ARELIYNQKEGH), SEQ ID NO: 4 (QHTVSFTCESHGFSPRDITLKWF), SEQ ID NO: 5 (ICEVAHVTLQG) and SEQ ID NO: 6 (YPQRLQLTWLE) within SIRPa.

In an embodiment, the invention relates to an anti-SIRPa antibody or antigen-binding fragment thereof or antigen-binding antibody mimetic that specifically binds to the peptides comprising or consisting of amino acid sequence SEQ ID NO: 1 (SLIPVGP), SEQ ID NO: 2 (G/ARELIYNQKEGH), SEQ ID NO: 3 (KFRKGSPD[DV]/[T]E), SEQ ID NO: 4 (QHTVSFT-CESHGFSPRDITLKWF), SEQ ID NO: 5 (ICE-VAHVTLQG) and SEQ ID NO: 6 (YPQRLQLTWLE) within SIRPa.

In an embodiment, the invention relates to an anti-SIRPa antibody or antigen-binding fragment thereof or antigen-binding antibody mimetic that specifically binds to at least one peptide comprising or consisting of amino acid sequence selected from the group consisting of SEQ ID NO: 1 (SLIPVGP), SEQ ID NO: 7 (GRELIYNQKEGH), SEQ ID NO: 8 (KFRKGSPDDVE), SEQ ID NO: 4 (QHTVSFT-CESHGFSPRDITLKWF), SEQ ID NO: 5 (ICE-VAHVTLQG) and SEQ ID NO: 6 (YPQRLQLTWLE) within SIRPa.

In an embodiment, the invention relates to an anti-SIRPa antibody or antigen-binding fragment thereof or antigen-binding antibody mimetic as defined above that specifically binds to the peptides of SEQ ID NO: 1 (SLIPVGP), SEQ ID NO: 7 (GRELIYNQKEGH), SEQ ID NO: 8 (KFRKGSPDDVE), SEQ ID NO: 4 (QHTVSFT-CESHGFSPRDITLKWF), SEQ ID NO: 5 (ICE-VAHVTLQG) and SEQ ID NO: 6 (YPQRLQLTWLE) within SIRPa.

In an embodiment, the invention relates to an anti-SIRPa antibody or antigen-binding fragment thereof or antigen-binding antibody mimetic that specifically binds to at least one peptide comprising or consisting of amino acid sequence selected from the group consisting of SEQ ID NO: 1 (SLIPVGP), SEQ ID NO: 9 (ARELIYNQKEGH), SEQ ID NO: 10 (KFRKGSPDTE), SEQ ID NO: 4 (QHTVSFT-CESHGFSPRDITLKWF), SEQ ID NO: 5 (ICE-VAHVTLQG) and SEQ ID NO: 6 (YPQRLQLTWLE).

In an embodiment, the invention relates to an anti-SIRPa antibody or antigen-binding fragment thereof or antigen-binding antibody mimetic as defined above that specifically binds to the peptides of SEQ ID NO: 1 (SLIPVGP), SEQ ID NO: 9 (ARELIYNQKEGH), SEQ ID NO: 10 (KFRKGSPDTE), SEQ ID NO: 4 (QHTVSFT-CESHGFSPRDITLKWF), SEQ ID NO: 5 (ICE-VAHVTLQG) and SEQ ID NO: 6 (YPQRLQLTWLE) within SIRPa.

In an embodiment, the invention relates to an anti-SIRPa antibody or antigen-binding fragment thereof or antigen-binding antibody mimetic that specifically binds to at least one peptide comprising or consisting of amino acid sequence selected from the group consisting of SEQ ID NO: 1 (SLIPVGP), SEQ ID NO: 11 (GRELIYN), DVE, SEQ ID NO: 12 (HTVSFTCESHGFSPRDITLKWF), SEQ ID NO: 5 (ICEVAHVTLQG) and SEQ ID NO: 6 (YPQRLQLTWLE) within SIRPa.

In an embodiment, the invention relates to an anti-SIRPa antibody or antigen-binding fragment thereof or antigen-binding antibody mimetic as defined above that specifically binds to the peptides of SEQ ID NO: 1 (SLIPVGP), SEQ ID NO: 11 (GRELIYN), DVE, SEQ ID NO: 12 (HTVSFTCESHGFSPRDITLKWF), SEQ ID NO: 5 (ICEVAHVTLQG) and SEQ ID NO: 6 (YPQRLQLTWLE) within SIRPa.

In an embodiment, the invention relates to an anti-SIRPa antibody or antigen-binding fragment thereof or antigen-binding antibody mimetic that specifically binds to at least one peptide comprising or consisting of amino acid sequence selected from the group consisting of SEQ ID NO: 1 (SLIPVGP), SEQ ID NO: 13 (ARELIYN), SEQ ID NO: 12 (HTVSFTCESHGFSPRDITLKWF), SEQ ID NO: 5 (ICEVAHVTLQG) and SEQ ID NO: 6 (YPQRLQLTWLE) within SIRPa.

In an embodiment, the invention relates to an anti-SIRPa antibody or antigen-binding fragment thereof or antigen-binding antibody mimetic as defined above that specifically binds to the peptides of SEQ ID NO: 1 (SLIPVGP), SEQ ID NO: 13 (ARELIYN), SEQ ID NO: 12 (HTVSFTCESHGFSPRDITLKWF), SEQ ID NO: 5 (ICEVAHVTLQG) and SEQ ID NO: 6 (YPQRLQLTWLE) within SIRPa.

The peptides of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13 correspond to linear epitopes.

These linear epitopes have been identified by the inventors by array-based oligopeptide scanning (sometimes called overlapping peptide scan or pepscan analysis). This technique uses a library of oligo-peptide sequences from overlapping and non-overlapping segments of a target protein and tests for their ability to bind the antibody of interest. By combining non-adjacent peptide sequences from different parts of the target protein and enforcing conformational rigidity onto this combined peptide (such as by using CLIPS scaffolds) (Timmerman et al., 2007, J Mol Recognit., September-October; 20(5):283-99), discontinuous epitopes can be mapped with very high reliability and precision (Gaseitsiwe et al., 2010—Clin Vaccine Immunol. January; 17(1): 168-175). All of the tested antibodies of the invention, including HEFLB, specifically bind to said epitopes.

In an embodiment, the invention relates to an anti-SIRPa antibody or antigen-binding fragment thereof or antigen-binding antibody mimetic as defined above that specifically binds to a conformational epitope comprising at least one peptide selected from the group consisting of SEQ ID NO: 70 (ELIYNQKEGHFPR), SEQ ID NO: 71 (RNNMDFSIRIGN) and SEQ ID NO: 72 (SPRDITLKW) within SIRPa.

In an embodiment, the invention relates to an anti-SIRPa antibody or antigen-binding fragment thereof or antigen-binding antibody mimetic as defined above that specifically binds to a conformational epitope comprising or consisting of the peptides of SEQ ID NO: 70 (ELIYNQKEGHFPR), SEQ ID NO: 71 (RNNMDFSIRIGN) and SEQ ID NO: 72 (SPRDITLKW) within SIRPa.

In an embodiment, the invention relates to an anti-SIRPa antibody or antigen-binding fragment thereof or antigen-binding antibody mimetic as defined above that specifically binds to a conformational epitope comprising at least one peptide selected from the group consisting of SEQ ID NO: 70 (ELIYNQKEGHFPR) and SEQ ID NO: 71 (RNNMDFSIRIGN).

In an embodiment, the invention relates to an anti-SIRPa antibody or antigen-binding fragment thereof or antigen-binding antibody mimetic as defined above that specifically binds to a conformational epitope comprising or consisting of the peptides of SEQ ID NO: 70 (ELIYNQKEGHFPR) and SEQ ID NO: 71 (RNNMDFSIRIGN) within SIRPa.

In an embodiment, the invention relates to an anti-SIRPa antibody or antigen-binding fragment thereof or antigen-binding antibody mimetic as defined above that specifically binds to a conformational epitope comprising at least one peptide selected from the group consisting of SEQ ID NO: 73 (YNQK) and "SIR" within SIRPa.

In an embodiment, the invention relates to an anti-SIRPa antibody or antigen-binding fragment thereof or antigen-binding antibody mimetic as defined above that specifically binds to a conformational epitope comprising or consisting of the peptide of amino acid sequence set forth in SEQ ID NO: 73 (YNQK) and the peptide of SIR amino acid sequence within SIRPa.

The peptides of SEQ ID NO: 70, SEQ ID NO: 71, SEQ ID NO: 72, SEQ ID NO: 73 and SIRP correspond to conformational epitopes. These conformational epitopes have been determined by the inventors using proteolysis protection procedures (enzymatic digestion: chymotrypsin, trypsin of the antibody-antigen complex immobilized on affinity chromatography) following by mass spectrometry analyses (MALDI-TOF/TOF) to detect and sequence such peptides of interest, as well known by one skilled in the art (Van de Water et al., Clinical Immunology and Immunopathology, 1997, vol. 85). The antigen used was the human SIRPa (accession numbers NP_542970) and one of the antibodies of the invention used was the HEFLB variant.

The anti-SIRPa antibody or antigen-binding fragment thereof or antigen-binding antibody mimetic according to the invention specifically bind said conformational epitopes comprising or consisting of said peptides in their conformational arrangement within the native SIRPa.

The peptide of amino acid sequence set forth in SEQ ID NO: 73 (YNQK) corresponds to the peptide consisting of amino acids at position 80 to 83 in the human SIRPa amino acid sequence referenced by the NP_542970 accession number.

The peptide of SIR amino acid sequence, the SIR peptide, corresponds to the peptide consisting of amino acids at position 105 to 107 in the human SIRPa amino acid sequence referenced by the NP_542970 accession number.

As used herein, the term "SIRPa" refers to a SIRPa protein from a mammal species, preferably a human SIRPa (e.g. accession numbers NP_542970 (P78324) and CAA71403).

As used herein, the term "anti-SIRPa antibody" refers to an antibody which specifically binds to SIRPa, in particular to a human SIRPa.

The specific binding between the antibody or antigen-binding fragment thereof of the invention and the epitope (or the region comprising the epitope) implies that the antibody exhibits appreciable affinity for the epitope (the region comprising the epitope) on a particular protein or antigen (here SIRPa). "Appreciable affinity" includes binding with an affinity of about $10^{-9}$ M (KD) or stronger. Preferably, binding is considered specific when the binding affinity is between $10^{-9}$ M and $10^{-12}$ M, optionally between $10^{-9}$ M and $10^{-10}$ M, in particular $10^{-10}$ M. Whether a binding domain specifically reacts with or binds to a target can be tested readily by, inter alia, comparing the reaction of said binding domain with a target protein or antigen with the reaction of said binding domain with proteins or antigens other than the target protein.

The affinity can be determined by various methods well known from the one skilled in the art. These methods include, but are not limited to, Biacore Analysis, Blitz analysis and Scatchard plot.

In an embodiment, the invention relates to an anti-SIRPa antibody or antigen-binding fragment thereof or antigen-binding antibody mimetic as defined above that has a KD value inferior to $10^{-9}$ M, preferably inferior to $10^{-10}$ M for SIRPa, more preferably inferior to $1.10^{-11}$ M, particularly by Biacore Analysis.

In an embodiment, the invention relates to an anti-SIRPa antibody or antigen-binding fragment thereof or antigen-binding antibody mimetic as defined above that decreases the interaction between SIRPa and CD47.

In an embodiment, the invention relates to an anti-SIRPa antibody or antigen-binding fragment thereof or antigen-binding antibody mimetic as defined above that partially or fully, in particular fully, inhibits the binding of CD47 to SIRPa, in particular of human CD47 to human SIRPa.

Such an antibody of the invention specifically binds SIRPa and antagonizes the interaction between SIRPa and CD47.

In particular, the anti-SIRPa antagonist antibody of the invention is capable of reducing or inhibiting the binding of CD47 to SIRPa by at least 50%, 60%, 70%, preferably 80%, more preferably 90% or most preferably 100%, as compared to a negative control molecule, in a binding assay.

In particular, the anti-SIRPa antagonist antibody of the invention is capable of reducing or inhibiting the binding of CD47 to SIRPa by from 50% to 100%, preferably from 60% to 90%, more preferably from 70% to 80%, as compared to a negative control molecule, in a binding assay.

Methods for determining antibody specificity and affinity by competitive inhibition are known in the art (see, e.g., Harlow et al., Antibodies: A Laboratory Manual, Cold Spring Harbor Laboratory Press, Cold Spring Harbor, N.Y. (1998); Colligan et al., Current Protocols in Immunology, Green Publishing Assoc., NY (1992; 1993); Muller, Meth. Enzym., 92:589-601 (1983)) and described in the examples below.

These methods include, but are not limited to, Biacore Analysis, Blitz analysis, flow cytometry and ELISA assay.

In an embodiment, the invention relates to an anti-SIRPa antibody as defined above that has an IC50 lower than 500 ng/ml, in particular lower than 400 ng/ml, 300 ng/ml, more particularly lower than 200 ng/ml, as determined in a competitive SIRPa binding assay between CD47 and the anti-SIRPa antibody by ELISA.

In an embodiment, the invention relates to an anti-SIRPa antibody as defined above that has an IC50 lower than 500 ng/ml, in particular lower than 400 ng/ml, 300 ng/ml, more particularly lower than 200 ng/ml, lower than 150 ng/ml and even more particularly lower than 100 ng/ml as determined by competition cytometry assay on human monocytes between CD47 and the anti-SIRPa antibody.

In an embodiment, the invention relates to an anti-SIRPa antibody or antigen-binding fragment thereof or antigen-binding antibody mimetic as defined above that does not specifically bind to SIRPg, preferably to human SIRPg.

Such an antibody of the invention does not affect or does not prevent the interaction between SIRPg and CD47.

As used herein, the term "SIRPg" relates to a signal regulatory protein gamma (also designated SIRP gamma, CD172g or SIRP beta 2), from a mammal species, preferably a human SIRPg.

A reference sequence of the human SIRPg protein, used in the examples of the present application, corresponds to the sequence associated to the Accession number Q9P1W8.

In an embodiment, the invention relates to an anti-SIRPa antibody or antigen-binding fragment thereof or antigen-binding antibody mimetic as defined above that has a KD value superior to $10^{-9}$ M, preferably superior to $10^{-8}$ M, more preferably superior to $10^{-7}$ M for SIRPg, in particular by Blitz analysis.

In an embodiment, the invention relates to an anti-SIRPa antibody or antigen-binding fragment thereof or antigen-binding antibody mimetic as defined above that does not significantly inhibit, antagonize, the binding of CD47 to SIRP-g, that does not significantly compete with the binding of CD47 to SIRPg.

This antagonist effect can be determined using the methods as defined the examples of the present application.

In the invention, it can be considered that an antibody (or antigen-binding fragment thereof or antigen-binding antibody mimetic) does not antagonize the binding of CD47 to SIRPg if said antibody (or antigen-binding fragment thereof or antigen-binding antibody mimetic) induces no increase, or induces an increase inferior to 1 log, of the KD value of CD47 in a SIRPg binding competitive assay by Blitz.

In an embodiment, the invention relates to an anti-SIRPa antibody or antigen-binding fragment thereof or antigen-binding antibody mimetic as defined above that does not specifically bind to T-cells, in particular to CD3+ T-cells.

In particular, the anti-SIRPa antibody or antigen-binding fragment thereof or antigen-binding antibody mimetic of the invention does not bind to T-cells from mammal species, in particular to human T-cells.

In particular, it is considered that an anti-SIRPa antibody (or antigen-binding fragment thereof or antigen-binding antibody mimetic) does not specifically bind to human T cells if, in a population of human T cells isolated from PBMC from a healthy donor, less than 10%, preferably less than 5%, more preferably less than 2%, most preferably less than 1% of the population of human T cells are recognized by said anti-SIRPa antibody (or antigen-binding fragment thereof or antigen-binding antibody mimetic).

This effect can be measured by the methods as described in the examples of the present application.

In an embodiment, the invention relates to an anti-SIRPa antibody or antigen-binding fragment thereof or antigen-binding antibody mimetic as defined above that does not significantly inhibit the proliferation of T-cells, in particular CD3+ T-cells, preferably from mammal species and more preferably of human T cells.

In particular, it is considered that an anti-SIRPa antibody does not significantly inhibit the proliferation of T-cells if the proliferation of T-cells is reduced by less than 30%, preferably less than 20%, more preferably less than 10%, most preferably less than 5% as compared with a negative control.

The proliferation of T-cells can be determined by various methods. For example, the proliferation of T-cells can be measured by incorporation of $H^3$-thymidine as described in the examples of the present application.

In an embodiment, the invention relates to an anti-SIRPa antibody or antigen-binding fragment thereof or antigen-binding antibody mimetic as defined above that does not significantly inhibit, antagonize, the binding of the surfactant proteins to SIRP-a, that does not significantly compete with the binding of the surfactant proteins to SIRPa.

As used herein, the "surfactant proteins" are collagen-containing C-type (calcium dependent) lectins, which contribute significantly to surfactant homeostasis and pulmonary immunity (for review, see Kishore et al., Surfactant proteins SP-A and SP-D: structure, function and receptors, Mol Immunol, 43(9), 1293-315, 2006).

As used herein, the term "surfactant protein" refers to a surfactant protein from a mammal species, preferably a human surfactant protein.

In an embodiment, the invention relates to an anti-SIRPa antibody or antigen-binding fragment thereof or antigen-binding antibody mimetic as defined above that does not inhibit the binding of the human surfactant protein D (SP-D) to SIRPa.

In an embodiment, the invention relates to an anti-SIRPa antibody or antigen-binding fragment thereof or antigen-binding antibody mimetic as defined above that does not inhibit the binding of the human surfactant protein A (SP-A) to SIRPa.

In an embodiment, the invention relates to an anti-SIRPa antibody or antigen-binding fragment thereof or antigen-binding antibody mimetic as defined above that does not antagonize the interaction between the surfactant proteins and SIRPa.

The competition between SIRPa and surfactant proteins can be determined by competitive assay using methods well known from the one skilled in the art. These methods include, but are not limited to, Biacore Analysis, Blitz analysis and ELISA assay.

In the invention, it can be considered that an antibody (or antigen-binding fragment thereof or antigen-binding antibody mimetic) does not antagonize the binding of a surfactant protein to SIRPa if said antibody (or antigen-binding fragment thereof or antigen-binding antibody mimetic) induces no increase, or induces an increase inferior to 1 log, of the KD value of the surfactant protein in a SIRPa binding competitive assay by Blitz.

In an embodiment, the invention relates to an anti-SIRPa antibody or antigen-binding fragment thereof or antigen-binding antibody mimetic as defined above that weakly binds, or does not specifically bind to SIRPb.

As used herein, the term "SIRPb" refers to a SIRPb protein (also designated as SIRPβ, signal-regulatory protein beta-1, SIRP-beta-1, CD172 antigen-like family member B or CD172b) from a mammal species, preferably a human SIRPb.

A reference sequence of the human SIRPb protein, used in the examples of the present application, corresponds to the sequence associated to the Accession number Q5TFQ8-1.

In an embodiment, the invention relates to an anti-SIRPa antibody or antigen-binding fragment thereof or antigen-binding antibody mimetic as defined above that has KD value superior to $10^{-9}$ M, preferably superior to $10^{-8}$ M for SIRPb, in particular by Blitz analysis.

In an embodiment, the invention relates to an anti-SIRPa antibody or antigen-binding fragment thereof or antigen-binding antibody mimetic as defined above that comprises:
a) a heavy chain comprising HCDR1, HCDR2 and HCDR3, and/or
b) a light chain comprising LCDR1, LCDR2 and LCDR3, wherein said CDRs are defined as follows:
HCDR1 comprising or consisting of the amino acid sequence set forth in SEQ ID NO: 14 (SYWVH),
HCDR2 comprising or consisting of the amino acid sequence set forth in SEQ ID NO: 15 (NIDPSDSDTHYNQKFKD) or SEQ ID NO: 16 (NIDPSDSDTHYSPSFQG),
HCDR3 comprising or consisting of the amino acid sequence set forth in SEQ ID NO: 17 (GGTGTMAWFAY) SEQ ID NO: 18 (GGTGTLAWFAY), SEQ ID NO: 19 (GGTGTMAYFAY) or SEQ ID NO: 20 (GGTGTLAYFAY),
LCDR1 comprising or consisting of the amino acid sequence set forth in SEQ ID NO: 21 (RSSQSLVHSYGNTYLY),
LCDR2 comprising or consisting of the amino acid sequence set forth in SEQ ID NO: 22 (RVSNRFS), and
LCDR3 comprising or consisting of the amino acid sequence set forth in SEQ ID NO: 23 (FQGTHVPYT).

18D5/Variant A/Variant B

In an embodiment, the invention relates to an anti-SIRPa antibody or antigen-binding fragment thereof or antigen-binding antibody mimetic as defined above that comprises:
a) a heavy chain comprising HCDR1, HCDR2 and HCDR3, and/or
b) a light chain comprising LCDR1, LCDR2 and LCDR3, wherein said CDRs are defined as follows:
HCDR1 comprising or consisting of the amino acid sequence set forth in SEQ ID NO: 14 (SYWVH),
HCDR2 comprising or consisting of the amino acid sequence set forth in SEQ ID NO: 15 (NIDPSDSDTHYNQKFKD),
HCDR3 comprising or consisting of the amino acid sequence set forth in SEQ ID NO: 17 (GGTGTMAWFAY),
LCDR1 comprising or consisting of the amino acid sequence set forth in SEQ ID NO: 21 (RSSQSLVHSYGNTYLY),
LCDR2 comprising or consisting of the amino acid sequence set forth in SEQ ID NO: 22 (RVSNRFS), and
LCDR3 comprising or consisting of the amino acid sequence set forth in SEQ ID NO: 23 (FQGTHVPYT).

Variant C

In an embodiment, the invention relates to an anti-SIRPa antibody or antigen-binding fragment thereof or antigen-binding antibody mimetic as defined above that comprises:
a) a heavy chain comprising HCDR1, HCDR2 and HCDR3, and/or
b) a light chain comprising LCDR1, LCDR2 and LCDR3, wherein said CDRs are defined as follows:
HCDR1 comprising or consisting of the amino acid sequence set forth in SEQ ID NO: 14 (SYWVH),
HCDR2 comprising or consisting of the amino acid sequence set forth in SEQ ID NO: 16 (NIDPSDSDTHYSPSFQG),
HCDR3 comprising or consisting of the amino acid sequence set forth in SEQ ID NO: 17 (GGTGTMAWFAY),
LCDR1 comprising or consisting of the amino acid sequence set forth in SEQ ID NO: 21 (RSSQSLVHSYGNTYLY),
LCDR2 comprising or consisting of the amino acid sequence set forth in SEQ ID NO: 22 (RVSNRFS), and
LCDR3 comprising or consisting of the amino acid sequence set forth in SEQ ID NO: 23 (FQGTHVPYT).

Variant E

In an embodiment, the invention relates to an anti-SIRPa antibody or antigen-binding fragment thereof or antigen-binding antibody mimetic as defined above that comprises:
a) a heavy chain comprising HCDR1, HCDR2 and HCDR3, and/or
b) a light chain comprising LCDR1, LCDR2 and LCDR3, wherein said CDRs are defined as follows:
HCDR1 comprising or consisting of the amino acid sequence set forth in SEQ ID NO: 14 (SYWVH),
HCDR2 comprising or consisting of the amino acid sequence set forth in SEQ ID NO: 16 (NIDPSDSDTHYSPSFQG),
HCDR3 comprising or consisting of the amino acid sequence set forth in SEQ ID NO: 18 (GGTGTLAWFAY),
LCDR1 comprising or consisting of the amino acid sequence set forth in SEQ ID NO: 21 (RSSQSLVHSYGNTYLY),
LCDR2 comprising or consisting of the amino acid sequence set forth in SEQ ID NO: 22 (RVSNRFS), and
LCDR3 comprising or consisting of the amino acid sequence set forth in SEQ ID NO: 23 (FQGTHVPYT).
Variant F In an embodiment, the invention relates to an anti-SIRPa antibody or antigen-binding fragment thereof or antigen-binding antibody mimetic as defined above that comprises:
a) a heavy chain comprising HCDR1, HCDR2 and HCDR3, and/or
b) a light chain comprising LCDR1, LCDR2 and LCDR3, wherein said CDRs are defined as follows:
HCDR1 comprising or consisting of the amino acid sequence set forth in SEQ ID NO: 14 (SYWVH),
HCDR2 comprising or consisting of the amino acid sequence set forth in SEQ ID NO: 16 (NIDPSDSDTHYSPSFQG),
HCDR3 comprising or consisting of the amino acid sequence set forth in SEQ ID NO: 19 (GGTGTMAYFAY),
LCDR1 comprising or consisting of the amino acid sequence set forth in SEQ ID NO: 21 (RSSQSLVHSYGNTYLY),
LCDR2 comprising or consisting of the amino acid sequence set forth in SEQ ID NO: 22 (RVSNRFS), and
LCDR3 comprising or consisting of the amino acid sequence set forth in SEQ ID NO: 23 (FQGTHVPYT).
Variant EF In an embodiment, the invention relates to an anti-SIRPa antibody or antigen-binding fragment thereof or antigen-binding antibody mimetic as defined above that comprises:
a) a heavy chain comprising HCDR1, HCDR2 and HCDR3, and/or
b) a light chain comprising LCDR1, LCDR2 and LCDR3, wherein said CDRs are defined as follows:
HCDR1 comprising or consisting of the amino acid sequence set forth in SEQ ID NO: 14 (SYWVH),
HCDR2 comprising or consisting of the amino acid sequence set forth in SEQ ID NO: 16 (NIDPSDSDTHYSPSFQG),
HCDR3 comprising or consisting of the amino acid sequence set forth in SEQ ID NO: 20 (GGTGTLAYFAY),
LCDR1 comprising or consisting of the amino acid sequence set forth in SEQ ID NO: 21 (RSSQSLVHSYGNTYLY),
LCDR2 comprising or consisting of the amino acid sequence set forth in SEQ ID NO: 22 (RVSNRFS), and
LCDR3 comprising or consisting of the amino acid sequence set forth in SEQ ID NO: 23 (FQGTHVPYT).

The anti-SIRPa antibodies of the invention may have a heavy chain variable region comprising the amino acid sequence of HCDR1 and/or HCDR2 and/or HCDR3 of the human antibodies as provided herein; and/or a light chain variable region comprising the amino acid sequence of LCDR1 and/or LCDR2 and/or LCDR3 of the human antibodies as provided herein.

In an embodiment, the antibody comprises an amino acid sequence variant of one or more of the CDRs of the provided human antibodies, which variant comprises one or more amino acid insertion(s) within or adjacent to a CDR residue and/or deletion(s) within or adjacent to a CDR residue and/or substitution(s) of CDR residue(s) (with substitution(s) being the preferred type of amino acid alteration for generating such variants).

In an embodiment, the invention relates to an anti-SIRPa antibody or antigen-binding fragment thereof or antigen-binding antibody mimetic as defined above that comprises:
a heavy chain variable domain comprising or consisting of the amino acid sequence selected from SEQ ID NO: 24, SEQ ID NO: 25, SEQ ID NO: 26, SEQ ID NO: 27, SEQ ID NO: 28, SEQ ID NO: 29 and SEQ ID NO: 30, and/or
a light chain variable domain comprising or consisting of the amino acid sequence selected from the group consisting of SEQ ID NO: 31, SEQ ID NO: 32 and SEQ ID NO: 33.

In an embodiment, the invention relates to an anti-SIRPa antibody or antigen-binding fragment thereof or antigen-binding antibody mimetic as defined above that comprises:
a heavy chain variable domain comprising or consisting of the amino acid sequence selected from the group consisting of SEQ ID NO: 24, SEQ ID NO: 25, SEQ ID NO: 26, SEQ ID NO: 27, SEQ ID NO: 28, SEQ ID NO: 29 and SEQ ID NO: 30, and
a light chain variable domain comprising or consisting of the amino acid sequence selected from the group consisting of SEQ ID NO: 31, SEQ ID NO: 32 and SEQ ID NO: 33.

The sequences of the specific variable domains are given in Table 1 below.

TABLE 1

Examples of heavy chain variable domains and light chain variable domains of antibodies according to the invention.

| | | |
|---|---|---|
| Heavy chain variable domain of the wild-type antibody (chimeric and mouse 18D5) | QVQLQQPGAELVRPG SSVKLSCKASGYTFT SYWVHWVKQRPIQGL EWIGNIDPSDSDTHY NQKFKDKASLTVDKS SSTAYMQLSSLTFED SAVYYCVRGGTGTMA WFAYWGQGTLVTVSA | SEQ ID NO: 24 |
| Heavy chain variable domain of humanized variant (HA) | EVQLVQSGAEVKKPG ESLRISCKASGYTFT SYWVHWVRQMPGKGL EWIGNIDPSDSDTHY NQKFKDHVTLSVDKS ISTAYLQLSSLKASD TAMYYCVRGGTGTMA WFAYWGQGTLVTVSS | SEQ ID NO: 25 |
| Heavy chain variable | EVQLVQSGAEVKKPG ESLRISCKASGYSFT | SEQ ID NO: 26 |

TABLE 1-continued

Examples of heavy chain variable domains and light chain variable domains of antibodies according to the invention.

| | | |
|---|---|---|
| domain of humanized variant (HB) | SYWVHWVRQMPGKGL EWMGNIDPSDSDTHY NQKFKDHVTLSVDKS ISTAYLQLSSLKASD TAMYYCVRGGTGTMA WFAYWGQGTLVTVSS | |
| Heavy chain variable domain of humanized variant (HC) | EVQLVQSGAEVKKPG ESLRISCKASGYSFT SYWVHWVRQMPGKGL EWMGNIDPSDSDTHY SPSFQGHVTLSVDKS ISTAYLQLSSLKASD TAMYYCVRGGTGTMA WFAYWGQGTLVTVSS | SEQ ID NO: 27 |
| Heavy chain variable domain of humanized variant (HE) | EVQLVQSGAEVKKPG ESLRISCKASGYSFT SYWVHWVRQMPGKGL EWMGNIDPSDSDTHY SPSFQGHVTLSVDKS ISTAYLQLSSLKASD TAMYYCVRGGTGTLA WFAYWGQGTLVTVSS | SEQ ID NO: 28 |
| Heavy chain variable domain of humanized variant (HF) | EVQLVQSGAEVKKPG ESLRISCKASGYSFT SYWVHWVRQMPGKGL EWMGNIDPSDSDTHY SPSFQGHVTLSVDKS ISTAYLQLSSLKASD TAMYYCVRGGTGTMA YFAYWGQGTLVTVSS | SEQ ID NO: 29 |
| Heavy chain variable domain of humanized variant (HEF) | EVQLVQSGAEVKKPG ESLRISCKASGYSFT SYWVHWVRQMPGKGL EWMGNIDPSDSDTHY SPSFQGHVTLSVDKS ISTAYLQLSSLKASD TAMYYCVRGGTGTLA YFAYWGQGTLVTVSS | SEQ ID NO: 30 |
| Light chain of the wild-type antibody (chimeric and mouse 18D5) | DVVMTQTPLSLPVSL GDQASISCRSSQSLV HSYGNTYLYWYLQKP GQSPKLLIYRVSNRF SGVPDRFSGSGSGTD FTLKISRVEAEDLGV YFCFQGTHVPYTFGS GTKLEIK | SEQ ID NO: 31 |
| Light chain variable domain of humanized variant A (LA) | DVVMTQSPLSLPVTL GQPASISCRSSQSLV HSYGNTYLYWYQQRP GQSPRLLIYRVSNRF SGVPDRFSGSGSGTD FTLKISRVEAEDVGV YFCFQGTHVPYTFGG GTKVEIK | SEQ ID NO: 32 |
| Light chain variable domain of humanized variant (LB) | DVVMTQSPLSLPVTL GQPASISCRSSQSLV HSYGNTYLYWFQQRP GQSPRLLIYRVSNRF SGVPDRFSGSGSGTD FTLKISRVEAEDVGV YYCFQGTHVPYTFGG GTKVEIK | SEQ ID NO: 33 |

The sequences of the variable domains of the antibodies exemplified in the present invention can be deduced from the combinations of the sequences shown in Table 2.

TABLE 2

Heavy chain variable domain and light chain variable domain of specific antibodies according to the invention.

| Antibody | Heavy chain variable domain | Lightchain variable domain |
|---|---|---|
| 18D5 (chimeric and mouse) | SEQ ID NO: 24 | SEQ ID NO: 31 |
| HALA | SEQ ID NO: 25 | SEQ ID NO: 32 |
| HALB | SEQ ID NO: 25 | SEQ ID NO: 33 |
| HBLA | SEQ ID NO: 26 | SEQ ID NO: 32 |
| HBLB | SEQ ID NO: 26 | SEQ ID NO: 33 |
| HCLA | SEQ ID NO: 27 | SEQ ID NO: 32 |
| HCLB | SEQ ID NO: 27 | SEQ ID NO: 33 |
| HELA | SEQ ID NO: 28 | SEQ ID NO: 32 |
| HELB | SEQ ID NO: 28 | SEQ ID NO: 33 |
| HFLA | SEQ ID NO: 29 | SEQ ID NO: 32 |
| HFLB | SEQ ID NO: 29 | SEQ ID NO: 33 |
| HEFLA | SEQ ID NO: 30 | SEQ ID NO: 32 |
| HEFLB | SEQ ID NO: 30 | SEQ ID NO: 33 |

In an embodiment, the invention relates to an anti-SIRPa antibody or antigen-binding fragment thereof or antigen-binding antibody mimetic as defined above that comprises a light chain variable domain comprising or consisting of the amino acid sequence SEQ ID NO: 33.

In an embodiment, the invention relates to an anti-SIRPa antibody or antigen-binding fragment thereof or antigen-binding antibody mimetic as defined above that comprises:
 a light chain variable domain comprising or consisting of the amino acid sequence SEQ ID NO: 33, and
 a heavy chain variable domain comprising or consisting of the amino acid sequence selected from the group consisting of SEQ ID NO: 24, SEQ ID NO: 25, SEQ ID NO: 26, SEQ ID NO:27, SEQ ID NO: 28, SEQ ID NO: 29 and SEQ ID NO: 30,
 preferably
 a heavy chain variable domain comprising or consisting of the amino acid sequence selected from the group consisting of SEQ ID NO: 29 and SEQ ID NO: 30,
 more preferably
 a heavy chain variable domain comprising or consisting of the amino acid sequence selected from the group consisting of SEQ ID NO: 30.

In an embodiment, the invention relates to an anti-SIRPa antibody or antigen-binding fragment thereof or antigen-binding antibody mimetic as defined above that comprises:
 a heavy chain variable domain comprising or consisting of amino acid sequence set forth in SEQ ID NO: 24, and
 a light chain variable domain comprising or consisting of amino acid sequence set forth in SEQ ID NO: 31, or
 a heavy chain variable domain comprising or consisting of amino acid sequence set forth in SEQ ID NO: 25, and
 a light chain variable domain comprising or consisting of amino acid sequence set forth in SEQ ID NO: 32, or
 a heavy chain variable domain comprising or consisting of amino acid sequence set forth in SEQ ID NO: 25, and
 a light chain variable domain comprising or consisting of amino acid sequence set forth in SEQ ID NO: 33, or
 a heavy chain variable domain comprising or consisting of amino acid sequence set forth in SEQ ID NO: 26, and a light chain variable domain comprising or consisting of amino acid sequence set forth in SEQ ID NO: 32,
or
a heavy chain variable domain comprising or consisting of amino acid sequence set forth in SEQ ID NO: 26, and
a light chain variable domain comprising or consisting of amino acid sequence set forth in SEQ ID NO: 33,
or
a heavy chain variable domain comprising or consisting of amino acid sequence set forth in SEQ ID NO: 27, and
a light chain variable domain comprising or consisting of amino acid sequence set forth in SEQ ID NO: 32,
or
a heavy chain variable domain comprising or consisting of amino acid sequence set forth in SEQ ID NO: 27, and
a light chain variable domain comprising or consisting of amino acid sequence set forth in SEQ ID NO: 33,
or
a heavy chain variable domain comprising or consisting of amino acid sequence set forth in SEQ ID NO: 28, and
a light chain variable domain comprising or consisting of amino acid sequence set forth in SEQ ID NO: 32,
or
a heavy chain variable domain comprising or consisting of amino acid sequence set forth in SEQ ID NO: 28, and
a light chain variable domain comprising or consisting of amino acid sequence set forth in SEQ ID NO: 33,
or
a heavy chain variable domain comprising or consisting of amino acid sequence set forth in SEQ ID NO: 29, and
a light chain variable domain comprising or consisting of amino acid sequence set forth in SEQ ID NO: 32,
or
a heavy chain variable domain comprising or consisting of amino acid sequence set forth in SEQ ID NO: 29, and
a light chain variable domain comprising or consisting of amino acid sequence set forth in SEQ ID NO: 33,
or
a heavy chain variable domain comprising or consisting of amino acid sequence set forth in SEQ ID NO: 30, and
a light chain variable domain comprising or consisting of amino acid sequence set forth in SEQ ID NO: 32,
or
a heavy chain variable domain comprising or consisting of amino acid sequence set forth in SEQ ID NO: 30, and
a light chain variable domain comprising or consisting of amino acid sequence set forth in SEQ ID NO: 33.

In an embodiment, the antibody or antigen-binding fragment or antigen-binding antibody mimetic has no substitution of the amino acid W at position 33 (W33) in the heavy chain variable domain, said position being identified with respect to SEQ ID NO: 24, SEQ ID NO: 25, SEQ ID NO: 26, SEQ ID NO: 27, SEQ ID NO: 28, SEQ ID NO: 29 or SEQ ID NO: 30, and/or no substitution of the amino acids Y at position 39 (Y39), R at position 55 (R55) and/or F at position 60 (F60) in the light chain variable domain, said positions being identified with respect to SEQ ID NO: 31, SEQ ID NO: 32 or SEQ ID: 33, in particular has no substitution at position W33 in the heavy chain variable domain and no substitution at positions Y39, R55 and F60 in the light chain variable domain.

In the invention, the antibodies can be produced with any heavy chain and light chain constant domains. In one embodiment, the anti-human SIRPa antibody of the invention is a humanized monoclonal antibody, in particular wherein the antibody light chain constant domain is derived from a human kappa light chain constant domain, more particularly wherein the light chain constant domain consists of the sequence of SEQ ID NO: 35, and wherein the antibody heavy chain constant domain is derived from a human IgG1, IgG2, IgG3, or IgG4 (wild type or mutated) heavy chain constant domain, in particular from a human IgG4 heavy chain constant domain, more particularly wherein the antibody heavy chain constant domain consists of the sequence with SEQ ID NO: 34.

As well known by one skilled in the art, the choice of IgG isotypes of the heavy chain constant domain centers on whether specific functions are required and the need for a suitable in vivo half-life. For example, antibodies designed for selective eradication of cancer cells typically require an active isotype that permits complement activation and effector-mediated cell killing by antibody-dependent cell-mediated cytotoxicity. Both human IgG1 and IgG3 (shorter half-life) isotypes meet these criteria, particularly human IgG1 isotype (wild type and variants). In particular, depending of the IgG isotype of the heavy chain constant domain (particularly human wild type and variants IgG1 isotype), the anti-human SIRPa antibody of the invention can be cytotoxic towards cells expressing SIRPa via a CDC, ADCC and/or ADCP mechanism (Salfeld, nature biotechnology, vol. 25, No 12, 2007; Irani et al. Molecular Immunology, vol. 67, issue 2, part A, 2015). In fact, the fragment crystallisable (Fc) region interacts with a variety of accessory molecules to mediate indirect effector functions such as antibody-dependent cellular cytotoxicity (ADCC), antibody-dependent cellular phagocytosis (ADCP) and complement-dependent cytotoxicity (CDC).

TABLE 3

Examples of a heavy chain constant domain and a light chain constant domain suitable for the antibodies according to the invention.

| | |
|---|---|
| Heavy chain constant domain (IgG4m-S228P) SEQ ID NO: 34 | ASTKGPSVFPLAPCSRSTSE STAALGCLVKDYFPEPVTVS WNSGALTSGVHTFPAVLQSS GLYSLSSVVTVPSSSLGTKT YTCNVDHKPSNTKVDKRVES KYGPPCPPCPAPEFLGGPSV FLFPPKPKDTLMISRTPEVT CVVVDVSQEDPEVQFNWYVD GVEVHNAKTKPREEQFNSTY RVVSVLTVLHQDWLNGKEYK CKVSNKGLPSSIEKTISKAK GQPREPQVYTLPPSQEEMTK NQVSLTCLVKGFYPSDIAVE WESNGQPENNYKTTPPVLDS DGSFFLYSRLTVDKSRWQEG NVFSCSVMHEALHNHYTQKS LSLSPGK |
| Light chain constant domain (CLkappa) SEQ ID NO: 35 | RTVAAPSVFIFPPSDEQLKS GTASVVCLLNNFYPREAKVQ WKVDNALQSGNSQESVTEQD SKDSTYSLSSTLTLSKADYE KHKVYACEVTHQGLSSPVTK SFNRGEC |

In an embodiment, the invention relates to an anti-SIRPa antibody as defined above that comprises:

a heavy chain comprising or consisting of the amino acid sequence SEQ ID NO: 56, and
a light chain comprising or consisting of the amino acid sequence SEQ ID NO: 57,
or
a heavy chain comprising or consisting of the amino acid sequence SEQ ID NO: 36, and
a light chain comprising or consisting of the amino acid sequence SEQ ID NO: 43,
or
a heavy chain comprising or consisting of the amino acid sequence SEQ ID NO: 37, and
a light chain comprising or consisting of the amino acid sequence SEQ ID NO: 44,
or
a heavy chain comprising or consisting of the amino acid sequence SEQ ID NO: 37, and
a light chain comprising or consisting of the amino acid sequence SEQ ID NO: 45,
or
a heavy chain comprising or consisting of the amino acid sequence SEQ ID NO: 38, and
a light chain comprising or consisting of the amino acid sequence SEQ ID NO: 44,
or
a heavy chain comprising or consisting of the amino acid sequence SEQ ID NO: 38, and
a light chain comprising or consisting of the amino acid sequence SEQ ID NO: 45,
or
a heavy chain comprising or consisting of the amino acid sequence SEQ ID NO: 39, and
a light chain comprising or consisting of the amino acid sequence SEQ ID NO: 44,
or
a heavy chain comprising or consisting of the amino acid sequence SEQ ID NO: 39, and
a light chain comprising or consisting of the amino acid sequence SEQ ID NO: 45,
or
a heavy chain comprising or consisting of the amino acid sequence SEQ ID NO: 40, and
a light chain comprising or consisting of the amino acid sequence SEQ ID NO: 44,
or
a heavy chain comprising or consisting of the amino acid sequence SEQ ID NO: 40, and
a light chain comprising or consisting of the amino acid sequence SEQ ID NO: 45,
or
a heavy chain comprising or consisting of the amino acid sequence SEQ ID NO: 41, and
a light chain comprising or consisting of the amino acid sequence SEQ ID NO: 44,
or
a heavy chain comprising or consisting of the amino acid sequence SEQ ID NO: 41, and
a light chain comprising or consisting of the amino acid sequence SEQ ID NO: 45,
or
a heavy chain comprising or consisting of the amino acid sequence SEQ ID NO: 42, and
a light chain comprising or consisting of the amino acid sequence SEQ ID NO: 44,
or
a heavy chain comprising or consisting of the amino acid sequence SEQ ID NO: 42, and
a light chain comprising or consisting of the amino acid sequence SEQ ID NO: 45.

TABLE 4

Heavy chain and light chain sequences of specific antibodies according to the invention.

| | | |
|---|---|---|
| Heavy chain of the wild-type antibody (mouse 18D5) | QVQLQQPGAELVRPG SSVKLSCKASGYTFT SYWVHWVKQRPIQGL EWIGNIDPSDSDTHY NQKFKDKASLTVDKS SSTAYMQLSSLTFED SAVYYCVRGGTGTMA WFAYWGQGTLVTVSA AKTTPPSVYPLAPGC GDTTGSSVTLGCLVK GYFPESVTVTWNSGS LSSSVHTFPALLQSG LYTMSSSVTVPSSTW PSQTVTCSVAHPASS TTVDKKLEPSGPIST INPCPPCKECHKCPA PNLEGGPSVFIFPPN IKDVLMISLTPKVTC VVVDVSEDDPDVQIS WFVNNVEVHTAQTQT HREDYNSTIRVVSTL PIQHQDWMSGKEFKC KVNNKDLPSPIERTI SKIKGLVRAPQVYIL PPPAEQLSRKDVSLT CLWGFNPGDISVEWT SNGHTEENYKDTAPV LDSDGSYFIYSKLNM KTSKWEKTDSFSCNV RHEGLKNYYLKKTIS RSPGK | SEQ ID NO: 56 |
| Heavy chain of the wild-type antibody (chimeric 18D5) | QVQLQQPGAELVRPG SSVKLSCKASGYTFT SYWVHWVKQRPIQGL EWIGNIDPSDSDTHY NQKFKDKASLTVDKS SSTAYMQLSSLTFED SAVYYCVRGGTGTMA WFAYWGQGTLVTVSA ASTKGPSVFPLAPCS RSTSESTAALGCLVK DYFPEPVTVSWNSGA LTSGVHTFPAVLQSS GLYSLSSVVTVPSSS LGTKTYTCNVDHKPS NTKVDKRVESKYGPP CPPCPAPEFLGGPSV FLFPPKPKDTLMISR TPEVTCVVVDVSQED PEVQFNWYVDGVEVH NAKTKPREEQFNSTY RVVSVLTVLHQDWLN GKEYKCKVSNKGLPS SIEKTISKAKGQPRE PQVYTLPPSQEEMTK NQVSLTCLVKGFYPS DIAVEWESNGQPENN YKTTPPVLDSDGSFF LYSRLTVDKSRWQEG NVFSCSVMHEALHNH YTQKSLSLSPGK | SEQ ID NO: 36 |
| Heavy chain of humanized variant (HA) | EVQLVQSGAEVKKPG ESLRISCKASGYTFT SYWVHWVRQMPGKGL EWIGNIDPSDSDTHY NQKFKDHVTLSVDKS ISTAYLQLSSLKASD TAMYYCVRGGTGTMA | SEQ ID NO: 37 |

TABLE 4-continued

Heavy chain and light chain sequences of specific antibodies according to the invention.

| | | |
|---|---|---|
| | WFAYWGQGTLVTVSS<br>ASTKGPSVFPLAPCS<br>RSTSESTAALGCLVK<br>DYFPEPVTVSWNSGA<br>LTSGVHTFPAVLQSS<br>GLYSLSSVVTVPSSS<br>LGTKTYTCNVDHKPS<br>NTKVDKRVESKYGPP<br>CPPCPAPEFLGGPSV<br>FLFPPKPKDTLMISR<br>TPEVTCVVVDVSQED<br>PEVQFNWYVDGVEVH<br>NAKTKPREEQFNSTY<br>RVVSVLTVLHQDWLN<br>GKEYKCKVSNKGLPS<br>SIEKTISKAKGQPRE<br>PQVYTLPPSQEEMTK<br>NQVSLTCLVKGFYPS<br>DIAVEWESNGQPENN<br>YKTTPPVLDSDGSFF<br>LYSRLTVDKSRWQEG<br>NVFSCSVMHEALHNH<br>YTQKSLSLSPGK | |
| Heavy chain of humanized variant (HB) | EVQLVQSGAEVKKPG<br>ESLRISCKASGYSFT<br>SYWVHWVRQMPGKGL<br>EWMGNIDPSDSDTHY<br>NQKFKDHVTLSVDKS<br>ISTAYLQLSSLKASD<br>TAMYYCVRGGTGTMA<br>WFAYWGQGTLVTVSS<br>ASTKGPSVFPLAPCS<br>RSTSESTAALGCLVK<br>DYFPEPVTVSWNSGA<br>LTSGVHTFPAVLQSS<br>GLYSLSSVVTVPSSS<br>LGTKTYTCNVDHKPS<br>NTKVDKRVESKYGPP<br>CPPCPAPEFLGGPSV<br>FLFPPKPKDTLMISR<br>TPEVTCVVVDVSQED<br>PEVQFNWYVDGVEVH<br>NAKTKPREEQFNSTY<br>RVVSVLTVLHQDWLN<br>GKEYKCKVSNKGLPS<br>SIEKTISKAKGQPRE<br>PQVYTLPPSQEEMTK<br>NQVSLTCLVKGFYPS<br>DIAVEWESNGQPENN<br>YKTTPPVLDSDGSFF<br>LYSRLTVDKSRWQEG<br>NVFSCSVMHEALHNH<br>YTQKSLSLSPGK | SEQ ID NO: 38 |
| Heavy chain of humanized variant (HC) | EVQLVQSGAEVKKPG<br>ESLRISCKASGYSFT<br>SYWVHWVRQMPGKGL<br>EWMGNIDPSDSDTHY<br>SPSFQGHVTLSVDKS<br>ISTAYLQLSSLKASD<br>TAMYYCVRGGTGTMA<br>WFAYWGQGTLVTVSS<br>ASTKGPSVFPLAPCS<br>RSTSESTAALGCLVK<br>DYFPEPVTVSWNSGA<br>LTSGVHTFPAVLQSS<br>GLYSLSSVVTVPSSS<br>LGTKTYTCNVDHKPS<br>NTKVDKRVESKYGPP<br>CPPCPAPEFLGGPSV<br>FLFPPKPKDTLMISR<br>TPEVTCVVVDVSQED<br>PEVQFNWYVDGVEVH<br>NAKTKPREEQFNSTY<br>RVVSVLTVLHQDWLN<br>GKEYKCKVSNKGLPS<br>SIEKTISKAKGQPRE<br>PQVYTLPPSQEEMTK<br>NQVSLTCLVKGFYPS<br>DIAVEWESNGQPENN<br>YKTTPPVLDSDGSFF<br>LYSRLTVDKSRWQEG<br>NVFSCSVMHEALHNH<br>YTQKSLSLSPGK | SEQ ID NO: 39 |
| Heavy chain of humanized variant (HE) | EVQLVQSGAEVKKPG<br>ESLRISCKASGYSFT<br>SYWVHWVRQMPGKGL<br>EWMGNIDPSDSDTHY<br>SPSFQGHVTLSVDKS<br>ISTAYLQLSSLKASD<br>TAMYYCVRGGTGTLA<br>WFAYWGQGTLVTVSS<br>ASTKGPSVFPLAPCS<br>RSTSESTAALGCLVK<br>DYFPEPVTVSWNSGA<br>LTSGVHTFPAVLQSS<br>GLYSLSSVVTVPSSS<br>LGTKTYTCNVDHKPS<br>NTKVDKRVESKYGPP<br>CPPCPAPEFLGGPSV<br>FLFPPKPKDTLMISR<br>TPEVTCVVVDVSQED<br>PEVQFNWYVDGVEVH<br>NAKTKPREEQFNSTY<br>RVVSVLTVLHQDWLN<br>GKEYKCKVSNKGLPS<br>SIEKTISKAKGQPRE<br>PQVYTLPPSQEEMTK<br>NQVSLTCLVKGFYPS<br>DIAVEWESNGQPENN<br>YKTTPPVLDSDGSFF<br>LYSRLTVDKSRWQEG<br>NVFSCSVMHEALHNH<br>YTQKSLSLSPGK | SEQ ID NO: 40 |
| Heavy chain of humanized variant (HF) | EVQLVQSGAEVKKPG<br>ESLRISCKASGYSFT<br>SYWVHWVRQMPGKGL<br>EWMGNIDPSDSDTHY<br>SPSFQGHVTLSVDKS<br>ISTAYLQLSSLKASD<br>TAMYYCVRGGTGTMA<br>YFAYWGQGTLVTVSS<br>ASTKGPSVFPLAPCS<br>RSTSESTAALGCLVK<br>DYFPEPVTVSWNSGA<br>LTSGVHTFPAVLQSS<br>GLYSLSSVVTVPSSS<br>LGTKTYTCNVDHKPS<br>NTKVDKRVESKYGPP<br>CPPCPAPEFLGGPSV<br>FLFPPKPKDTLMISR<br>TPEVTCVVVDVSQED<br>PEVQFNWYVDGVEVH<br>NAKTKPREEQFNSTY<br>RVVSVLTVLHQDWLN<br>GKEYKCKVSNKGLPS<br>SIEKTISKAKGQPRE<br>PQVYTLPPSQEEMTK<br>NQVSLTCLVKGFYPS<br>DIAVEWESNGQPENN<br>YKTTPPVLDSDGSFF<br>LYSRLTVDKSRWQEG<br>NVFSCSVMHEALHNH<br>YTQKSLSLSPGK | SEQ ID NO: 41 |
| Heavy chain of humanized | EVQLVQSGAEVKKPG<br>ESLRISCKASGYSFT<br>SYWVHWVRQMPGKGL | SEQ ID NO: 42 |

TABLE 4-continued

Heavy chain and light chain sequences of specific antibodies according to the invention.

| | | |
|---|---|---|
| variant (HEF) | EWMGNIDPSDSDTHY SPSFQGHVTLSVDKS ISTAYLQLSSLKASD TAMYYCVRGGTGTLA YFAYWGQGTLVTVSS ASTKGPSVFPLAPCS RSTSESTAALGCLVK DYFPEPVTVSWNSGA LTSGVHTFPAVLQSS GLYSLSSVVTVPSSS LGTKTYTCNVDHKPS NTKVDKRVESKYGPP CPPCPAPEFLGGPSV FLFPPKPKDTLMISR TPEVTCVVVDVSQED PEVQFNWYVDGVEVH NAKTKPREEQFNSTY RVVSVLTVLHQDWLN GKEYKCKVSNKGLPS SIEKTISKAKGQPRE PQVYTLPPSQEEMTK NQVSLTCLVKGFYPS DIAVEWESNGQPENN YKTTPPVLDSDGSFF LYSRLTVDKSRWQEG NVFSCSVMHEALHNH YTQKSLSLSPGK | |
| Light chain of the wild-type antibody (mouse 18D5) | DVVMTQTPLSLPVSL GDQASISCRSSQSLV HSYGNTYLYWYLQKP GQSPKLLIYRVSNRF SGVPDRFSGSGSGTD FTLKISRVEAEDLGV YFCFQGTHVPYTFGS GTKLEIKRADAAPTV SIFPPSSEQLTSGGA SVVCFLNNFYPKDIN VKWKIDGSERQNGVL NSWTDQDSKDSTYSM SSTLTLTKDEYERHN SYTCEATHKTSTSPI VKSFNRNEC | SEQ ID NO: 57 |
| Light chain of the wild-type antibody (chimeric 18D5) | DVVMTQTPLSLPVSL GDQASISCRSSQSLV HSYGNTYLYWYLQKP GQSPKLLIYRVSNRF SGVPDRFSGSGSGTD FTLKISRVEAEDLGV YFCFQGTHVPYTFGS GTKLEIKRTVAAPSV FIFP PSDEQLKSGTASVVC LLNNFYPREAKVQWK VDNALQSGNSQESVT EQDSKDSTYSLSSTL TLSKADYEKHKVYAC EVTHQGLSSPVTKSF NRGEC | SEQ ID NO: 43 |
| Light chain variable domain of humanized variant A (LA) | DVVMTQSPLSLPVTLG QPASISCRSSQSLVH SYGNTYLYWYSQQRP GQSPRLLIYRVSNRF SGVPDRFSGSGSGTD FTLKISRVEAEDVGV YFCFQGTHVPYTFGG GTKVEIKRTVAAPSV FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC | SEQ ID NO: 44 |
| Light chain variable domain of humanized variant (LB) | DVVMTQSPLSLPVTL GQPASISCRSSQSLV HSYGNTYLYWFQQRP GQSPRLLIYRVSNRF SGVPDRFSGSGSGTD FTLKISRVEAEDVGV YYCFQGTHVPYTFGG GTKVEIKRTVAAPSV FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC | SEQ ID NO: 45 |

In an embodiment, the invention relates to an anti-SIRPa antibody or antigen-binding fragment thereof or antigen-binding antibody mimetic as defined above that is able to induce the differentiation of monocytic myeloid-derived suppressor cells (Mo-MDSC) into non suppressive cells.

In an embodiment, the invention relates to an anti-SIRPa antibody or antigen-binding fragment thereof or antigen-binding antibody mimetic as defined above, wherein said non suppressive cells secrete pro-inflammatory cytokines such as IL6, IL12 and TNF, and no or low level of anti-inflammatory cytokines such as IL10 and TGFβ.

In an embodiment, the invention relates to an anti-SIRPa antibody or antigen-binding fragment thereof or antigen-binding antibody mimetic as defined above, wherein said non suppressive cells express iNOS.

In an embodiment, the invention relates to an anti-SIRPa antibody or antigen-binding fragment thereof or antigen-binding antibody mimetic as defined above, wherein said non suppressive cells do not express the MHC Class II markers and express the markers CD80-CD86.

In an embodiment, the invention relates to an anti-SIRPa antibody or antigen-binding fragment thereof or antigen-binding antibody mimetic as defined above, wherein said non suppressive cells express at least one marker of the natural killer (NK) cells.

In an embodiment, the invention relates to an anti-SIRPa antibody or antigen-binding fragment thereof or antigen-binding antibody mimetic as defined above, wherein said antibody or antigen-binding fragment thereof is able to inhibit M2 polarization of macrophages and/or favors pro-inflammatory M1-type macrophages.

The antibodies of the invention can modify the macrophage polarization in order to induce a pro-inflammatory environment, i.e. they can inhibit the anti-inflammatory signal provided by M2-type macrophages and/or favor the pro-inflammatory signal provided by M1-type macrophages This approach allows to reestablish an inflammatory environment favorable to the action of the T effector cells, in particular in eliminating the cancer cells.

SIRPa Antibodies

The embodiments recited for the antibodies as defined above are repeated mutadis mutandis to the antibodies recited in the other aspects of the invention.

In another aspect, the invention relates to an anti-SIRPa antibody or antigen-binding fragment thereof or antigen-binding antibody mimetic that specifically binds to a conformational epitope comprising at least one peptide selected from the group consisting of SEQ ID NO: 70 (ELIYNQKEGHFPR), SEQ ID NO: 71 (RNNMDFSIRIGN) and SEQ ID NO: 72 (SPRDITLKW) within SIRPa.

In another aspect, the invention relates to an anti-SIRPa antibody or antigen-binding fragment thereof or antigen-binding antibody mimetic that specifically binds to a conformational epitope comprising or consisting of the peptides of SEQ ID NO: 70 (ELIYNQKEGHFPR), SEQ ID NO: 71 (RNNMDFSIRIGN) and SEQ ID NO: 72 (SPRDITLKW) within SIRPa.

In another aspect, the invention relates to an anti-SIRPa antibody or antigen-binding fragment thereof or antigen-binding antibody mimetic that specifically binds to a conformational epitope comprising at least one peptide selected from the group consisting of SEQ ID NO: 70 (ELIYNQKEGHFPR) and SEQ ID NO: 71 (RNNMDFSIRIGN).

In another aspect, the invention relates to an anti-SIRPa antibody or antigen-binding fragment thereof or antigen-binding antibody mimetic that specifically binds to a conformational epitope comprising or consisting of the peptides of SEQ ID NO: 70 (ELIYNQKEGHFPR) and SEQ ID NO: 71 (RNNMDFSIRIGN) within SIRPa.

In another aspect, the invention relates to an anti-SIRPa antibody or antigen-binding fragment thereof or antigen-binding antibody mimetic that specifically binds to a conformational epitope comprising at least one peptide selected from the group consisting of SEQ ID NO: 73 (YNQK) and SIR.

In another aspect, the invention relates to an anti-SIRPa antibody or antigen-binding fragment thereof or antigen-binding antibody mimetic that specifically binds to a conformational epitope comprising or consisting of the peptides of SEQ ID NO: 73 (YNQK) and SIR within SIRPa.

In another aspect, the invention relates to an anti-SIRPa antibody or antigen-binding fragment thereof or antigen-binding antibody mimetic that comprises:
  a) a heavy chain comprising HCDR1, HCDR2 and HCDR3, and/or
  b) a light chain comprising LCDR1, LCDR2 and LCDR3,
  wherein said CDRs are defined as follows:
  HCDR1 comprising or consisting of a peptide of the amino acid sequence SEQ ID NO: 14 (SYWVH),
  HCDR2 comprising or consisting of a peptide of the amino acid sequence SEQ ID NO: 15 (NIDPSDSDTHYNQKFKD) or SEQ ID NO: 16 (NIDPSDSDTHYSPSFQG),
  HCDR3 comprising or consisting of a peptide of the amino acid sequence SEQ ID NO: 17 (GGTGTMAWFAY), SEQ ID NO: 18 (GGTGTLAWFAY), SEQ ID NO: 19 (GGTGTMAYFAY) or SEQ ID NO: 20 (GGTGTLAYFAY),
  LCDR1 comprising or consisting of a peptide of the amino acid sequence SEQ ID NO: 21 (RSSQSLVHSYGNTYLY),
  LCDR2 comprising or consisting of a peptide of the amino acid sequence SEQ ID NO: 22 (RVSNRFS), and
  LCDR3 comprising or consisting of a peptide of the amino acid sequence SEQ ID NO: 23 (FQGTHVPYT).

The invention also relates to an anti-SIRPa antibody or antigen-binding fragment thereof or antigen-binding antibody mimetic which inhibits the binding of CD47 to SIRPa and which does not bind specifically to SIRPg and/or which does not bind specifically to T-cells and/or which does not inhibit the proliferation of T-cells and/or which does not inhibit the binding of CD47 to SIRPg, in particular which inhibits the binding of CD47 to SIRPa and which does not bind specifically to SIRPg and which does not bind specifically to T-cells and which does not inhibit the proliferation of T-cells and which does not inhibit the binding of CD47 to SIRPg.

Applications

In another aspect, the invention relates to:
  an anti-SIRPa antibody or antigen-binding fragment thereof or antigen-binding antibody mimetic as defined above, or
  an anti-SIRPa antibody or antigen-binding fragment thereof or antigen-binding antibody mimetic which inhibits the binding of CD47 to SIRPa and which does not bind specifically to SIRPg and/or which does not bind specifically to T-cells and/or which does not inhibit the proliferation of T-cells and/or which does not inhibit the binding of CD47 to SIRPg,
  in particular, which inhibits the binding of CD47 to SIRPa and which does not bind specifically to SIRPg and which does not bind specifically to T-cells and which does not inhibit the proliferation of T-cells and which does not inhibit the binding of CD47 to SIRPg.
  for use as a medicament.

The present invention also relates to a method of treatment in a subject in need thereof comprising administering to said subject an effective amount of:
  an anti-SIRPa antibody or antigen-binding fragment thereof or antigen-binding antibody mimetic as defined above, or
  an anti-SIRPa antibody or antigen-binding fragment thereof or antigen-binding antibody mimetic, which inhibits the binding of CD47 to SIRPa and which does not bind specifically to SIRPg and/or which does not bind specifically to T-cells and/or which does not inhibit the proliferation of T-cells and/or which does not inhibit the binding of CD47 to SIRPg,
  in particular, which inhibits the binding of CD47 to SIRPa and which does not bind specifically to SIRPg and which does not bind specifically to T-cells and which does not inhibit the proliferation of T-cells and which does not inhibit the binding of CD47 to SIRPg.

The present invention also relates to the use of:
  an anti-SIRPa antibody or antigen-binding fragment thereof or antigen-binding antibody mimetic as defined above, or
  an anti-SIRPa antibody or antigen-binding fragment thereof or antigen-binding antibody mimetic, which inhibits the binding of CD47 to SIRPa and which does not bind specifically to SIRPg and/or which does not bind specifically to T-cells and/or which does not inhibit the proliferation of T-cells and/or which does not inhibit the binding of CD47 to SIRPg,
  in particular, which inhibits the binding of CD47 to SIRPa and which does not bind specifically to SIRPg and which does not bind specifically to T-cells and which does not inhibit the proliferation of T-cells and which does not inhibit the binding of CD47 to SIRPg,
  in the manufacture of a medicament.

In another aspect, the invention relates to:
  an anti-SIRPa antibody or antigen-binding fragment thereof or antigen-binding antibody mimetic as defined above, or
  an anti-SIRPa antibody or antigen-binding fragment thereof or antigen-binding antibody mimetic, which inhibits the binding of CD47 to SIRPa and which does not bind specifically to SIRPg and/or which does not bind specifically to T-cells and/or which does not inhibit the proliferation of T-cells and/or which does not inhibit the binding of CD47 to SIRPg, in particular, which inhibits the binding of CD47 to SIRPa and which does not bind specifically to SIRPg and which does not bind specifically to T-cells and which does not inhibit the proliferation of T-cells and which does not inhibit the binding of CD47 to SIRPg, for use in the treatment of any condition susceptible of being improved or prevented by differentiating monocytic myeloid-derived suppressor cells (Mo-MDSC) into non suppressive cells.

As defined herein, "a condition susceptible of being improved or prevented by differentiating monocytic myeloid-derived suppressor cells (Mo-MDSC) into non suppressive cells" corresponds to a cancer including inflammatory cancers and cancers with infiltrated myeloid cells (in particular with infiltrated MDSCs and/or TAM cells), an infectious disease, a trauma, an auto-immune disease (such as rheumatoid arthritis, type 1 diabetes, lupus, psoriasis), a vaccination, a chronic inflammatory diseases (such as Inflammatory bowel diseases including Crohn disease and Ulcerative colitis), a septic shock, a chronic infectious disease (such as with Pseudomonas or CMV), fibrosis, atherosclerosis or a transplant dysfunctions.

The present invention also relates to a method of treatment of any condition susceptible of being improved or prevented by differentiating monocytic myeloid-derived suppressor cells (Mo-MDSC) into non suppressive cells in a subject in need thereof comprising administering to said subject an effective amount of:
- an anti-SIRPa antibody or antigen-binding fragment thereof or antigen-binding antibody mimetic as defined above, or
- an anti-SIRPa antibody or antigen-binding fragment thereof or antigen-binding antibody mimetic, which inhibits the binding of CD47 to SIRPa and which does not bind specifically to SIRPg and/or which does not bind specifically to T-cells and/or which does not inhibit the proliferation of T-cells and/or which does not inhibit the binding of CD47 to SIRPg, in particular, which inhibits the binding of CD47 to SIRPa and which does not bind specifically to SIRPg and which does not bind specifically to T-cells and which does not inhibit the proliferation of T-cells and which does not inhibit the binding of CD47 to SIRPg.

The present invention also relates to the use of:
- an anti-SIRPa antibody or antigen-binding fragment thereof or antigen-binding antibody mimetic as defined above, or
- an anti-SIRPa antibody or antigen-binding fragment thereof or antigen-binding antibody mimetic, which inhibits the binding of CD47 to SIRPa and which does not bind specifically to SIRPg and/or which does not bind specifically to T-cells and/or which does not inhibit the proliferation of T-cells and/or which does not inhibit the binding of CD47 to SIRPg, in particular, which inhibits the binding of CD47 to SIRPa and which does not bind specifically to SIRPg and which does not bind specifically to T-cells and which does not inhibit the proliferation of T-cells and which does not inhibit the binding of CD47 to SIRPg, in the manufacture of a medicament for the treatment of any condition susceptible of being improved or prevented by differentiating monocytic myeloid-derived suppressor cells (Mo-MDSC) into non suppressive cells.

In an embodiment, the invention relates to:
- an anti-SIRPa antibody or antigen-binding fragment thereof or antigen-binding antibody mimetic as defined above, or
- an anti-SIRPa antibody or antigen-binding fragment thereof or antigen-binding antibody mimetic, which inhibits the binding of CD47 to SIRPa and which does not bind specifically to SIRPg and/or which does not bind specifically to T-cells and/or which does not inhibit the proliferation of T-cells and/or which does not inhibit the binding of CD47 to SIRPg, in particular, which inhibits the binding of CD47 to SIRPa and which does not bind specifically to SIRPg and which does not bind specifically to T-cells and which does not inhibit the proliferation of T-cells and which does not inhibit the binding of CD47 to SIRPg, for use in the treatment of any condition susceptible of being improved or prevented by modifying macrophage polarization to pro-inflammatory macrophages.

Indeed, SIRPa acts as a checkpoint inhibitor and participates to macrophage polarization. In particular, blocking SIRPa induces a pro-inflammatory function of macrophages associated to type 1 macrophages (M1 pro-inflammatory=M (IFNg)) and inhibits the suppressive activity of macrophages in the tumor, since the pro-inflammatory profile of macrophages is obtained at the expense of type 2 macrophages (M2 type high phagocytic activity=M (IL4)). Thus, an antagonist of SIRPa is able to inhibit M2 phenotypic polarization of macrophages and/or favors pro-inflammatory M1-type macrophage function and can be used in therapeutic.

As defined herein, "a condition susceptible of being improved or prevented by modifying macrophage polarization to favor pro-inflammatory macrophages" corresponds for example to a solid cancer, a liquid cancer, an infectious disease, a trauma, an auto-immune disease, a vaccination, a brain injury, a nerve injury, a polycythemia, a hemochromatosis or a chronic inflammatory disease.

The present invention also relates to a method of treatment of any condition susceptible of being improved or prevented by modifying macrophage polarization to pro-inflammatory macrophages in a subject in need thereof comprising administering to said subject an effective amount of:
- an anti-SIRPa antibody or antigen-binding fragment thereof or antigen-binding antibody mimetic as defined above, or
- an anti-SIRPa antibody or antigen-binding fragment thereof or antigen-binding antibody mimetic, which inhibits the binding of CD47 to SIRPa and which does not bind specifically to SIRPg and/or which does not bind specifically to T-cells and/or which does not inhibit the proliferation of T-cells and/or which does not inhibit the binding of CD47 to SIRPg, in particular, which inhibits the binding of CD47 to SIRPa and which does not bind specifically to SIRPg and which does not bind specifically to T-cells and which does not inhibit the proliferation of T-cells and which does not inhibit the binding of CD47 to SIRPg.

In an embodiment, the invention also relates to the use of:
- an anti-SIRPa antibody or antigen-binding fragment thereof or antigen-binding antibody mimetic as defined above, or
- an anti-SIRPa antibody or antigen-binding fragment thereof or antigen-binding antibody mimetic, which inhibits the binding of CD47 to SIRPa and which does not bind specifically to SIRPg and/or which does not bind specifically to T-cells and/or which does not inhibit the proliferation of T-cells and/or which does not inhibit the binding of CD47 to SIRPg, in particular, which inhibits the binding of CD47 to SIRPa and which does not bind specifically to SIRPg and which does not bind specifically to T-cells and which does not inhibit the proliferation of T-cells and which does not inhibit the binding of CD47 to SIRPg, in the manufacture of a medicament for the treatment of any condition susceptible of being improved or prevented by modifying macrophage polarization to pro-inflammatory macrophages.

Modifying the polarization of macrophages to favor pro-inflammatory cells can be useful in a number of pathologies or situations. As described above, this modification is particularly useful in the context of cancers, to restore an anti-tumor activity of macrophages and/or prevent the pro-tumoral activity of M2-type macrophages. Inappropriate immune responses due to an excess of M2-type macrophage polarization also occur in infectious diseases, fibrosis, vaccination, trauma and chronic inflammatory diseases.

Thus, according to a particular embodiment, anti-SIRPa antibody can be used to treat an individual who has a cancer selected from the group consisting of lung cancers, mesothelioma cancers, ovary cancers, liver cancers, bladder cancers, brain cancers, breast cancers, colon cancers, sarcomas, pancreas cancers, head and neck cancers, kidney cancers, thymomas, gliomas, melanomas and hematologic cancers such as lymphomas (Hodgkin's lymphoma and non-Hodgkin's lymphoma), leukemias such as T and B Acute or Chronic Lymphoblastic Leukemia (ALL or CLL) or Acute or Chronic myeloid leukemia (AML or CML) and Myelomas.

In an embodiment, the invention relates to:
an anti-SIRPa antibody or antigen-binding fragment thereof or antigen-binding antibody mimetic as defined above, or
an anti-SIRPa antibody or antigen-binding fragment thereof or antigen-binding antibody mimetic, which inhibits the binding of CD47 to SIRPa and which does not bind specifically to SIRPg and/or which does not bind specifically to T-cells and/or which does not inhibit the proliferation of T-cells and/or which does not inhibit the binding of CD47 to SIRPg,
in particular, which inhibits the binding of CD47 to SIRPa and which does not bind specifically to SIRPg and which does not bind specifically to T-cells and which does not inhibit the proliferation of T-cells and which does not inhibit the binding of CD47 to SIRPg,
for use in the treatment of a pathology selected from the group consisting of a cancer (in particular inflammatory cancers and cancers with infiltrated myeloid cells particularly with infiltrated MDSCs and/or TAM cells), an infectious disease, a chronic inflammatory disease, an auto-immune disease, a neurologic disease, a brain injury, a nerve injury, a polycythemia, a hemochromatosis, a trauma, a septic shock, a chronic infectious disease (such as with Pseudomonas or CMV), fibrosis, atherosclerosis, obesity, type II diabetes and a transplant dysfunction.

In an embodiment, the invention relates to a method of treatment of a pathology selected from the group consisting of a cancer (in particular inflammatory cancers and cancers with infiltrated myeloid cells particularly with infiltrated MDSCs and/or TAM cells), an infectious disease, a chronic inflammatory disease, an auto-immune disease, a neurologic disease, a brain injury, a nerve injury, a polycythemia, a hemochromatosis, a trauma, a septic shock, a chronic infectious disease (such as with *Pseudomonas* or CMV), fibrosis, atherosclerosis, obesity, type II diabetes and a transplant dysfunction in a subject in need thereof comprising administering to said subject an effective amount of:
an anti-SIRPa antibody or antigen-binding fragment thereof or antigen-binding antibody mimetic as defined above, or
an anti-SIRPa antibody or antigen-binding fragment thereof or antigen-binding antibody mimetic, which inhibits the binding of CD47 to SIRPa and which does not bind specifically to SIRPg and/or which does not bind specifically to T-cells and/or which does not inhibit the proliferation of T-cells and/or which does not inhibit the binding of CD47 to SIRPg,
in particular, which inhibits the binding of CD47 to SIRPa and which does not bind specifically to SIRPg and which does not bind specifically to T-cells and which does not inhibit the proliferation of T-cells and which does not inhibit the binding of CD47 to SIRPg.

In an embodiment, the invention relates to the use of:
an anti-SIRPa antibody or antigen-binding fragment thereof or antigen-binding antibody mimetic as defined above, or
an anti-SIRPa antibody or antigen-binding fragment thereof or antigen-binding antibody mimetic, which inhibits the binding of CD47 to SIRPa and which does not bind specifically to SIRPg and/or which does not bind specifically to T-cells and/or which does not inhibit the proliferation of T-cells and/or which does not inhibit the binding of CD47 to SIRPg,
in particular, which inhibits the binding of CD47 to SIRPa and which does not bind specifically to SIRPg and which does not bind specifically to T-cells and which does not inhibit the proliferation of T-cells and which does not inhibit the binding of CD47 to SIRPg,
in the manufacture of a medicament for the treatment of a pathology selected from the group consisting of a cancer (in particular inflammatory cancers and cancers with infiltrated myeloid cells particularly with infiltrated MDSCs and/or TAM cells), an infectious disease, a chronic inflammatory disease, an auto-immune disease, a neurologic disease, a brain injury, a nerve injury, a polycythemia, a hemochromatosis, a trauma, a septic shock, a chronic infectious disease (such as with *Pseudomonas* or CMV), fibrosis, atherosclerosis, obesity, type II diabetes and a transplant dysfunction.

In an embodiment, the invention relates to an anti-human SIRPa antibody or antigen-binding fragment thereof or antigen-binding antibody mimetic as defined above, for its uses as defined above, wherein said anti-human SIRPa antibody or antigen-binding fragment thereof or antigen-binding antibody mimetic of the invention is administered to a patient presenting a SIRPa-positive tumor.

In an embodiment, the invention relates to:
an anti-SIRPa antibody or antigen-binding fragment thereof or antigen-binding antibody mimetic as defined above, or
an anti-SIRPa antibody or antigen-binding fragment thereof or antigen-binding antibody mimetic which inhibits the binding of CD47 to SIRPa and which does not bind specifically to SIRPg and/or which does not bind specifically to T-cells and/or which does not inhibit the proliferation of T-cells and/or which does not inhibit the binding of CD47 to SIRPg,
in particular, which inhibits the binding of CD47 to SIRPa and which does not bind specifically to SIRPg and which does not bind specifically to T-cells and which does not inhibit the proliferation of T-cells and which does not inhibit the binding of CD47 to SIRPg, for use in vaccination.

In an embodiment, the invention relates to a method of vaccination of a subject comprising administering to said subject an effective amount of:

an anti-SIRPa antibody or antigen-binding fragment thereof or antigen-binding antibody mimetic as defined above, or an anti-SIRPa antibody or antigen-binding fragment thereof or antigen-binding antibody mimetic which inhibits the binding of CD47 to SIRPa and which does not bind specifically to SIRPg and/or which does not bind specifically to T-cells and/or which does not inhibit the proliferation of T-cells and/or which does not inhibit the binding of CD47 to SIRPg, in particular, which inhibits the binding of CD47 to SIRPa and which does not bind specifically to SIRPg and which does not bind specifically to T-cells and which does not inhibit the proliferation of T-cells and which does not inhibit the binding of CD47 to SIRPg.

In an embodiment, the invention relates to the use of:

an anti-SIRPa antibody or antigen-binding fragment thereof or antigen-binding antibody mimetic as defined above, or an anti-SIRPa antibody or antigen-binding fragment thereof or antigen-binding antibody mimetic which inhibits the binding of CD47 to SIRPa and which does not bind specifically to SIRPg and/or which does not bind specifically to T-cells and/or which does not inhibit the proliferation of T-cells and/or which does not inhibit the binding of CD47 to SIRPg, in particular, which inhibits the binding of CD47 to SIRPa and which does not bind specifically to SIRPg and which does not bind specifically to T-cells and which does not inhibit the proliferation of T-cells and which does not inhibit the binding of CD47 to SIRPg, for the manufacture of a vaccine.

Suppressive myeloid cells limit the effectiveness of vaccination, especially in young children. Thus, an anti-SIRPa/g would limit the benefit provided by an anti-SIRPa on the vaccine response, preventing T lymphocytes from responding to vaccination.

The antibody or antigen-binding fragment thereof of the invention can be administered in a variety of suitable routes, e.g., intravenously (IV), subcutaneously (SC), or, intramuscularly (IM) to the subject.

The antibody or antigen-binding fragment thereof can be administered alone or in combination with another therapeutic agent, e.g., a second human monoclonal antibody or antigen binding fragment thereof. In another example, the antibody is administered together with another agent, for example, an immunosuppressive agent, an erythropoiesis-stimulating agent (ESA), in combination with therapeutic cell compositions, and the like.

In an embodiment, the invention relates to an anti-SIRPa antibody or antigen-binding fragment thereof or antigen-binding antibody mimetic for its use as defined above, wherein the anti-SIRPa antibody or antigen-binding fragment is combined with a second therapeutic agent.

In particular, anti-SIRPa antibodies of the present invention can be combined with some other potential strategies for overcoming tumor immune evasion mechanisms with agents in clinical development or already on the market (see table 1 from Antonia et al. Immuno-oncology combinations: a review of clinical experience and future prospects. Clin. Cancer Res. Off. J. Am. Assoc. Cancer Res. 20, 6258-6268, 2014):

1—Reversing the inhibition of adaptive immunity (blocking T-cell checkpoint pathways), for example by using an anti-CTLA4, an anti-PD1 or an anti-PD-L1 molecule;

2—Switching on adaptive immunity (promoting T-cell costimulatory receptor signaling using agonist molecules, in particular antibodies), for example by targeting CD137 (4-1BB) using agonist molecules including agonist anti-CD137 (anti-4-1BB) antibodies or CD137 (4-1BB) ligands;

3—Improving the function of innate immune cells;

4—Activating the immune system (potentiating immune-cell effector function), for example through vaccine-based strategies.

The administration of the second therapeutic agent can be simultaneous or not with the administration of the anti-SIRPa antibody. Depending on the nature of the second agent, a co-administration can be prepared in the form of a combination drug (product), also known as a "combo". A combo is a fixed-dose combination that includes two or more active pharmaceutical ingredients combined in a single dosage form, which is manufactured and distributed in fixed doses. But the dose regimen and/or the administration route can also differ.

In a preferred embodiment, this second therapeutic agent is selected from the group consisting of chemotherapeutic agents, radiotherapy agents, immunotherapeutic agents, cell therapy agents (such as CAR-T cells), antibiotics and probiotics.

In particular, immunotherapeutic agents useful in the context of the invention are selected from the group consisting of therapeutic vaccines (DNA, RNA or peptide vaccins), immune checkpoint blockers or activators, in particular of adaptive immune cells (T or B lymphocytes) or immunoconjugates such as antibody-drug conjugates.

As used herein, the term "immunotherapeutic agents" refers in particular to agents that could take cancer vaccines from interesting biological phenomena to effective therapeutic agents including: T-cell growth factors to increase number and repertoire of naïve T cells, growth factors to increase the number of dendritic cells (DCs), agonists to activate DCs and other antigen-pre senting cells (APCs), adjuvants to allow and augment cancer vaccines, agonists to activate and stimulate T cells, inhibitors of T-cell checkpoint blockade, T-cell growth factors to increase the growth and survival of immune T cells, agents to inhibit, block, or neutralize cancer cell and immune cell-derived immunosuppressive cytokine.

Numerous immune checkpoint blocker or activator are known in the art. In the context of the invention, examples of immune checkpoint blockers or activators of adaptive immune cells (B or T lymphocytes) that could be useful are anti-PDL1, anti-PD1, anti-CTLA4, anti-CD137, anti-CD2, anti-CD28, anti-CD40, anti-HVEM, anti-BTLA, anti-CD160, anti-TIGIT, anti-TIM-1/3, anti-LAG-3, anti-2B4, and anti-OX40, anti-CD40 agonist, CD40-L, TLR agonists, anti-ICOS, ICOS-L and B-cell receptor agonists, in particular anti-PDL1, anti-PD1, anti-CD137.

Said immunotherapeutic agent can also be an antibody targeting tumoral antigen, particularly selected from the group consisting of anti-Her2, anti-EGFR, anti-CD20, anti-CD19, anti-CD52.

The antibody may be provided at an effective dose from about 1 ng/kg body weight to about 30 mg/kg body weight, or more. In specific embodiments, the dosage may range from 1 µg/kg to about 20 mg/kg, optionally from 10 µg/kg up to 10 mg/kg or from 100 µg/kg up to 5 mg/kg.

The term "effective dose" or "effective dosage" or "effective amount" is defined as an amount sufficient to achieve or at least partially achieve the desired effect. The term "effective dose" is meant to encompass an amount sufficient to cure or at least partially arrest the disease and its complications in a patient already suffering from the disease. Amounts or doses effective for this use will depend on the condition to be treated, the delivered antibody construct, the therapeutic context and objectives, the severity of the disease, prior therapy, the patient's clinical history and response to the therapeutic agent, the route of administration, the size (body weight, body surface or organ size) and/or condition (the age and general health) of the patient, and the general state of the patient's own immune system. The proper dose can be adjusted such that it can be administered to the patient once or over a series of administrations, and in order to obtain the optimal therapeutic effect.

Dosing for such purposes may be repeated as required, e.g. daily, semi-weekly, weekly, semi-monthly, monthly, or as required during relapses.

In an aspect, the invention also relates to:
- an anti-SIRPa antibody or antigen-binding fragment thereof or antigen-binding antibody mimetic as defined above, or
- an anti-SIRPa antibody or antigen-binding fragment thereof or antigen-binding antibody mimetic which inhibits the binding of CD47 to SIRPa and which does not bind specifically to SIRPg and/or which does not bind specifically to T-cells and/or which does not inhibit the proliferation of T-cells and/or which does not inhibit the binding of CD47 to SIRPg, in particular, which inhibits the binding of CD47 to SIRPa and which does not bind specifically to SIRPg and which does not bind specifically to T-cells and which does not inhibit the proliferation of T-cells and which does not inhibit the binding of CD47 to SIRPg, for use in a diagnostic test, particularly in personalized medicine, more particularly in a companion diagnostic test.

In an embodiment, the invention relates to a method of diagnostic, particularly in personalized medicine, more particularly in a companion diagnostic test, using:
- an anti-SIRPa antibody or antigen-binding fragment thereof or antigen-binding antibody mimetic as defined above, or
- an anti-SIRPa antibody or antigen-binding fragment thereof or antigen-binding antibody mimetic which inhibits the binding of CD47 to SIRPa and which does not bind specifically to SIRPg and/or which does not bind specifically to T-cells and/or which does not inhibit the proliferation of T-cells and/or which does not inhibit the binding of CD47 to SIRPg, in particular which inhibits the binding of CD47 to SIRPa and which does not bind specifically to SIRPg and which does not bind specifically to T-cells and which does not inhibit the proliferation of T-cells and which does not inhibit the binding of CD47 to SIRPg.

In an embodiment, the invention relates to the use of:
- an anti-SIRPa antibody or antigen-binding fragment thereof or antigen-binding antibody mimetic as defined above, or
- an anti-SIRPa antibody or antigen-binding fragment thereof or antigen-binding antibody mimetic which inhibits the binding of CD47 to SIRPa and which does not bind specifically to SIRPg and/or which does not bind specifically to T-cells and/or which does not inhibit the proliferation of T-cells and/or which does not inhibit the binding of CD47 to SIRPg, in particular, which inhibits the binding of CD47 to SIRPa and which does not bind specifically to SIRPg and which does not bind specifically to T-cells and which does not inhibit the proliferation of T-cells and which does not inhibit the binding of CD47 to SIRPg, in the manufacture of a medicament for a diagnostic test, particularly in personalized medicine, more particularly in a companion diagnostic test.

In an aspect, the invention also relates to an in vitro or ex vivo method of diagnosis, in particular a method of diagnostic suitable for use in personalized medicine, more particularly in a companion diagnosis, wherein an anti-SIRPa antibody or an antigen-binding fragment thereof or an antigen-binding mimetic thereof of the invention is used for the detection of SIRPa+ cells in a sample previously obtained from a subject and optionally for the quantification of the expression of SIRPa.

In an aspect, the invention also relates to the use of an anti-SIRPa antibody or an antigen-binding fragment thereof or an antigen-binding mimetic of the invention, in the manufacture of a medicament suitable for use in a diagnostic test, in particular for use in personalized medicine, or in a companion diagnostic test.

In an aspect, the invention also relates to the use of at least one anti-human SIRPa antibody or antigen-binding fragment thereof or antigen-binding antibody mimetic of the invention, as a means for determination of the expression and/or level of expression of SIRPa in a biological sample previously obtained from an individual.

In an aspect, the invention also relates to an in vitro or ex vivo method to determine a SIRPa positive cells in a subject from a biological sample previously obtained from said subject, comprising:
i) determining in vitro the expression and/or the level of expression of SIRPa, in a biological sample previously obtained from said subject using the anti-human SIRPa antibody or antigen-binding fragment thereof or antigen-binding antibody mimetic of the invention.

In an aspect, the invention also relates to the use, in particular in vitro or ex vivo, of at least one anti-human SIRPa antibody or antigen-binding fragment thereof or antigen-binding antibody mimetic of the invention in a method wherein SIRPa is used as a biomarker that is predictive for the response to a treatment in a subject, in particular in a cancer subject.

In an aspect, the invention also relates to an in vitro or ex vivo method of predicting the response of a cancer subject to a treatment, in particular with anti-human SIRPa antibody or antigen-binding fragment thereof or antigen-binding antibody mimetic of the invention, comprising:
  determining the expression level of SIRPa in a tumour sample previously obtained from a subject, in particular with anti-human SIRPa antibody or antigen-binding fragment thereof or antigen-binding antibody mimetic of the invention, and
  comparing the expression level of SIRPa to a value representative of an expression level of SIRPa in a non-responding subject population,
wherein a higher expression level of SIRPa in the tumour sample of the subject is indicative for a subject who will respond to the treatment.

In an aspect, the invention also relates to a method of in vitro or ex vivo determining the presence of SIRPa+ cells in a sample previously obtained from a subject which comprises determining presence of SIRPa as a biomarker that is predictive for the response of a subject to a treatment, in particular a response of a subject diagnosed with a cancer, wherein said method comprises:

determining the expression level of SIRPa in a tumor sample previously obtained from a subject, in particular with anti-human SIRPa antibody or antigen-binding fragment thereof or antigen-binding antibody mimetic as defined in any one of claims 1 to 13, and comparing the expression level of SIRPa to a value representative of an expression level of SIRPa in a non-responding subject population, wherein a higher expression level of SIRPa in the tumor sample of the subject is indicative for a patient who will respond to the treatment.

Compositions

In another aspect, the invention relates to a pharmaceutical composition comprising an antibody or antigen-binding fragment thereof as defined above and a pharmaceutically acceptable carrier.

As used herein, a "pharmaceutical composition" is meant to encompass a composition suitable for administration to a subject or patient, such as a mammal, especially a human. In general, a "pharmaceutical composition" is sterile and is usually free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like.

As used herein, a "pharmaceutically acceptable carrier" is meant to encompass an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable carrier" as used herein includes both one and more than one such excipient, diluent, carrier, and adjuvant.

In particular, the invention relates to a pharmaceutical composition which comprises as an active ingredient an antibody or antigen-binding fragment thereof as defined above and a pharmaceutically acceptable carrier.

Combination Products

In another aspect, the invention relates to a therapeutic means, in particular a combination product means, which comprises as active ingredients: an anti-SIRPa antibody or antigen-binding fragment thereof or antigen-binding antibody mimetic as defined above and a second therapeutic agent, wherein said active ingredients are formulated for separate, sequential or combined therapy, in particular for combined or sequential use.

In particular, the invention relates to a combination product comprising an anti-SIRPa antibody or antigen-binding fragment thereof or antigen-binding antibody mimetic as defined above and a second therapeutic agent for simultaneous, separate or sequential use a medicament.

In an embodiment, the invention relates to a combination product as defined above, wherein the second therapeutic agent is selected from the group consisting of chemotherapeutic agents, radiotherapy agents, cell therapy agents, immunotherapeutic agents, antibiotics and probiotics.

In an embodiment, the invention relates to a combination product as defined above, wherein said immunotherapeutic agent is selected from the group consisting of therapeutic vaccines, immune checkpoint blockers or activators, in particular of adaptive immune cells (T and B lymphocytes) and antibody-drug conjugates.

In an embodiment, the invention relates to a combination product as defined above, wherein said immune checkpoint blocker or activator of adaptive immune cells (T and B lymphocytes) is selected from the group consisting of anti-PDL1, anti-PD1, anti-CTLA4, anti-CD137, anti-CD2, anti-CD28, anti-CD40, anti-HVEM, anti-BTLA, anti-CD160, anti-TIGIT, anti-TIM-1/3, anti-LAG-3, anti-2B4, and anti-OX40, anti-CD40 agonist, CD40-L, TLR agonists, anti-ICOS, ICOS-L and B-cell receptor agonists, in particular selected from the group consisting of anti-PDL1, anti-PD1 and anti-CD137.

In one embodiment, said immunotherapeutic agent is an antibody targeting tumoral antigen, particularly selected from the group consisting of anti-Her2, anti-EGFR, anti-CD20, anti-CD19, anti-CD52. In an aspect, the invention relates to a combination product as defined above, for simultaneous, separate or sequential use in the treatment of any condition susceptible of being improved or prevented by differentiating monocytic myeloid-derived suppressor cells (Mo-MDSC) into non suppressive cells.

In an embodiment, the invention relates to a method of treatment of any condition susceptible of being improved or prevented by differentiating monocytic myeloid-derived suppressor cells (Mo-MDSC) into non suppressive cells in a subject in need thereof comprising administering simultaneously, separately or sequentially to said subject an effective amount of a combination product as defined above.

In an embodiment, the invention relates to the use of a combination product as defined above in the manufacture of a medicament for the treatment any condition susceptible of being improved or prevented by differentiating monocytic myeloid-derived suppressor cells (Mo-MDSC) into non suppressive cells.

In an aspect, the invention relates to a combination product as defined above, for simultaneous, separate or sequential use in the treatment of any condition susceptible of being improved or prevented by modifying macrophage polarization to pro-inflammatory macrophages.

In an embodiment, the invention relates to a method of treatment of any condition susceptible of being improved or prevented by modifying macrophage polarization to pro-inflammatory macrophages in a subject in need thereof comprising administering simultaneously, separately or sequentially to said subject an effective amount of a combination product as defined above.

In an embodiment, the invention relates to the use of a combination product as defined above in the manufacture of a medicament for the treatment any condition susceptible of being improved or prevented by modifying macrophage polarization to pro-inflammatory macrophages.

In an aspect, the invention relates to a combination product as defined above, for simultaneous, separate or sequential use in the treatment of a pathology selected from the group consisting of a cancer, an infectious disease, a chronic inflammatory disease, an auto-immune disease, a neurologic disease, a brain injury, a nerve injury, a polycythemia, a hemochromatosis, a trauma, a septic shock, a chronic infectious disease (such as with *Pseudomonas* or CMV), fibrosis, atherosclerosis, obesity, type II diabetes and a transplant dysfunction or for use in vaccination.

In an embodiment, the invention relates to a method of treatment of a pathology selected from the group consisting of a cancer, an infectious disease, a chronic inflammatory disease, an auto-immune disease, a neurologic disease, a brain injury, a nerve injury, a polycythemia, a hemochromatosis, a trauma, a septic shock, a chronic infectious disease (such as with *Pseudomonas* or CMV), fibrosis, atherosclerosis, obesity, type II diabetes and a transplant dysfunction of a subject in need thereof comprising administering simultaneously, separately or sequentially to said subject an effective amount of a combination product as defined above.

In an embodiment, the invention relates to the use of a combination product as defined above, in the manufacture of a medicament for the treatment of a pathology selected from the group consisting of a cancer, an infectious disease, a chronic inflammatory disease, an auto-immune disease, a neurologic disease, a brain injury, a nerve injury, a polycythemia, a hemochromatosis, a trauma, a septic shock, a chronic infectious disease (such as with Pseudomonas or CMV), fibrosis, atherosclerosis, obesity, type II diabetes and a transplant dysfunction or for use in vaccination.

Nucleic Acids

In another aspect, the invention relates to an isolated nucleic acid molecule encoding an antibody or antigen-binding fragment thereof as defined above.

As used herein, a nucleic acid molecule can be double stranded and single stranded, linear and circular. It is preferably comprised in a vector which is preferably comprised in a host cell.

In an embodiment, the invention relates to an isolated nucleic acid molecule encoding an antibody or antigen-binding fragment thereof as defined above, said nucleic acid molecule comprising or consisting of at least one sequence selected from SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68 and SEQ ID NO: 69.

In an embodiment, the invention relates to an isolated nucleic acid molecule encoding an antibody or antigen-binding fragment thereof as defined above, said nucleic acid molecule comprising:
- a sequence encoding the heavy chain variable domain of said antibody, preferably comprising:
  - SEQ ID NO: 58, SEQ ID NO: 59 or SEQ ID NO: 60,
  - SEQ ID NO: 61 or SEQ ID NO: 62, and
  - SEQ ID NO: 63, SEQ ID NO: 64, SEQ ID NO: 65 or SEQ ID NO: 66,
- and/or
- a sequence encoding the light chain variable domain of said antibody, preferably comprising:
  - SEQ ID NO: 67,
  - SEQ ID NO: 68, and
  - SEQ ID NO: 69.

TABLE 5

Sequences coding the CDRs of the heavy chain variable domains and the CDRs of the light chain variable domains of antibodies according to the invention.

| | | |
|---|---|---|
| Nucleic acid sequences coding the HCDR1 (corresponding to the amino acid sequence SEQ ID NO: 14) | AGCTATTGGGTGCAC<br>TCTTATTGGGTGCAC<br>TCCTATTGGGTGCAC | SEQ ID NO: 58<br>SEQ ID NO: 59<br>SEQ ID NO: 60 |
| Nucleic acid sequence | AACATCGACCCCAGC<br>GACTCTGATACCCAT | SEQ ID NO: 61 |
| coding the HCDR2 (corresponding to the amino acid sequence SEQ ID NO: 15) | TACAATCAGAAGTTT<br>AAGGAC | |
| Nucleic acid sequence coding the HCDR2 (corresponding to the amino acid sequence SEQ ID NO: 16) | AACATCGACCCCAGC<br>GACTCTGATACACAC<br>TACTCCCCTAGCTTT<br>CAGGGC | SEQ ID NO: 62 |
| Nucleic acid sequence coding the HCDR3 (corresponding to the amino acid sequence SEQ ID NO: 17) | GGAGGAACCGGAACA<br>ATGGCTTGGTTTGCT<br>TAC | SEQ ID NO: 63 |
| Nucleic acid sequence coding the HCDR3 (corresponding to the amino acid sequence SEQ ID NO: 18) | GGAGGAACCGGCACA<br>CTGGCTTGGTTCGCT<br>TAC | SEQ ID NO: 64 |
| Nucleic acid sequence coding the HCDR3 (corresponding to the amino acid sequence SEQ ID NO: 19) | GGAGGAACCGGAACA<br>ATGGCTTACTTCGCT<br>TAT | SEQ ID NO: 65 |
| Nucleic acid sequence coding the HCDR3 (corresponding to the amino acid sequence SEQ ID NO: 20) | GGAGGAACCGGCACA<br>CTGGCTTACTTCGCT<br>TAT | SEQ ID NO: 66 |
| Nucleic acid sequence coding the LCDR1 (corresponding to the amino acid sequence SEQ ID NO: 21) | AGGTCCAGCCAGTCC<br>CTGGTGCACAGCTAT<br>GGCAACACATACCTG<br>TAT | SEQ ID NO: 67 |
| Nucleic acid sequence coding the LCDR2 (corresponding to the amino acid sequence SEQ ID NO: 22) | AGGGTGTCTAATCGG<br>TTCTCC | SEQ ID NO: 68 |
| Nucleic acid sequence coding the LCDR3 (corresponding to the amino acid sequence SEQ ID NO: 23) | TTTCAGGGCACCCAT<br>GTGCCATACACA | SEQ ID NO: 69 |

In particular, the invention relates to a nucleic acid molecule comprising or consisting of a sequence selected from SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54 and SEQ ID NO: 55.

TABLE 6

Sequences coding the heavy chain variable domains and the light chain variable domains of antibodies according to the invention.

| | | |
|---|---|---|
| Nucleic acid sequence coding the heavy chain variable domain of the wild-type antibody (chimeric and mouse 18D5) | CAGGTGCAGCTGCAG CAGCCAGGAGCTGAG CTGGTGAGGCCTGGC TCCAGCGTGAAGCTG TCCTGCAAGGCTAGC GGCTACACCTTCACA AGCTATTGGGTGCAC TGGGTGAAGCAGCGG CCAATCCAGGGCCTG GAGTGGATCGGCAAC ATCGACCCCAGCGAC TCTGATACCCATTAC AATCAGAAGTTTAAG GACAAGGCCTCTCTG ACCGTGGATAAGTCT TCCAGCACAGCTTAT ATGCAGCTGTCTTCC CTGACATTCGAGGAT TCCGCCGTGTACTAT TGCGTGAGGGGAGGA ACCGGAACAATGGCT TGGTTTGCTTACTGG GGCCAGGGCACCCTG GTGACAGTGTCTGCT | SEQ ID NO: 46 |
| Nucleic acid sequence coding the heavy chain variable domain of humanized variant (HA) | GAGGTGCAGCTGGTG CAGAGCGGAGCTGAG GTGAAGAAGCCAGGC GAGTCTCTGAGGATC TCCTGCAAGGCTAGC GGCTACACCTTCACA TCTTATTGGGTGCAC TGGGTGCGGCAGATG CCAGGCAAGGGCCTG GAGTGGATCGGCAAC ATCGACCCCAGCGAC TCTGATACCCACTAC AATCAGAAGTTTAAG GACCATGTGACCCTG TCTGTGGATAAGTCC ATCAGCACAGCCTAT CTGCAGCTGTCCAGC CTGAAGGCCTCCGAT ACAGCTATGTACTAT TGCGTGAGGGGAGGA ACCGGAACAATGGCT TGGTTCGCTTACTGG GGCCAGGGCACCCTG GTGACAGTGTCTTCC | SEQ ID NO: 47 |
| Nucleic acid sequence coding the heavy chain variable domain of humanized variant (HB) | GAGGTGCAGCTGGTG CAGTCCGGAGCTGAG GTGAAGAAGCCAGGC GAGTCTCTGAGGATC TCCTGCAAGGCTTCT GGCTACTCCTTCACC AGCTATTGGGTGCAC TGGGTGCGGCAGATG CCAGGCAAGGGCCTG GAGTGGATGGGCAAC ATCGACCCCAGCGAC TCTGATACACACTAC AATCAGAAGTTTAAG GACCATGTGACCCTG AGCGTGGATAAGTCC ATCAGCACAGCCTAT CTGCAGCTGTCCAGC CTGAAGGCCTCCGAT ACCGCTATGTACTAT TGCGTGAGGGGAGGA | SEQ ID NO: 48 |
| | ACCGGAACAATGGCT TGGTTCGCTTACTGG GGCCAGGGCACCCTG GTGACAGTGTCTTCC | |
| Nucleic acid sequence coding the heavy chain variable domain of humanized variant (HC) | GAGGTGCAGCTGGTG CAGTCTGGCGCCGAG GTGAAGAAGCCAGGC GAGAGCCTGAGGATC TCTTGCAAGGCTAGC GGCTACTCTTTCACC TCCTATTGGGTGCAC TGGGTGCGGCAGATG CCAGGCAAGGGCCTG GAGTGGATGGGCAAC ATCGACCCCAGCGAC TCTGATACACACTAC TCCCCTAGCTTTCAG GGCCATGTGACCCTG TCCGTGGACAAGTCT ATCTCCAC AGCCTATCTGCAGCT GTCCAGCCTGAAGGC CAGCGATACCGCTAT GTACTATTGCGTGAG GGGAGGAACCGGAAC AATGGCTTGGTTCGC TTACTGGGGCCAGGG CACCCTGGTGACAGT GTCTTCC | SEQ ID NO: 49 |
| Nucleic acid sequence coding the heavy chain variable domain of humanized variant (HE) | GAGGTGCAGCTGGTG CAGTCTGGCGCCGAG GTGAAGAAGCCAGGC GAGAGCCTGAGGATC TCTTGCAAGGCTAGC GGCTACTCTTTCACC TCCTATTGGGTGCAC TGGGTGCGGCAGATG CCAGGCAAGGGCCTG GAGTGGATGGGCAAC ATCGACCCCAGCGAC TCTGATACACACTAC TCCCCTAGCTTTCAG GGCCATGTGACCCTG TCCGTGGACAAGTCT ATCTCCACAGCCTAT CTGCAGCTGTCCAGC CTGAAGGCCAGCGAT ACCGCTATGTACTAT TGCGTGAGGGGAGGA ACCGGCACACTGGCT TGGTTCGCTTACTGG GGCCAGGGCACCCTG GTGACAGTGTCTTCC | SEQ ID NO: 50 |
| Nucleic acid sequence coding the heavy chain variable domain of humanized variant (HF) | GAGGTGCAGCTGGTG CAGTCTGGCGCCGAG GTGAAGAAGCCAGGC GAGAGCCTGAGGATC TCTTGCAAGGCTAGC GGCTACTCTTTCACC TCCTATTGGGTGCAC TGGGTGCGGCAGATG CCAGGCAAGGGCCTG GAGTGGATGGGCAAC ATCGACCCCAGCGAC TCTGATACACACTAC TCCCCTAGCTTTCAG GGCCATGTGACCCTG TCCGTGGACAAGTCT ATCTCCACAGCCTAT CTGCAGCTGTCCAGC CTGAAGGCCAGCGAT ACCGCTATGTACTAT | SEQ ID NO: 51 |

TABLE 6-continued

Sequences coding the heavy chain variable domains and the light chain variable domains of antibodies according to the invention.

| | |
|---|---|
| | TGCGTGAGGGGAGGA<br>ACCGGAACAATGGCT<br>TACTTCGCTTATTGG<br>GGCCAGGGCACCCTG<br>GTGACAGTGTCTTCC |
| Nucleic acid sequence coding the heavy chain variable domain of humanized variant (HEF) | GAGGTGCAGCTGGTG<br>CAGTCTGGCGCCGAG<br>GTGAAGAAGCCAGGC<br>GAGAGCCTGAGGATC<br>TCTTGCAAGGCTAGC<br>GGCTACTCTTTCACC<br>TCCTATTGGGTGCAC<br>TGGGTGCGGCAGATG<br>CCAGGCAAGGGCCTG<br>GAGTGGATGGGCAAC<br>ATCGACCCCAGCGAC<br>TCTGATACACACTAC<br>TCCCCTAGCTTTCAG<br>GGCCATGTGACCCTG<br>TCCGTGGACAAGTCT<br>ATCTCCACAGCCTAT<br>CTGCAGCTGTCCAGC<br>CTGAAGGCCAGCGAT<br>ACCGCTATGTACTAT<br>TGCGTGAGGGGAGGA<br>ACCGGCACACTGGCT<br>TACTTCGCTTATTGG<br>GGCCAGGGCACCCTG<br>GTGACAGTGTCTTCC | SEQ ID NO: 52 |
| Nucleic acid sequence coding the light chain of the wild-type antibody (chimeric and mouse 18D5) | GACGTGGTCATGACC<br>CAGACACCACTGAGC<br>CTGCCCGTGTCCCTG<br>GGCGATCAGGCCTCT<br>ATCTCCTGCAGGTCC<br>AGCCAGTCCCTGGTG<br>CACAGCTATGGCAAC<br>ACATACCTGTATTGG<br>TACCTGCAGAAGCCA<br>GGCCAGTCCCCCAAG<br>CTGCTGATCTACAGG<br>GTGTCTAATCGTTC<br>TCCGGCGTGCCTGAC<br>AGGTTCTCCGGCTCT<br>GGCTCCGGCACCGAT<br>TTCACACTGAAGATC<br>AGCAGGGTGGAGGCT<br>GAGGACCTGGGCGTG<br>TATTTCTGTTTTCAG<br>GGCACCCATGTGCCA<br>TACACATTTGGCTCT<br>GGCACCAAGCTGGAG<br>ATCAAG | SEQ ID NO: 53 |
| Nucleic acid sequence coding the light chain variable domain of humanized variant A (LA) | GACGTGGTCATGACA<br>CAGAGCCCACTGTCT<br>CTGCCTGTGACCCTG<br>GGACAGCCAGCCTCT<br>ATCTCCTGCAGGTCC<br>AGCCAGTCCCTGGTG<br>CACAGCTATGGCAAC<br>ACATACCTGTATTGG<br>TACCAGCAGAGGCCC<br>GGACAGAGCCCAAGG<br>CTGCTGA<br>TCTACAGGGTGTCTA<br>ATCGGTTCTCCGGCG<br>TGCCTGACAGGTTTA<br>GCGGCTCTGGCTCCG<br>GCACCGATTTCACAC<br>TGAAGATCTCTAGAG<br>TGGAGGCTGAGGAT<br>TGGGCGTGTATTTCT<br>GTTTTCAGGGCACCC | SEQ ID NO: 54 |

TABLE 6-continued

Sequences coding the heavy chain variable domains and the light chain variable domains of antibodies according to the invention.

| | |
|---|---|
| | ATGTGCCATACACAT<br>TTGGCGGCGGCACCA<br>AGGTGGAGATCAAG |
| Nucleic acid sequence coding the light chain variable domain of humanized variant (LB) | GACGTGGTCATGACA<br>CAGAGCCCACTGTCT<br>CTGCCTGTGACCCTG<br>GGACAGCCAGCCTCT<br>ATCTCCTGCAGGTCC<br>AGCCAGTCCCTGGTG<br>CACAGCTACGGCAAC<br>ACATACCTGTATTGG<br>TTCCAGCAGAGGCCC<br>GGACAGAGCCCAAGG<br>CTGCTGATCTATAGG<br>GTGTCTAATCGGTTC<br>TCCGGCGTGCCTGAC<br>AGGTTTAGCGGATCT<br>GGATCCGGAACCGAC<br>TTCACCCTGAAGATC<br>TCTAGAGTGGAGGCT<br>GAGGATGTGGGCGTG<br>TACTATTGTTTCCAG<br>GGCACCCATGTGCCA<br>TACACATTTGGCGGC<br>GGCACCAAGGTGGAG<br>ATCAAG | SEQ ID NO: 55 |

Vectors

In another aspect, the invention relates to a vector comprising the nucleic acid molecule as defined above.

As used herein, a "vector" is a nucleic acid molecule used as a vehicle to transfer genetic material into a cell. The term "vector" encompasses plasmids, viruses, cosmids and artificial chromosomes. In general, engineered vectors comprise an origin of replication, a multicloning site and a selectable marker. The vector itself is generally a nucleotide sequence, commonly a DNA sequence, that comprises an insert (transgene) and a larger sequence that serves as the "backbone" of the vector. Modern vectors may encompass additional features besides the transgene insert and a backbone: promoter, genetic marker, antibiotic resistance, reporter gene, targeting sequence, protein purification tag. Vectors called expression vectors (expression constructs) specifically are for the expression of the transgene in the target cell, and generally have control sequences.

Host Cells

In another aspect, the invention relates to an isolated host cell comprising a vector as defined above.

As used herein, the term "host cell" is intended to include any individual cell or cell culture that can be or has been recipient of vectors, exogenous nucleic acid molecules, and polynucleotides encoding the antibody construct of the present invention; and/or recipients of the antibody construct itself. The introduction of the respective material into the cell can be carried out by way of transformation, transfection and the like. The term "host cell" is also intended to include progeny or potential progeny of a single cell. Suitable host cells include prokaryotic or eukaryotic cells, and also include but are not limited to bacteria, yeast cells, fungi cells, plant cells, and animal cells such as insect cells and mammalian cells, e.g., murine, rat, rabbit, macaque or human.

Kits

In another aspect, the invention relates to a kit comprising:

an antibody or antigen-binding fragment thereof as defined above, a nucleic acid molecule coding said antibody or antigen-binding, a vector comprising said nucleic acid molecule, and/or a cell comprising said vector.

As a matter of convenience, the antibody of the present invention can be provided in a kit, i.e., a packaged combination of reagents.

In the context of the present invention, the term "kit" means two or more components (one of which corresponding to the antibody or antigen-binding thereof, the nucleic acid molecule, the vector or the cell of the invention) packaged together in a container, recipient or otherwise. A kit can hence be described as a set of products and/or utensils that are sufficient to achieve a certain goal, which can be marketed as a single unit.

The kit may comprise one or more recipients (such as vials, ampoules, containers, syringes, bottles, bags) of any appropriate shape, size and material containing the antibody construct of the present invention in an appropriate dosage for administration. The kit may additionally contain directions for use (e.g. in the form of a leaflet or instruction manual), means for administering the antibody construct of the present invention such as a syringe, pump, infuser or the like, means for reconstituting the antibody construct of the invention and/or means for diluting the antibody construct of the invention.

In an embodiment, the invention relates to a kit as defined above for a single-dose administration unit. The kit of the invention may also contain a first recipient comprising a dried/lyophilized antibody construct and a second recipient comprising an aqueous formulation. In certain embodiments of this invention, kits containing single-chambered and multi-chambered pre-filled syringes (e.g., liquid syringes and lyosyringes) are provided.

Antigens

In an aspect, the invention relates to a polypeptide, in particular an antigen, comprising or consisting of the epitope sequence of human SIRPa consisting of SEQ ID NO: 3 (KFRKGSPD[DV]/[T]E).

In an embodiment, the invention relates to a polypeptide, in particular an antigen, comprising or consisting of the epitope sequence of human SIRPa consisting of SEQ ID NO: 3 (KFRKGSPD[DV]/[T]E), said polypeptide having a size up to 300 amino acids.

In an embodiment, the polypeptide of the invention has a size between 50 and 300, preferably between 100 and 250 amino acids.

In an embodiment, the polypeptide of the invention has a size up to 50, 100, 150, 200, 250 or 300 amino acids.

In an embodiment, the invention relates to a polypeptide, in particular an antigen, comprising or consisting of the epitope sequence of human SIRPa consisting of SEQ ID NO: 3 (KFRKGSPD[DV]/[T]E) and at least one epitope sequence of human SIRPa consisting of SEQ ID NO: 1 (SLIPVGP), SEQ ID NO: 2 (G/ARELIYNQKEGH), SEQ ID NO: 4 (QHTVSFTCESHGFSPRDITLKWF), SEQ ID NO: 5 (ICEVAHVTLQG) or SEQ ID NO: 6 (YPQRLQLTWLE).

In an embodiment, the invention relates to a polypeptide, in particular an antigen, comprising or consisting of the epitope sequences of human SIRPa consisting of SEQ ID NO: 1 (SLIPVGP), SEQ ID NO: 2 (G/ARELIYNQKEGH), SEQ ID NO: 3 (KFRKGSPD[DV]/[T]E), SEQ ID NO: 4 (QHTVSFTCESHGFSPRDITLKWF), SEQ ID NO: 5 (ICEVAHVTLQG) and SEQ ID NO: 6 (YPQRLQLTWLE).

In an embodiment, the invention relates to a polypeptide, in particular an antigen, comprising or consisting of at least one peptide selected from the group consisting of SEQ ID NO: 70, SEQ ID NO: 71 and SEQ ID NO: 72, said polypeptide consisting of a sequence of up to 300 amino acids.

In an embodiment, the invention relates to a polypeptide, in particular an antigen, comprising or consisting of the peptide of amino acid sequence set forth in SEQ ID NO: 73 (YNQK) and/or the peptide of SIR amino acid sequence within SIRPa, said polypeptide consisting of a sequence of up to 300 amino acids.

Method of Manufacturing an Antibody

In an aspect, the invention also relates to a method of manufacturing an antibody, in particular an antibody of the invention, comprising immunizing a non-human animal, in particular a non-human mammal, against at least one antigen as defined above, and in particular collecting the resulting serum from said immunised non-human animal to obtain antibodies directed against said antigen.

In particular, the invention also relates to a method of manufacturing an antibody comprising immunizing a non-human animal against an antigen comprising or consisting of the epitope sequence of human SIRPa consisting of SEQ ID NO: 3 (KFRKGSPD[DV]/[T]E), and in particular collecting the resulting serum from said immunised non-human animal to obtain antibodies directed against said antigen.

In particular, the invention also relates to a method of manufacturing an antibody comprising immunizing a non-human animal against an antigen comprising or consisting of the epitope sequence of human SIRPa consisting of SEQ ID NO: 3 (KFRKGSPD[DV]/[T]E) and at least one epitope sequence of human SIRPa selected from the group consisting of SEQ ID NO: 1 (SLIPVGP), SEQ ID NO: 2 (G/ARELIYNQKEGH), SEQ ID NO: 4 (QHTVSFTCESHGFSPRDITLKWF), SEQ ID NO: 5 (ICEVAHVTLQG) or SEQ ID NO: 6 (YPQRLQLTWLE), and in particular collecting the resulting serum from said immunised non-human animal to obtain antibodies directed against said antigen.

In particular, the invention also relates to a method of manufacturing an antibody comprising immunizing a non-human animal against an antigen comprising or consisting of the epitope sequences of human SIRPa consisting of SEQ ID NO: 1 (SLIPVGP), SEQ ID NO: 2 (G/ARELIYNQKEGH), SEQ ID NO: 3 (KFRKGSPD[DV]/[T]E), SEQ ID NO: 4 (QHTVSFTCESHGFSPRDITLKWF), SEQ ID NO: 5 (ICEVAHVTLQG) and SEQ ID NO: 6 (YPQRLQLTWLE), and in particular collecting the resulting serum from said immunised non-human animal to obtain antibodies directed against said antigen.

Method of Selecting an Antibody

In an aspect, the invention relates to a method of selecting an antibody of the invention, an antigen-binding fragment or mimetic of such an antibody, comprising or consisting of at least one of the following steps:

a. testing (e.g. according to a method describing in the Examples 1, 2 and 3) the ability of an antibody, an antigen-binding fragment or mimetic of such an antibody to bind to SIRPa, in particular to an antigen as defined above, b. testing (e.g. according to a method describing in the Examples 7 and 8) the ability of an antibody, an antigen-binding fragment or mimetic of such an antibody to bind to SIRPb, c. testing (e.g. according to a method describing in the Examples 9 and 10) the ability of an antibody, an antigen-binding fragment or mimetic of such an antibody to bind to SIRPg, d. testing (e.g. according to a method describing in the Examples 4 and 5) the ability of an antibody, an antigen-binding fragment or mimetic of such an antibody to inhibit the binding of human CD47 to human SIRPa;

e. testing (e.g. according to a method describing in the Example 12) the ability of an antibody, an antigen-binding fragment or mimetic of such an antibody to bind to T cells;

f. testing (e.g. according to a method describing in the Example 13) the ability of an antibody, an antigen-binding fragment or mimetic of such an antibody to inhibit the T cells proliferation;

g. testing (e.g. according to a method describing in the Example 11) the ability of an antibody, an antigen-binding fragment or mimetic of such an antibody to inhibit the binding of human CD47 to human SIRPg;

and optionally comprising the following step:

selecting an antibody, an antigen-binding fragment or mimetic of such an antibody which specifically binds to SIRPa, in particular to an antigen as defined above, and which significantly inhibits the binding of CD47 to SIRPa, and which does not bind specifically to human SIRPg, and/or which does not bind specifically to human T-cells, and/or which does not significantly inhibit the proliferation of human T-cells, and/or which does not significantly inhibit the binding of human CD47 to human SIRPg; more particularly which specifically binds to SIRPa, in particular to an antigen as defined above, and which significantly inhibits the binding of CD47 to SIRPa, and which does not bind specifically to human SIRPg, and which does not bind specifically to human T-cells, and which does not significantly inhibit the proliferation of human T-cells, and which does not significantly inhibit the binding of human CD47 to human SIRPg.

The method of selecting an antibody of the invention can advantageously being performed further to the method of manufacturing an antibody according to the invention.

The following Figures and Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

FIGURE LEGENDS

FIG. 1A, B, C, D. Binding analyses of anti-SIRPa antibodies by ELISA assay (human SIRPa-His coating and anti-human kappa detection).

Assessment by ELISA on immobilized SIRPa-His of chimeric (♦), HALA (□), HFLA (*), HFLB (+), HEFLA (▲), HEFLB (■), SIRP29 (Δ), Kwar23 (○) on A; of HCLA (●), HCLB (×), HELA (◊), HELB (−) on B; of HALB (−), HBLA (_), HBLB (※) on C. Revelation was performed with a donkey anti-human antibody and revealed by colorimetry at 450 nm using TMB substrate. ED50 is the concentration of the indicated antibody to reach 50% of the signal in this assay. Binding of m18D5 clone (■) (n=4), SE5A5 commercial clone (▲) (n=7), 6G10 clone (∇) (n=3) and 12D7 clone (□) (n=4) on D.

FIG. 2. Affinity analysis by Biacore of anti-SIRP antibodies on human SIRPa recombinant protein.

SIRPa-His recombinant protein was immobilized onto a CM5 chip at 5 μg/ml (500 RU) and the indicated antibodies were added at different concentration. Values were measured after an association period (ka) of 3 min followed by a dissociation period of 10 min (kd) to determine affinity constant (KD).

Figure 3A:
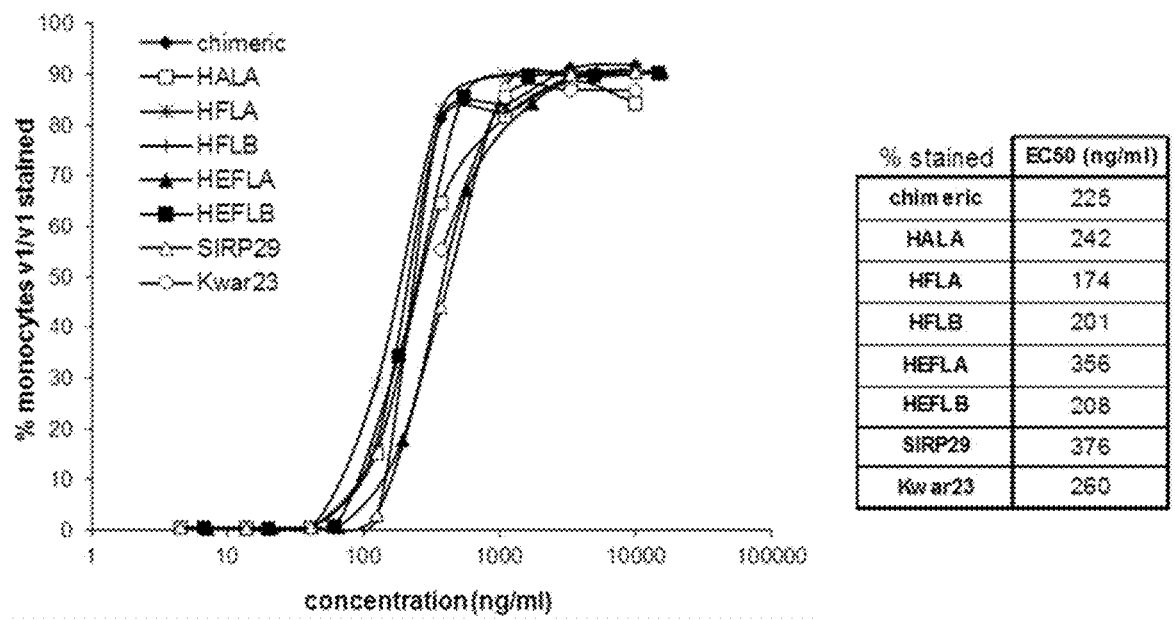
Figure 3B:
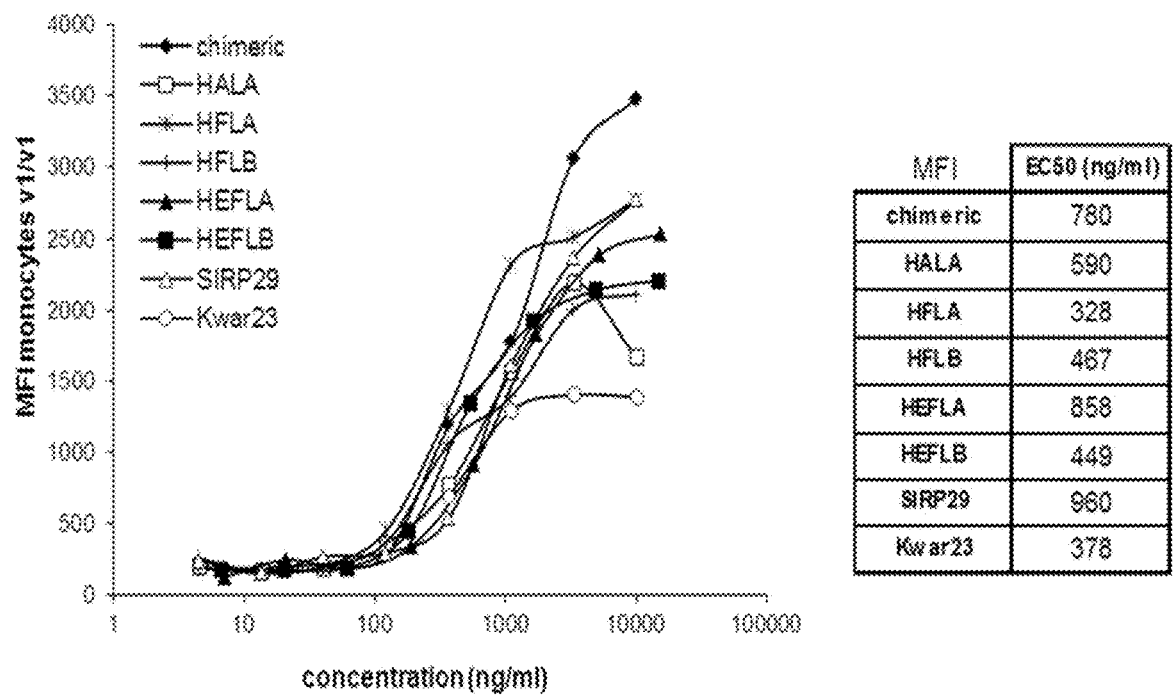
Figure 3C:
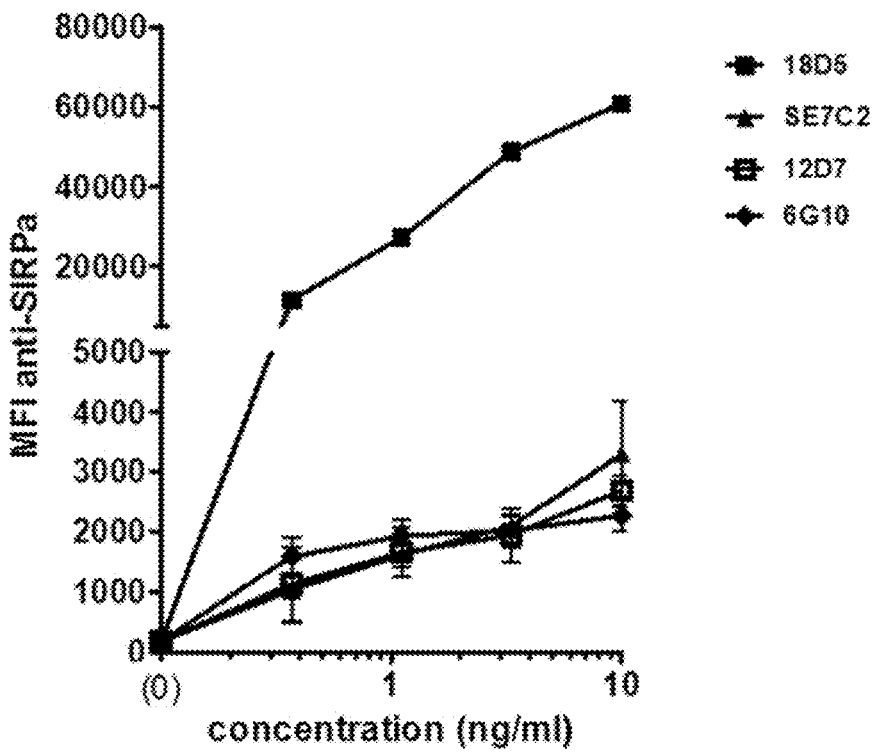
Figure 3D:
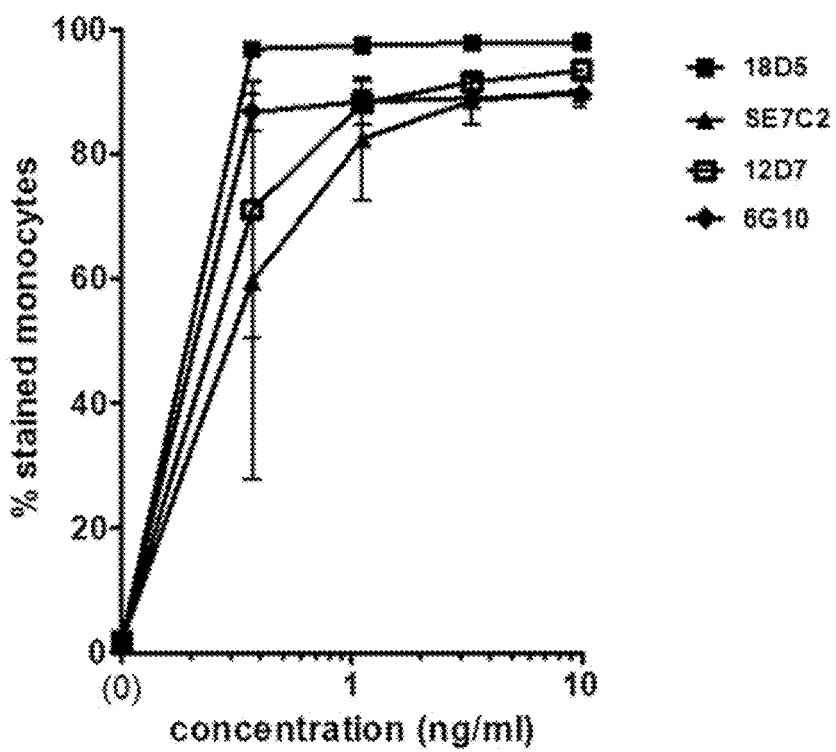
Figure 3E:
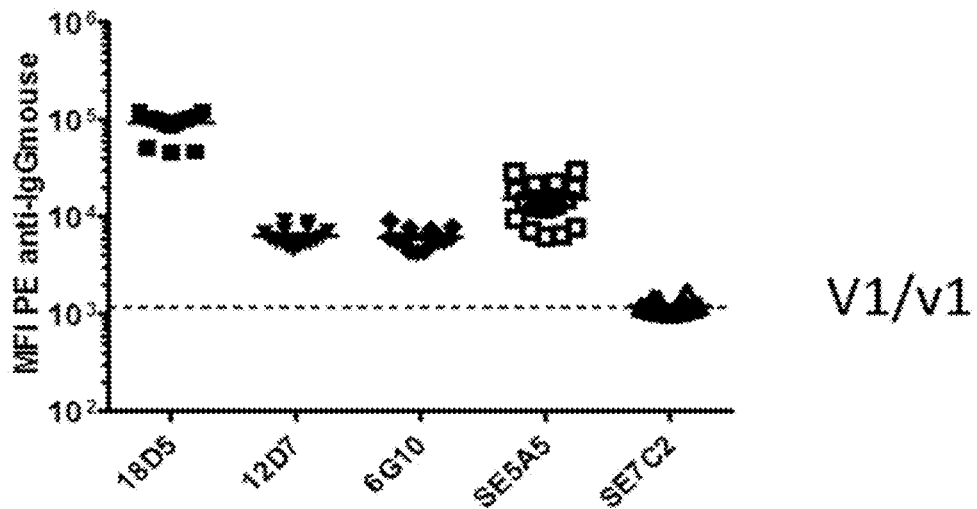
Figure 3F:
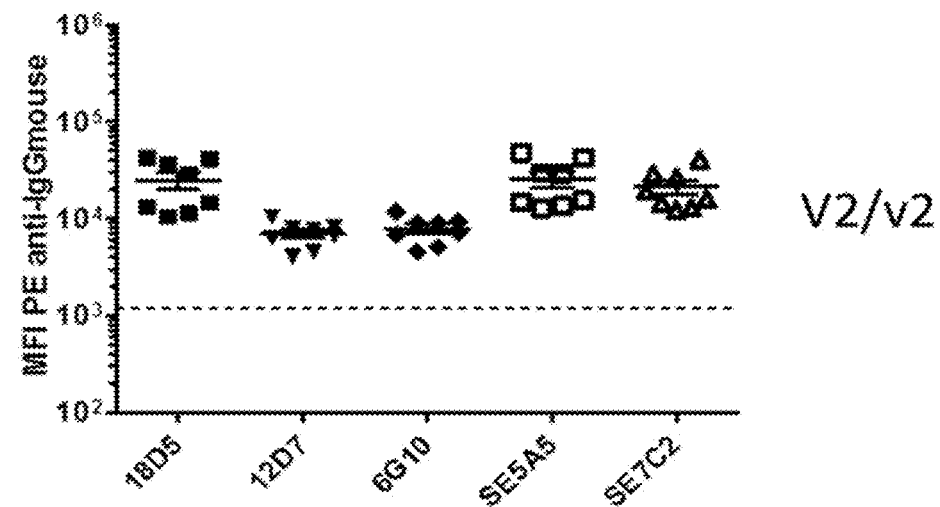
Figure 3G:
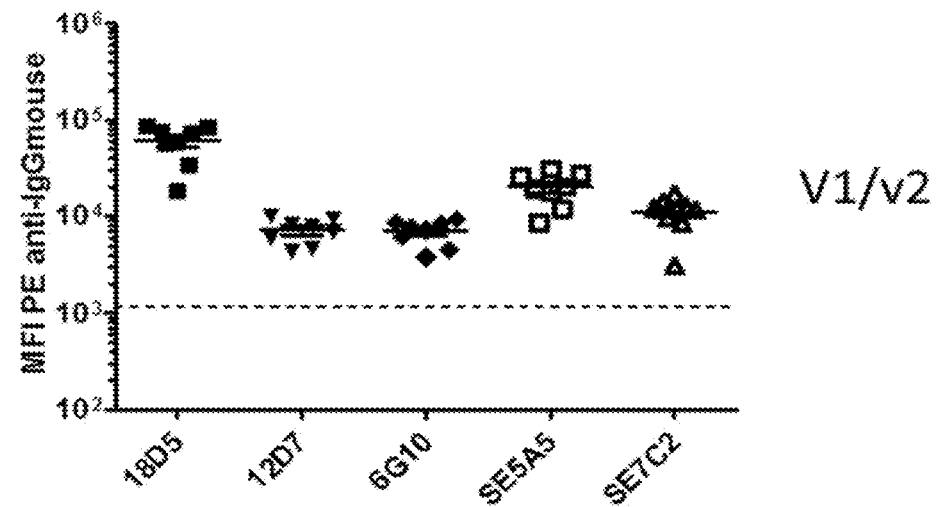

FIG. 3A, B, C, D, E, F, G. Binding analyses of anti-SIRPa antibodies on human monocytes (homozygote for SIRPa variant 1 (v1/v1)).

(A, B) Assessment by cytofluorometry on human monocytes v1/v1 (previously stained with human Fc Receptor Binding Inhibitor antibody) of chimeric (♦), HALA (□), HFLA (*), HFLB (+), HEFLA (▲), HEFLB (■), SIRP29 (Δ), Kwar23 (○). Revelation was performed with a PE labeled mouse anti-human Fc mAb on CantoII cytometer, values corresponding to percentage of stained monocytes. ED50 is the concentration of the indicated antibody to reach 50% of the signal in this assay. A corresponds to the percentage of monocytes v1/v1 stained. B corresponds to the mean of fluorescence intensity (MFI) of monocytes v1/v1.

(C, D) Binding study of SIRPa antibodies on human monocytes by Flow cytometry (FACS): different anti-SIRPa antibodies were tested: m18D5 (■) (n=1), SE7C2 (▲) (n=2), 12D7 (□) (n=2), 6G10 (♦) (n=4): C represents the Mean Fluorescence Intensity (MFI) of the different antibodies over a dose response. D represents the percentage of stained monocytes over antibody dose response. Statistical analysis were performed when it was possible.

(E, F, G) SIRPa variants binding in the population by anti-h SIRPa antibodies: The capacity of different anti-hSIRPa antibodies to bind SIRPa variants in the 32 volunteers was measured by FACS with a PE-anti mouse IgG. All clones were tested at 10 μg/ml: m18D5 (■), 12D7 (▼), 6G10 (♦) and commercial antibodies SE5A5 (□), SE7C2 (Δ). E represents the homozygote Variant 1 volunteers (n=16). F represents the homozygote variant 2 volunteers (n=8). G represents the heterozygote V1/V2 volunteers (n=8).

Figure 4A:
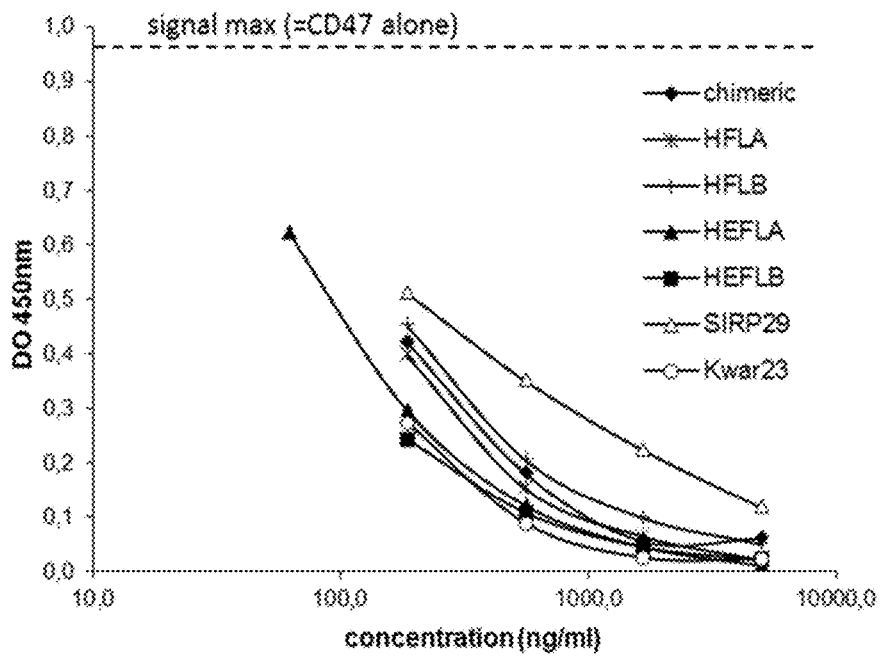

FIG. 4A, B, C. Competition of anti-SIRPa antibodies with CD47 on SIRPa.

(A) Assessment by ELISA on immobilized SIRPa-His of chimeric (♦), HFLA (*), HFLB (+), HEFLA (▲), HEFLB (■), SIRP29 (Δ), Kwar23 (○) at different concentrations incubated with constant concentration of biotinylated CD47-Fc (6 μg/ml). Revelation was performed with streptavidin peroxidase to detect CD47 molecule and revealed by colorimetry at 450 nm using TMB substrate. (B) The results of a second experiment are given with the IC50 values. IC50 is the concentration of the indicated antibody to inhibit 50% of the signal in this assay.

(C) Antagonist activity study of anti-SIRPa antibodies on SIRPa-CD47 interaction by ELISA: The different anti-SIRPa antibodies were tested over a dose response: m18D5 clone (■) (n=1), commercial antibody SE5A5 (▲) (n=2) and m12D7 (□) (n=2). The figure represents the percentage of CD47 positive SIRPa-CD47 interactions measured by ELISA during a dose response of anti-hSIRPa antibodies.

Figure 5A:
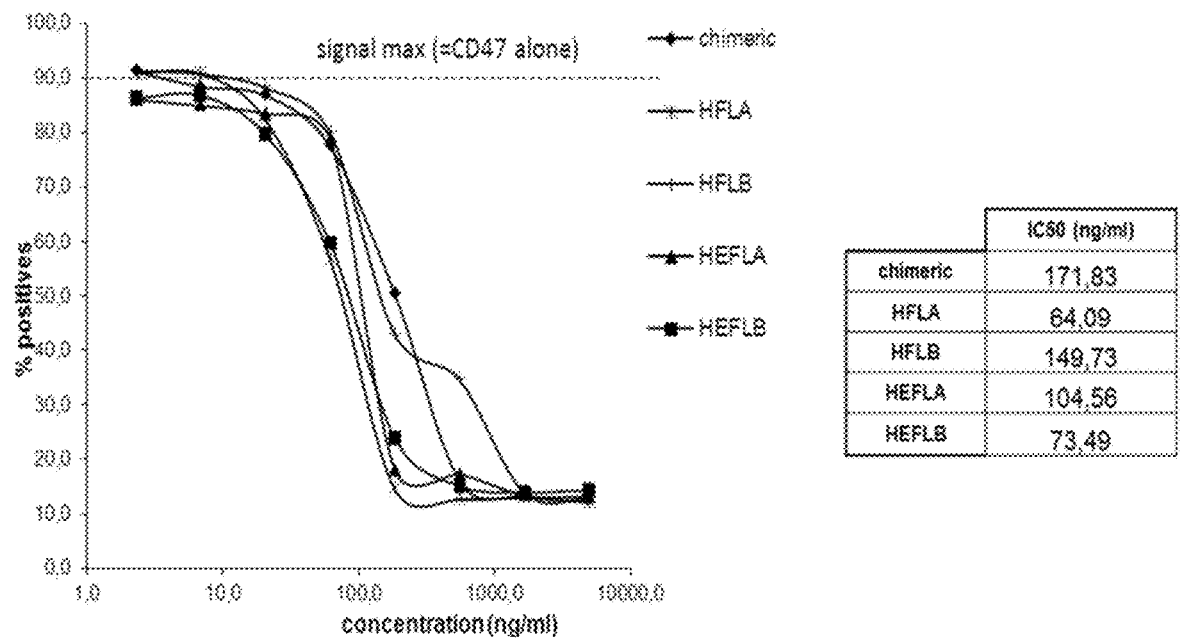

FIG. 5A, B, C. Competition of anti-SIRPa antibodies with CD47 on human monocytes.

(A, B) Assessment by cytometry on human monocytes (v1/v1) of chimeric (◆), HFLA (*), HFLB (+), HEFLA (▲), HEFLB (■) at different concentrations incubated with constant concentration of biotinylated CD47-Fc (10 µg/ml). Revelation was performed with PhycoErythrin-streptavidin to detect CD47 molecule and revealed by CantoII cytometer. IC50 is the concentration of the indicated antibody to inhibit 50% of the signal in this assay. A corresponds to the percentage of positive cells. B corresponds to the mean of fluorescence intensity.

(C) Antagonist activity study of anti-SIRPa antibodies on Sirpa-CD47 interaction by FACS: The different anti-SIRPa antibodies were tested over a dose response: m18D5 clone (■) (n=1), commercial antibody SE7C2 (▲) (n=2) and m12D7 (□) (n=2). C represents the percentage of CD47 positive cells measured by FACS after competition with anti-hSIRPa antibodies.

FIG. 6A, B. (A) Affinity analysis by Blitz of anti-SIRP antibody on human SIRPa recombinant protein pre-incubated or not with SP-D ligand. SIRPa-His recombinant protein was immobilized onto a NINTA biosensor at 10 µg/ml and the SP-D ligand was added at 100 µg/ml (saturating concentration). Then anti-SIRPa antibody was added at 20 µg/ml and affinity values were deduced after an association period (ka) of 120 sec followed by a dissociation period of 120 sec (kd) to determine affinity constant (KD). (B) Affinity analysis by Blitz of anti-SIRP antibody on human SIRPa recombinant protein pre-incubated with mouse 18D5 antibody. SIRPa-His recombinant protein was immobilized onto a NINTA biosensor at 10 µg/ml and the anti-SIRPa antibody was added at 20 µg/ml (saturating concentration). Then SP-D ligand was added at 100 µg/ml and affinity values were deduced after an association period (ka) of 120 sec followed by a dissociation period of 120 sec (kd) to determine affinity constant (KD).

Figures 7A, 7B:
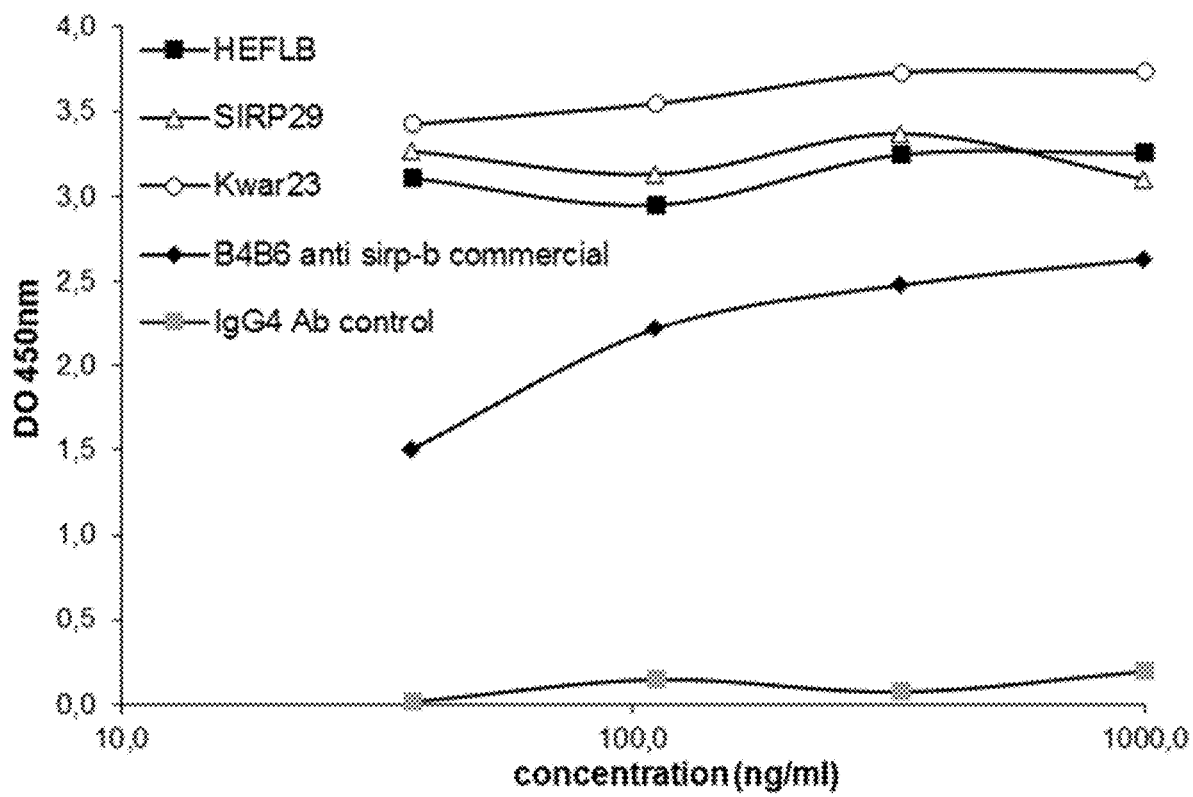

FIG. 7A, B. (A) Affinity analysis by Blitz of anti-SIRP antibodies on human SIRPb recombinant protein.

SIRPb-His recombinant protein was immobilized onto a NINTA biosensor and the indicated antibodies were added at 20 µg/ml. Values were deduced after an association period (ka) of 120 sec followed by a dissociation period of 120 sec (kd) to determine affinity constant (KD). (B) Binding analysis of anti-SIRP antibodies (human SIRPb-His coating and anti-human kappa detection). Assessment by ELISA on immobilized SIRPb-His of HEFLB (■), SIRP29 (Δ), Kwar23 (○), B4B6 (◆) and IgG4 Ab control (✻). Revelation was performed with a donkey anti-human antibody with the exception of B4B6 revealed with a mouse antibody and revealed by colorimetry at 450 nm using TMB substrate.

Figures 8A, 8B:
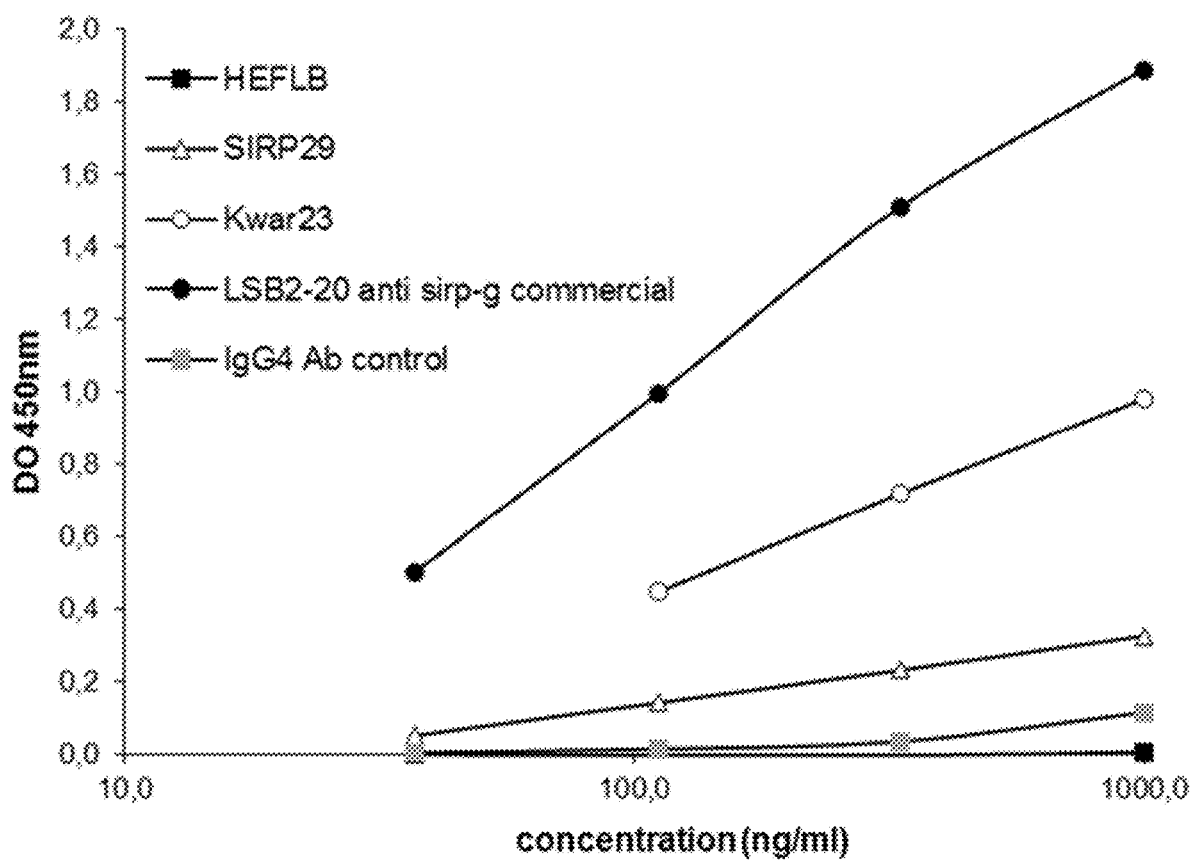

FIG. 8A, B. (A) Affinity analysis by Blitz of anti-SIRP antibodies on human SIRPg recombinant protein.

SIRPg-His recombinant protein was immobilized onto a NINTA biosensor and the indicated antibodies were added at 10 µg/ml. Values were deduced after an association period (ka) of 120 sec followed by a dissociation period of 120 sec (kd) to determine affinity constant (KD). (B) Binding analysis by ELISA assay of anti-SIRP antibodies on SIRPg (human SIRPg-His coating and anti-human kappa detection). Assessment by ELISA on immobilized SIRPg-His of HEFLB (■), SIRP29 (Δ), Kwar23 (○), LSB2-20 (●) and IgG4 Ab control (✻) Revelation was performed with a donkey anti-human antibody and revealed by colorimetry at 450 nm using TMB substrate.

FIG. 9. Affinity analysis by Blitz of CD47 on human SIRPg recombinant protein pre-incubated with anti-SIRP antibodies. SIRPg-His recombinant protein was immobilized onto a NINTA biosensor at 10 µg/ml and the indicated antibodies were added at 20 µg/ml (saturating concentration). Then, CD47Fc was added at 100 µg/ml and affinity values were deduced after an association period (ka) of 120 sec followed by a dissociation period of 120 sec (kd) to determine affinity constant (KD).

Figure 10A:
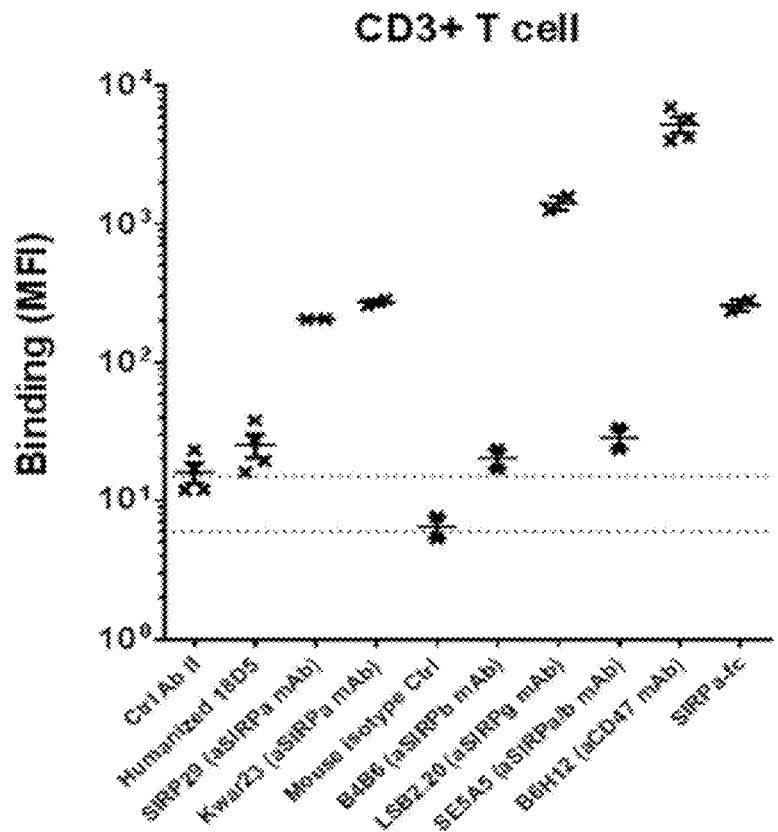

FIG. 10A, B, C. Geometric mean fluorescence intensity measured by flow cytometry on (A) peripheral human CD3+ T cells, (B) red blood cells or (C) platelets after staining with different monoclonal antibodies and revealing with secondary anti-IgG fluorescent antibody.

Figures 11A, 11B:
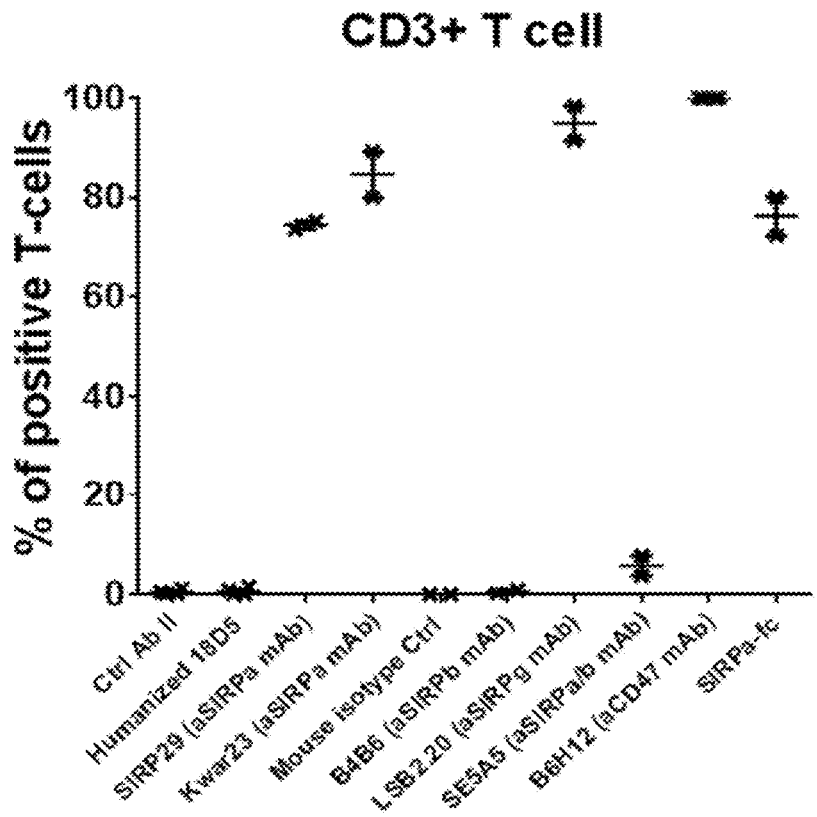

FIG. 11A, B. (A) Percentage of positive peripheral human CD3+ T cells after staining with different monoclonal antibodies. (B) The table indicates the value of % of positive cells in duplicate experiments.

Figure 12A:
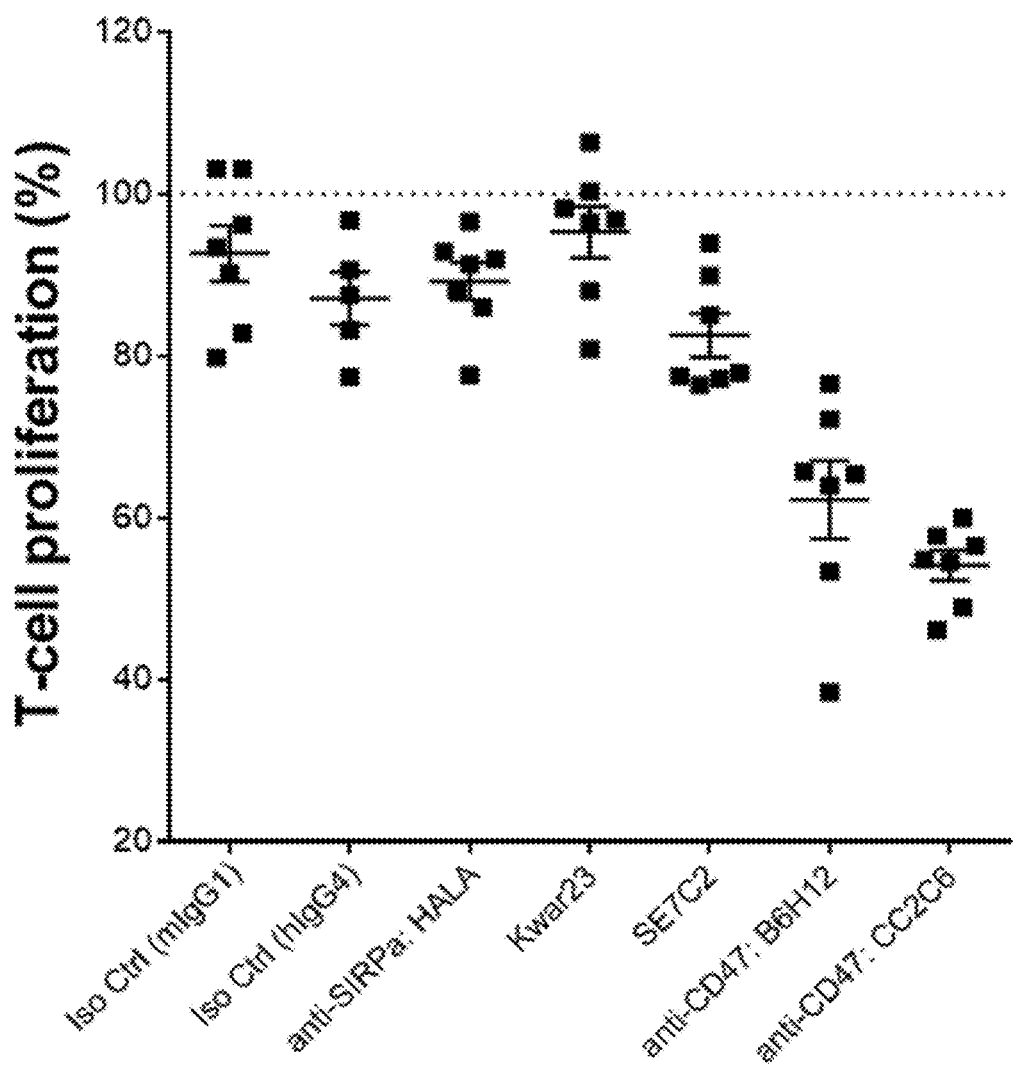
Figure 12B:
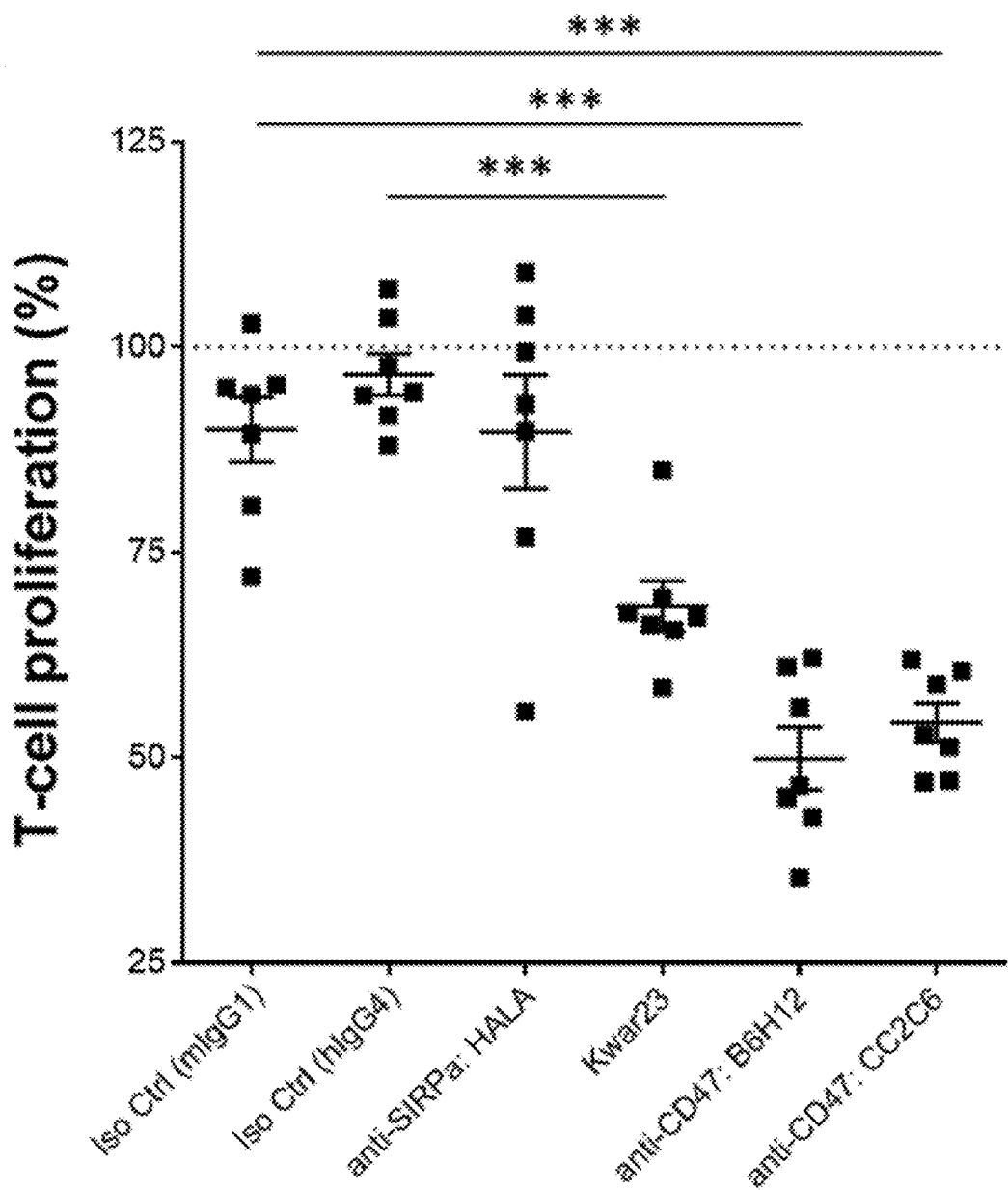
Figure 12C:
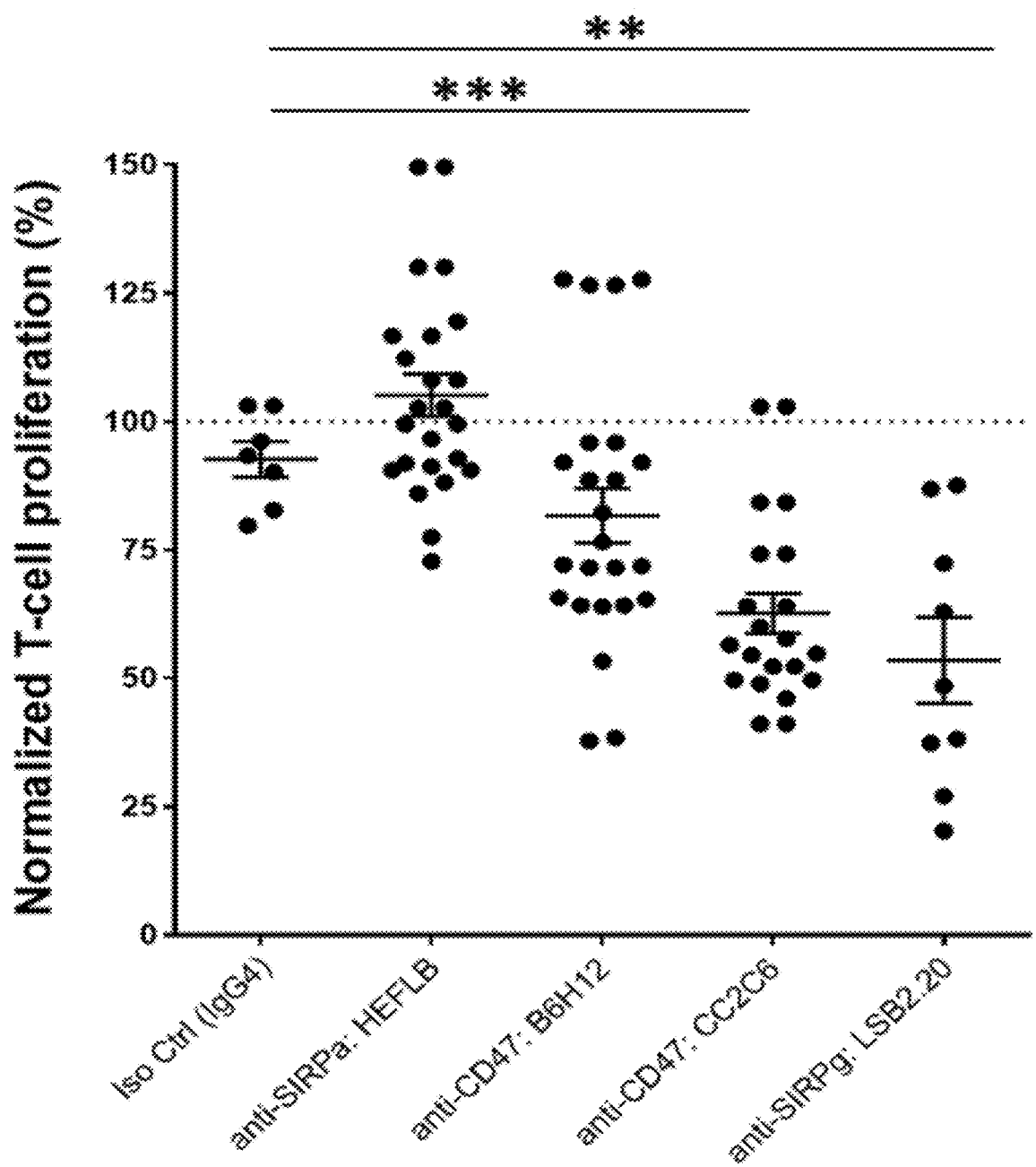
Figure 12D:
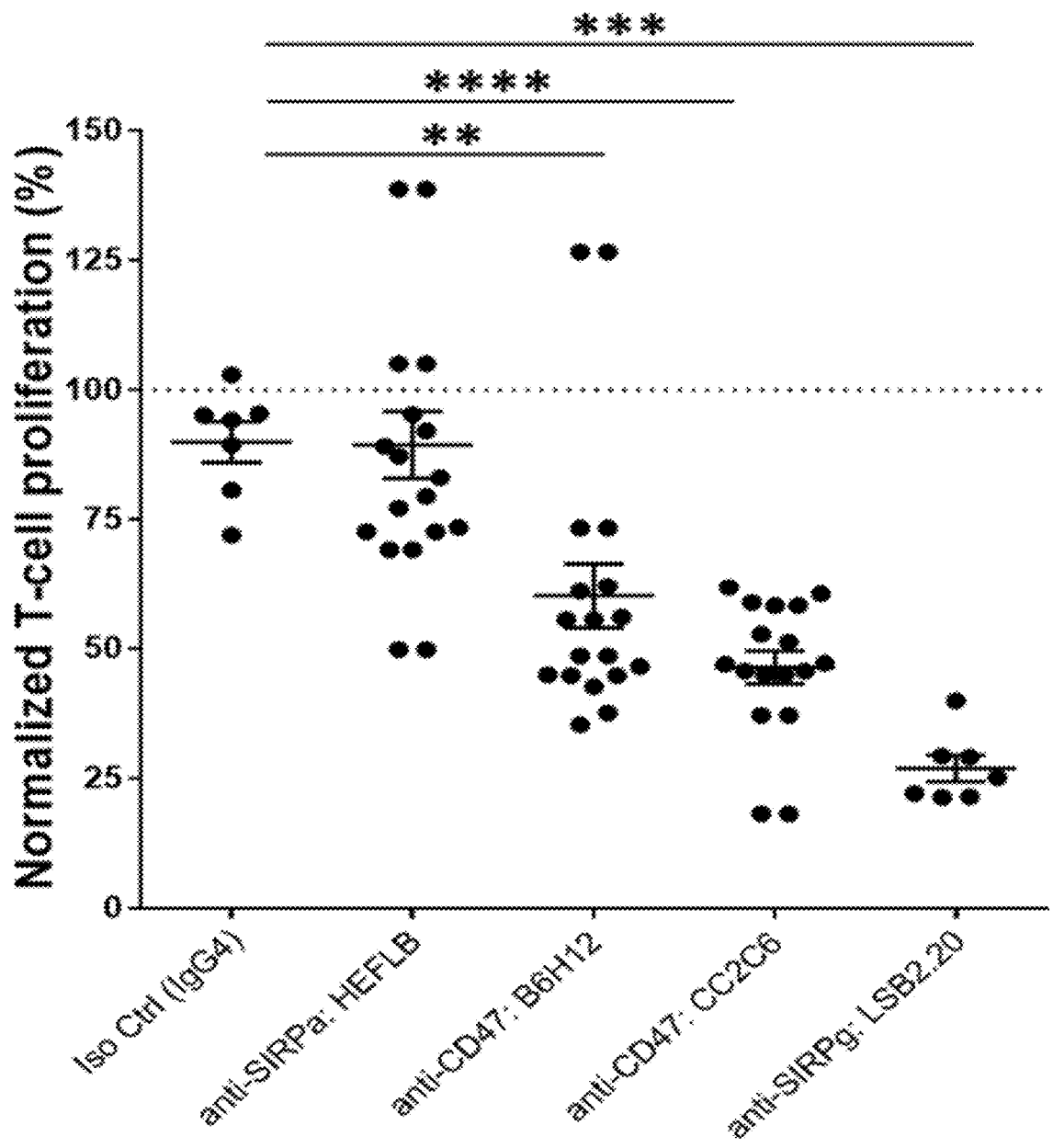
Figure 12E:
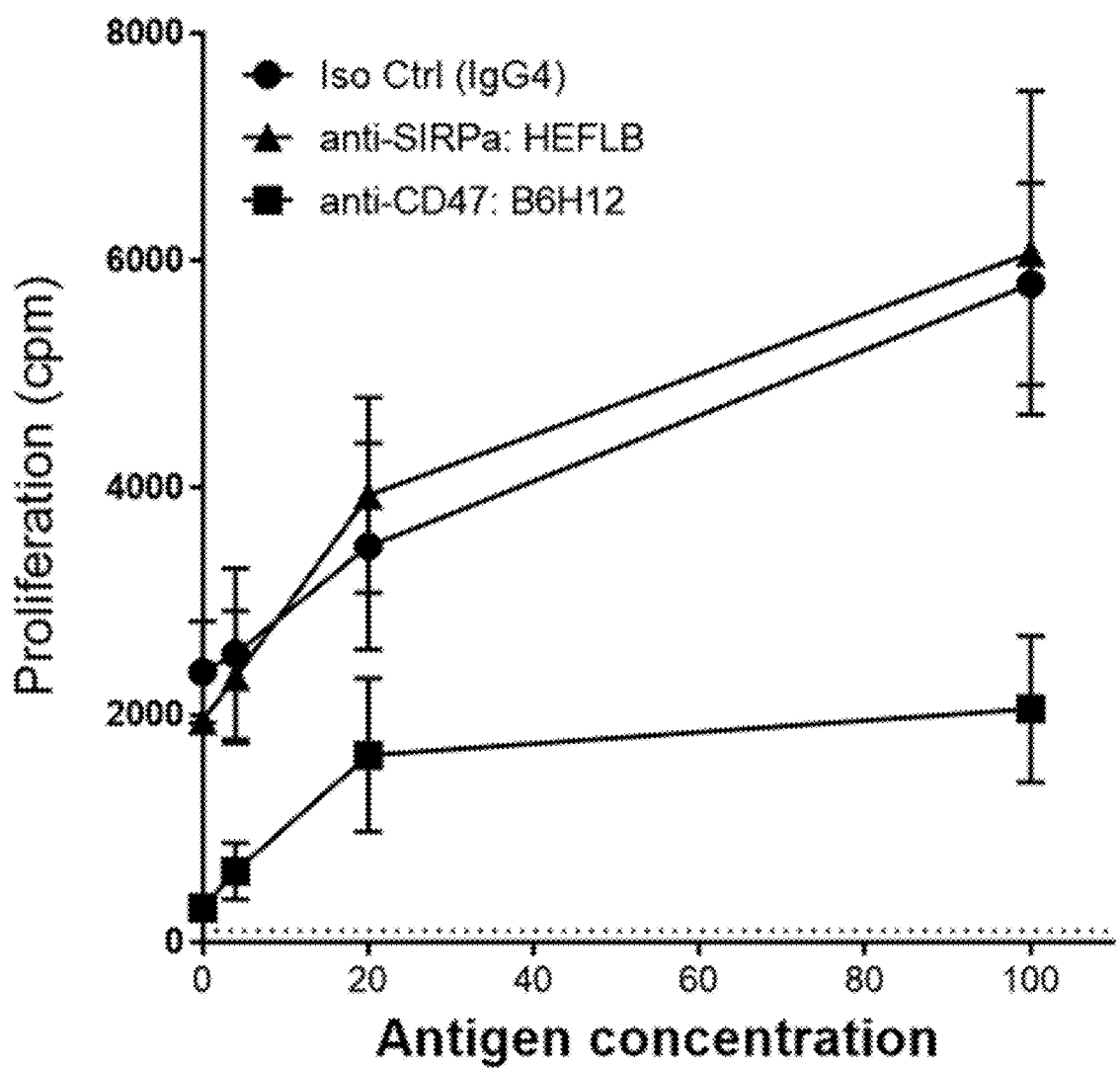

FIG. 12A, B, C, D, E. Human T cells isolated from peripheral blood mononuclear cells from healthy volunteers were stimulated with (A) (C) anti-CD3+ anti-CD28 beads at a 1:1 ratio for 3 days or (B) (D) with allogeneic dendritic cells (DC) at a 5 T cell:1 DC ratio for 5 days or (E) with different concentrations of tuberculin unpurified protein derivative (PPD) for 5 days. Antibodies were added at day 0 of the culture. Proliferation was measured by incorporation of $H^3$-thymidine during the last 12 h of culture.

Figure 13:
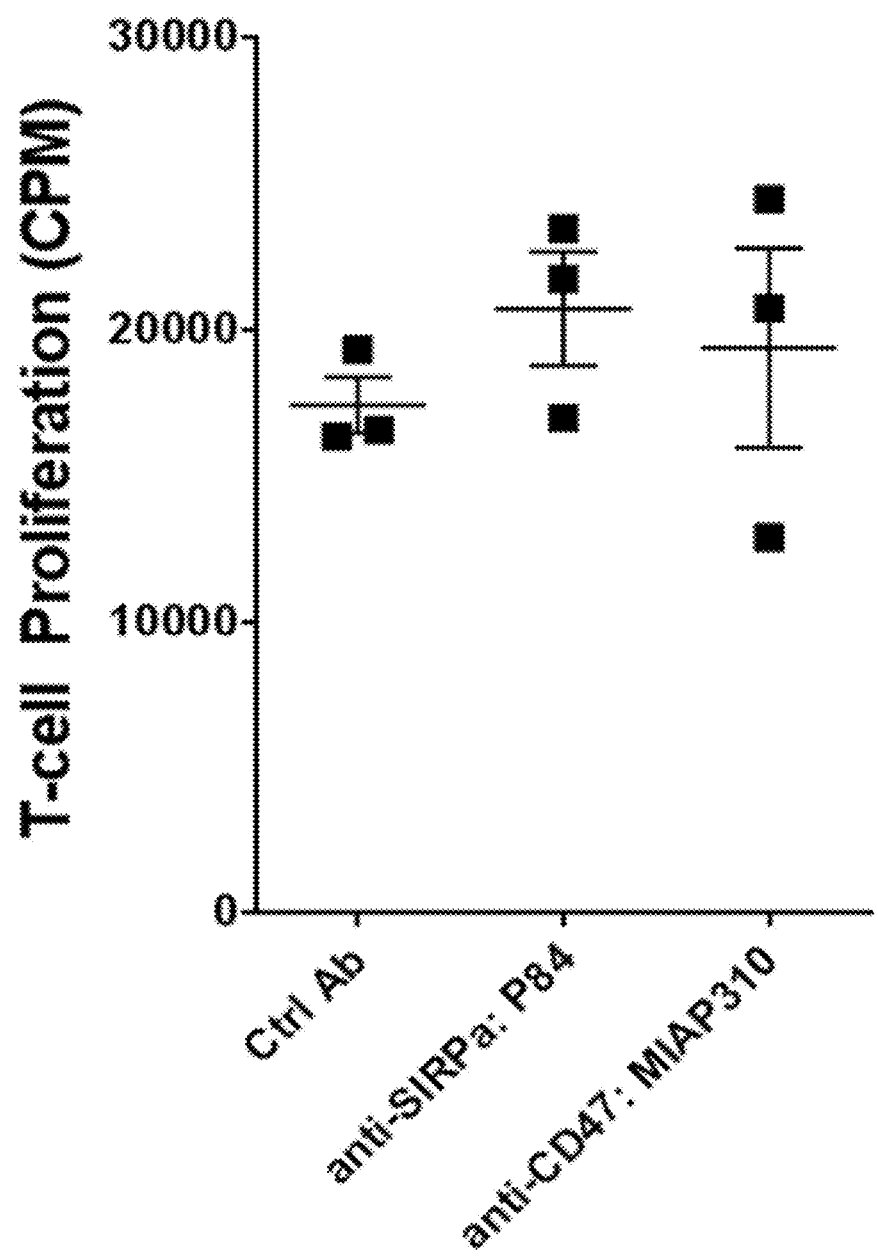

FIG. 13. Mouse CD8+ T cells were isolated from splenocytes of naïve mice. CD8 T cells were stimulated with anti-CD3+ anti-CD28 beads at a 1:1 ratio for 3 days. Antibodies were added at day 0 of the culture. Proliferation was measured by incorporation of $H^3$-thymidine during the last 12 h of culture.

Figure 14A:
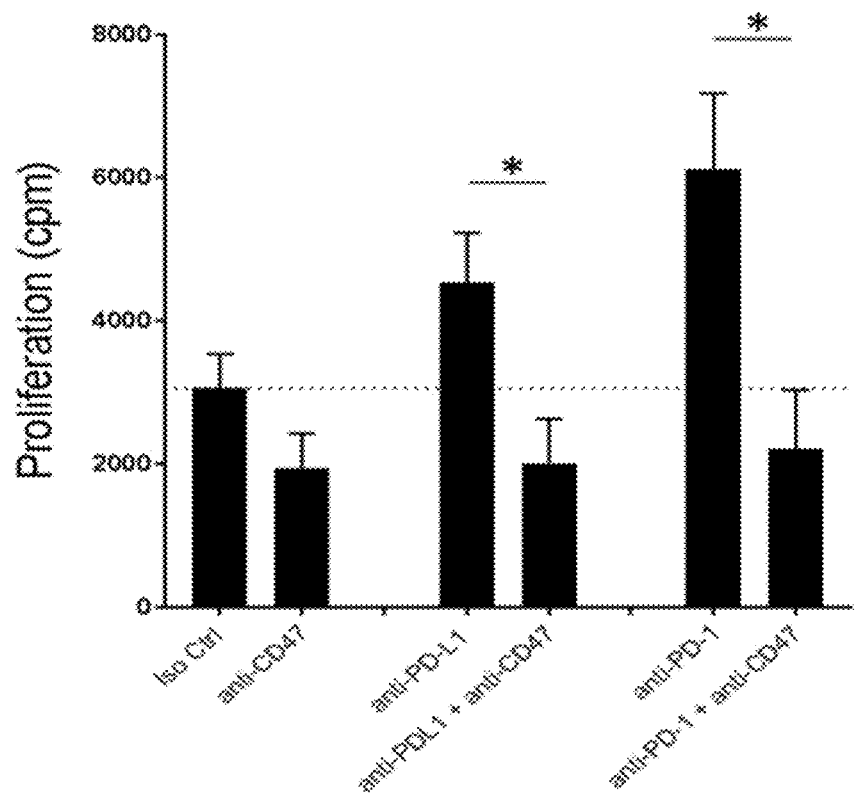

FIG. 14A, B. Human T cells isolated from peripheral blood mononuclear cells from healthy volunteers were stimulated with allogeneic dendritic cells (DC) at a 5 T cell:1 DC ratio for 5 days. Antibodies were added at day 0 of the culture. Proliferation was measured by incorporation of $H^3$-thymidine during the last 12 h of culture.

Figure 15A:
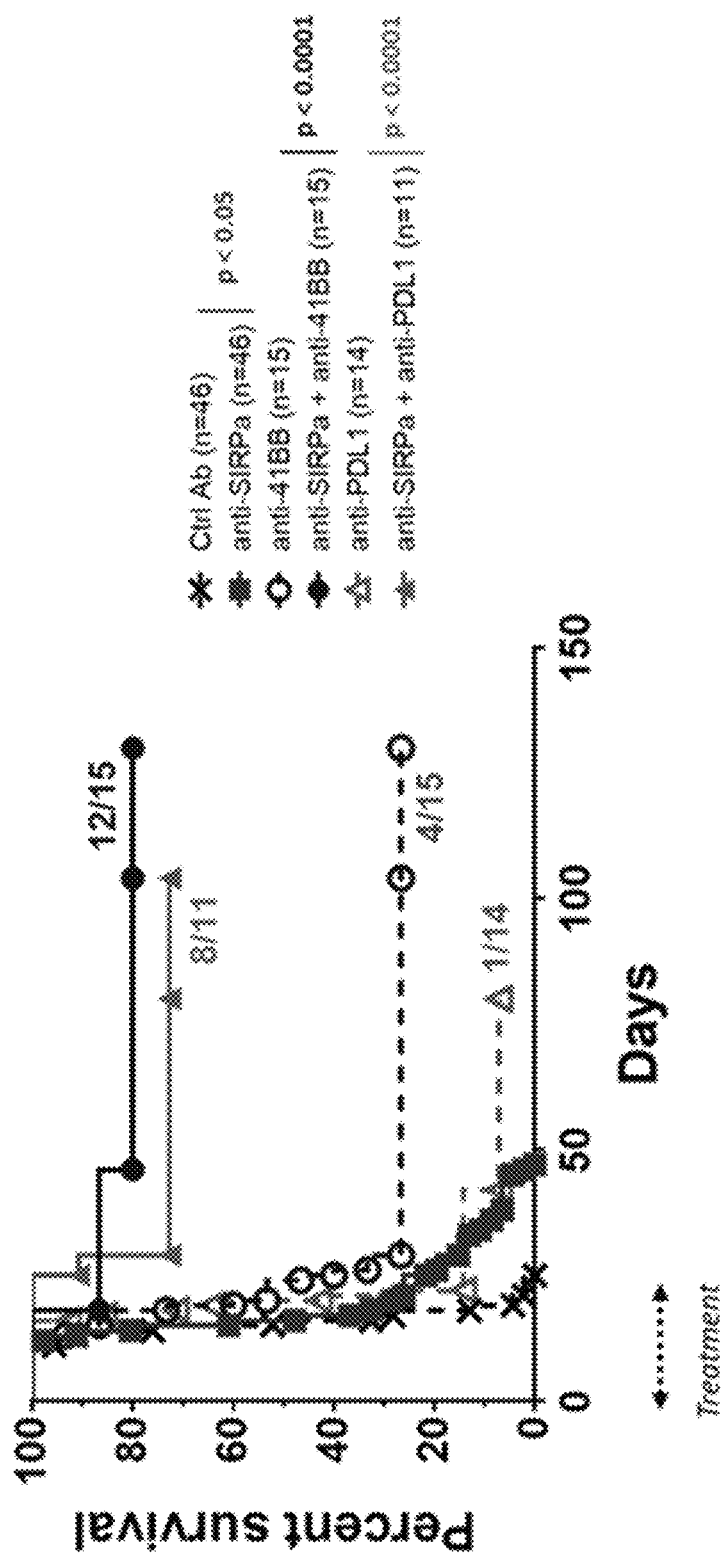

FIG. 15A, B, C, D, E. (A) Anti-tumor effect of anti-SIRPa (P84 clone) i.p. administration three times a week for 4 weeks (300 µg/injection) in combination or not with two injection (day 4 & 8) of anti-4-1-BB mAb (3H3 clone, 100 µg/injection) or with injections (twice a week) of anti-PDL-1 (10F.9G2 clone, 200 µg/injection, treatment during 4 weeks) in an orthotropic model of murine hepatoma (2.5.10^6 of Hepa 1.6 cells injected through the portal vein on day 0). Mice were considered cured when they survived three times longer than the time necessary to all control mice died. (B) Tumor infiltrating cells were analyzed at day 13 after tumor inoculation. (C) Tumor infiltrating cells and spleen cells were analyzed at day 13 after tumor inoculation. (D) Mice previously cured in the hepatoma model by anti-SIRPa+ anti-4-1BB injection or SIRPa mutant mice treated with anti-4-1BB were rechallenged by Hepa 1.6 cells injection in the spleen (2.5.10^6 cells/mouse). Naive mice were injected in parallel in the same route in order to compare tumor development with rechallenged mice. Mice were then left untreated. (E) Mice previously cured in the hepatoma model by anti-SIRPa+anti-4-1BB were rechallenged by Hepa 1.6 cells injection in the spleen (2.5.10^6 cells/mouse) and their spleen was harvested 30 days after rechallenge. Splenocytes and T-cell splenocytes were isolated. Naive mice were injected intravenously with vehicle, whole splenocytes (10.10^6/mouse) or T-cell purified from splenocytes (2.5.10^6/mouse) and all received Hepa1.6 cell injection in the spleen (2.5.10^6 cells/mouse). Mice were then left untreated and considered cured when they survived three times longer than the time necessary to all control mice died.

Figure 16:
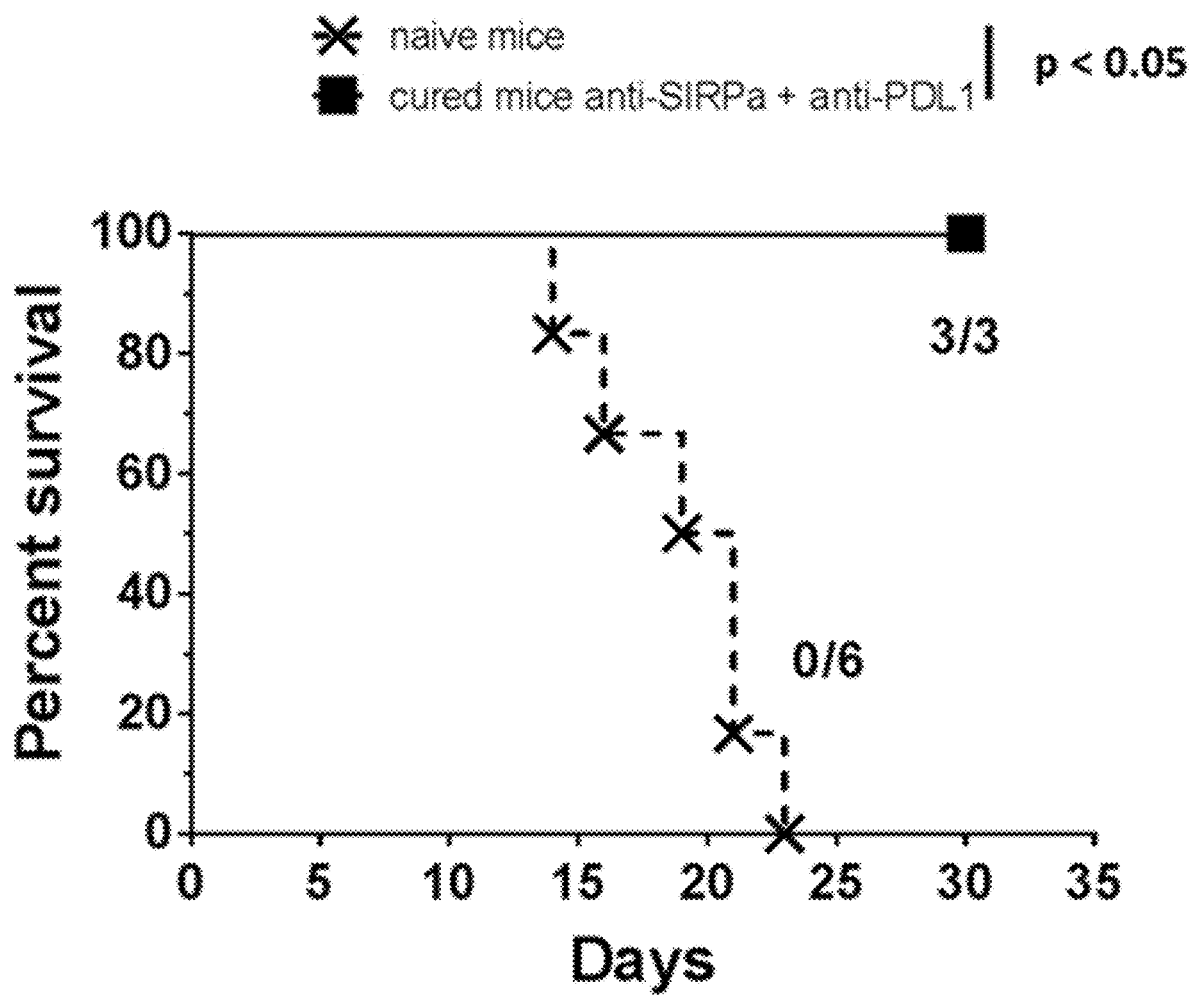

FIG. 16. Mice previously cured in the hepatoma model by anti-SIRPa+anti-PDL1 injection were rechallenged by Hepa 1.6 cells injection in the spleen (2.5.10^6 cells/mouse). Naive mice were injected in parallel in the same route in order to compare tumor development with rechallenged mice. Mice were then left untreated.

Figure 17:
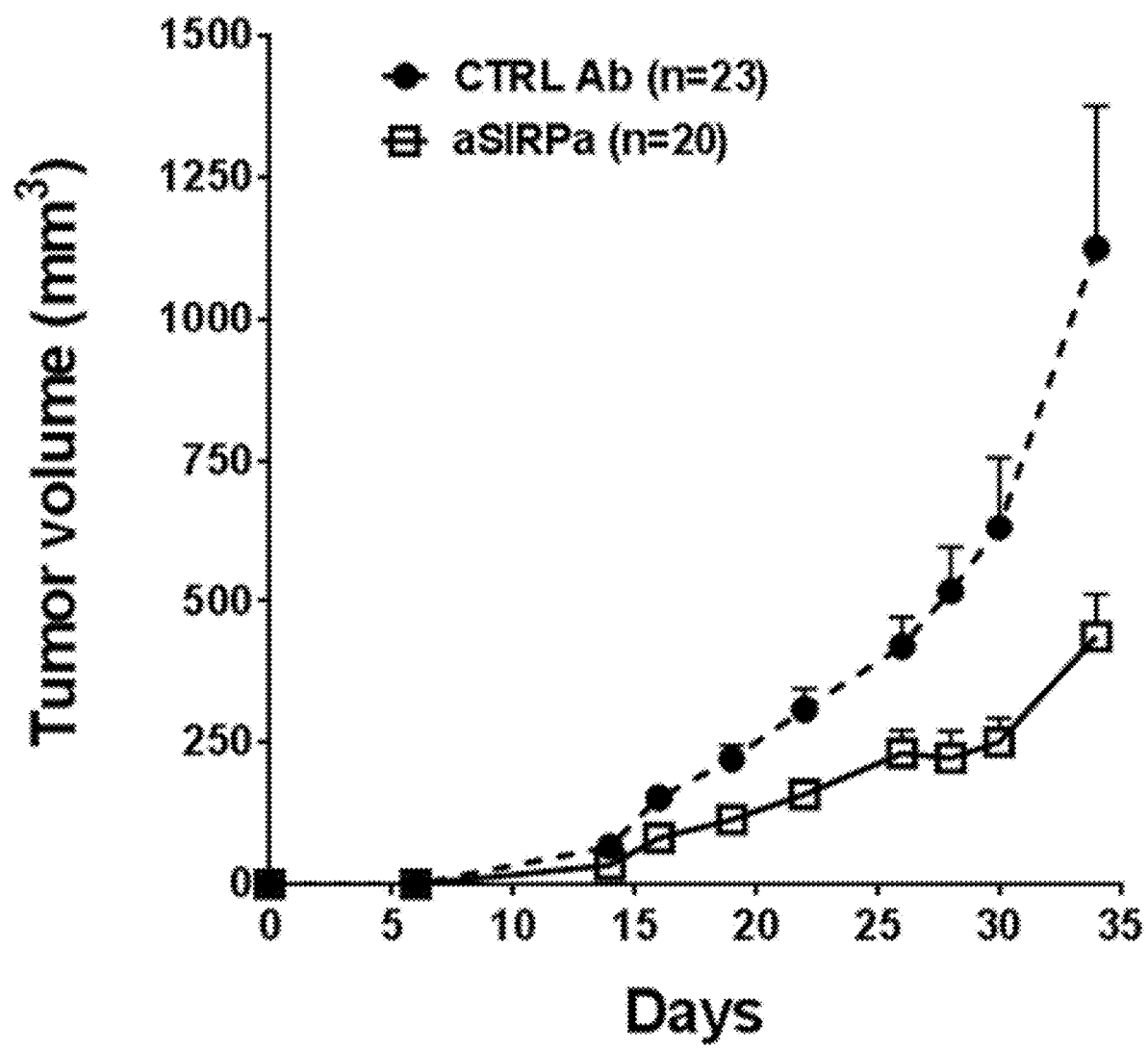

FIG. 17. Anti-tumor effect of anti-SIRPa (P84 clone) i.p. administration three times a week for 4 weeks (200 μg/injection) in an orthotopic model of murine mammary carcinoma (0.25.10^6 of 4T1 cells injected in the mammary gland). The tumor development was evaluated by measuring the diameter of the tumor and calculated according to the formula:=$(0.52*(d^2))^{\wedge}1.5$. Mice were euthanized when tumor development was nearly 1000 mm$^3$ according to the ethical guidelines.

Figure 18A:
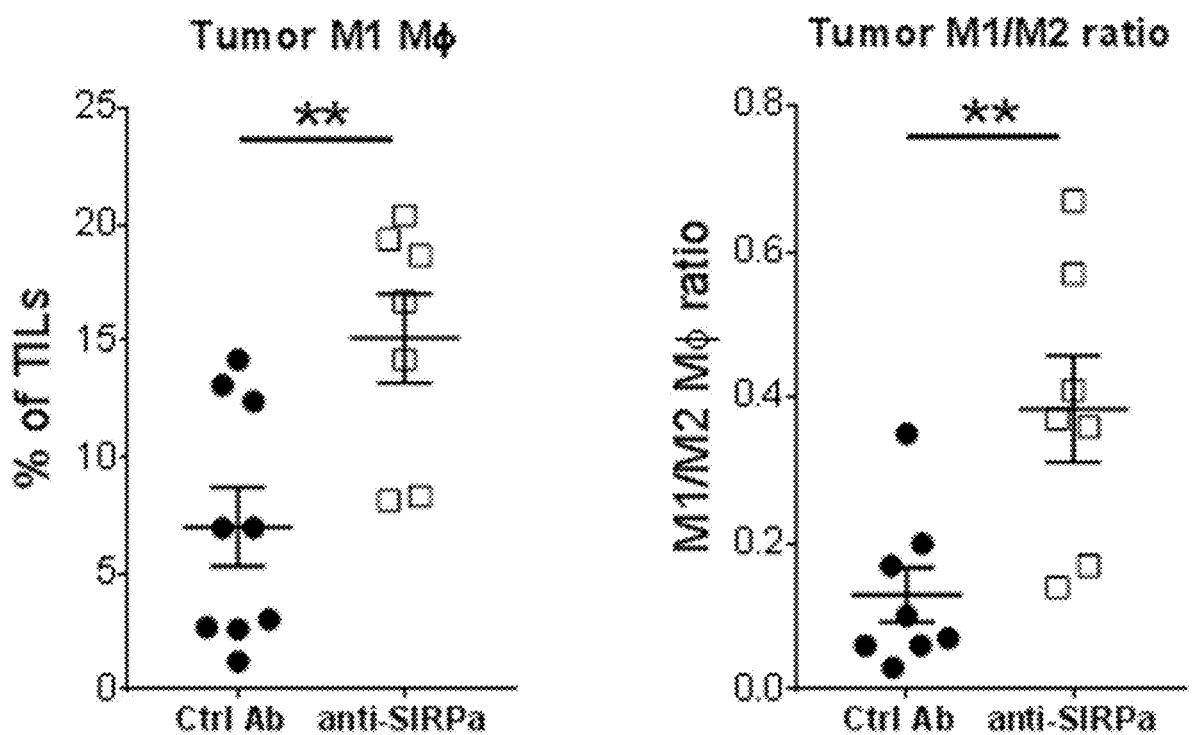

FIG. 18A, B, C. Immune cells phenotype analysis in spleen, tumor and lymph nodes of mice treated with anti-SIRPa (P84 clone) or ctrl mAb i.p. three times a week for two weeks (200 μg/injection) in an orthotropic model of murine mammary carcinoma (0.25.10^6 of 4T1 cells injected in the mammary gland). Immune cell analysis were performed two weeks after tumor inoculation.

Figure 19A:
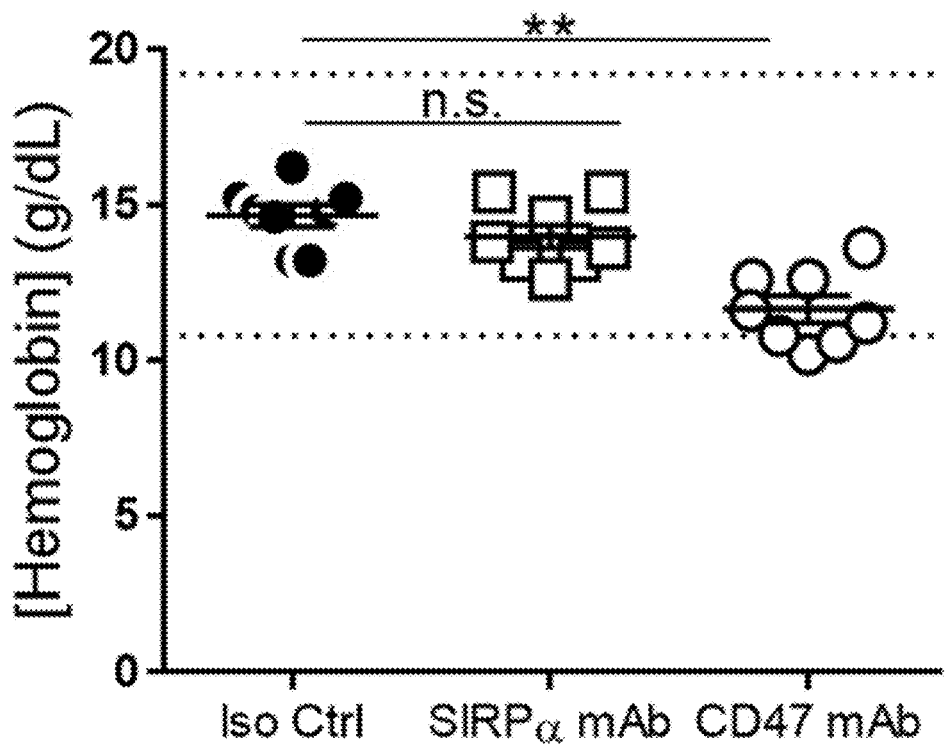

FIG. 19A, B. Anti-SIRPa (P84 clone), anti-CD47 (MIAP410 clone) and irrelevant isotype control were administered intraperitoneally at day 0 and day 2 at 12 mg/kg in C57Bl/6 mice. Blood samples were collected at day 0 and day 3 in EDTA containing tubes and blood count was performed with a XS-800i hematology analyzer (Sysmex). The level of hemoglobin (A) and the percentage of hematocrit U (B) were evaluated at day 3. The dotted-lines represent normal range values in the C57Bl/6 mice for each parameter.

Figure 20A:
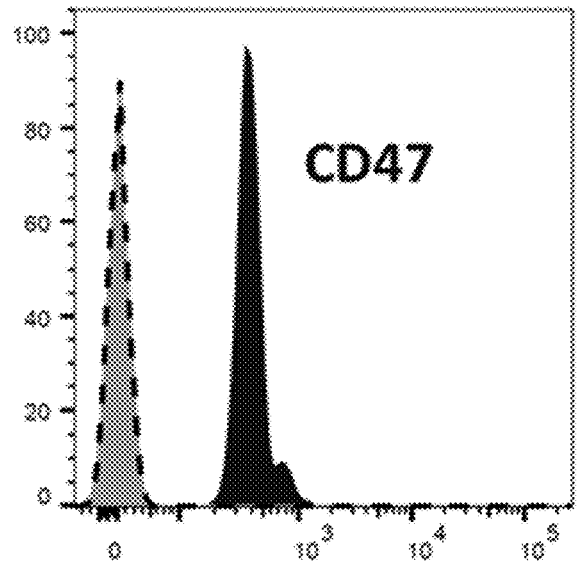

FIG. 20A, B. (A) Flow cytometry analysis of anti-SIRPa (HEFLB, grey) and anti-CD47 (B6H12, black) mAb as compared to a control mAb (dotted line) on human platelets freshly isolated from the blood of healthy donors. (B) Human platelet aggregation measurement using optical aggregometer in the presence of a 50 μg/ml of control mAb, anti-SIRPa (HEFLB), anti-CD47 (B6H12) or anti-integrin αIIb as positive control of inhibitor of aggregation. Antibodies were evaluated on non-activated and ADP-activated platelets.

Figure 21B:
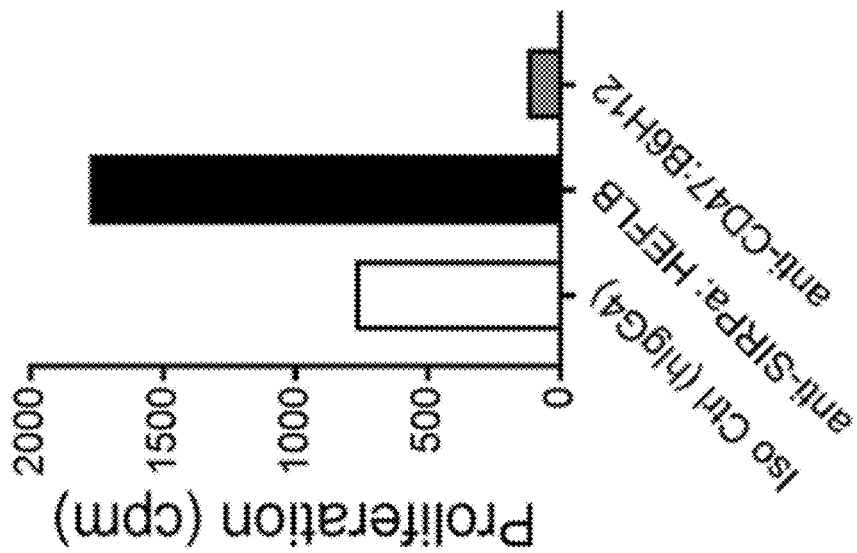
Figure 21A:
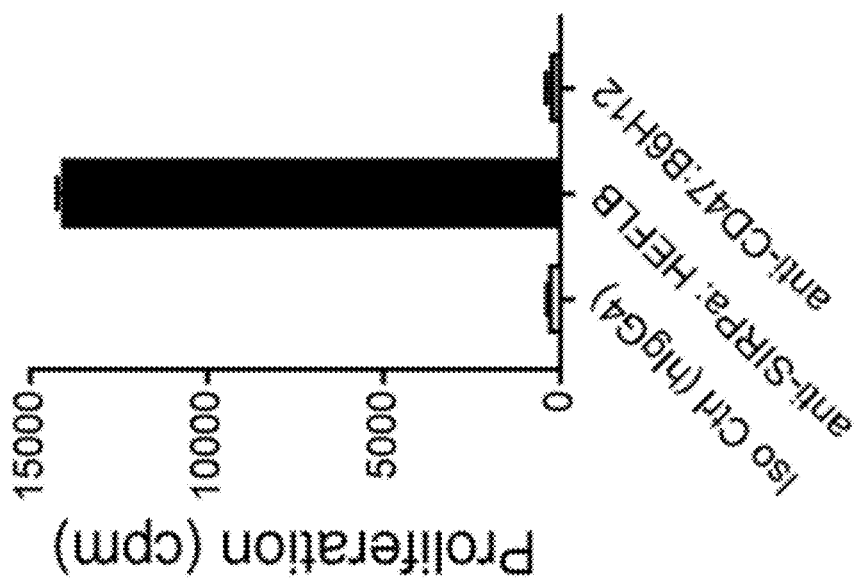

FIG. 21A, B, C. Allogeneic CD4+ T cells were cultured in a 1:1 ratio with CD14+ myeloid cells extracted from (A) fresh or (B) frozen ovarian cancer ascites with 10 μg/ml of control antibody (white), anti-SIRPa HEFLB (black) or anti-CD47 mAb (grey). Proliferation was measured at day 5 by $^3$H-thymidine incorporation. (C) Alternatively, allogeneic T cells were cultured in a 5:1 ratio with allogeneic dendritic cells and different ratio of CD14+ myeloid cells extracted from ovarian cancer ascites in the presence of 10 μg/ml of antibody as in (A).

EXAMPLES

In the following Examples, the antibody "18D5" (or "m18D5") corresponds to the mouse antibody 18D5, the "chimeric" antibody corresponds to the chimeric mouse/human 18D5 antibody, and the antibodies "HALA, HALB, HBLA, HBLB, HCLA, HCLB, HELA, HELB, HFLA, HFLB, HEFLA and HEFLB" correspond to specific humanized 18D5 variants. The antibodies 6G10 and 12D7 belong to the Applicant; these antibodies have been obtained by the same method than m18D5 and are used as control. These control antibodies are IgG2a mouse monoclonal anti-human SIRPa antibodies.

In addition, commercial antibodies were used for comparison. The first one is an anti-SIRPa antibody, named SE7C2 (Santa Cruz sc-23863); the second antibody is an antibody able to recognize both SIRP α/β and is named SE5A5 (BioLegend BLE323802); and the third one is an anti-human SIRPa antibody named Kwar23 (Creative Biolabs). An anti-human SIRPa antibody named SIRP29 from University of Toronto described in the PCT application WO2013056352 was also used for comparison.

Example 1

Binding Analyses of the Anti-SIRPa Antibodies on SIRPa by ELISA

Method: The binding activity of the anti-SIRPa antibodies was assessed by ELISA. For the ELISA assay with the chimeric antibody, the humanized antibodies, SIRP29 and Kwar23, a recombinant hSIRPa (Sino Biologicals, Beijing, China; reference 11612-H08H) was immobilized on plastic at 0.5 μg/ml in carbonate buffer (pH9.2) and the purified antibody was added to measure binding. After incubation and washing, peroxidase-labeled donkey anti-human IgG (Jackson Immunoresearch; USA; reference 709-035-149) was added and revealed by conventional methods.

For the ELISA assay with the mouse antibodies, a recombinant hSIRPa (Sino Biologicals, Beijing, China; reference 10975-H08H) was immobilized on plastic at 0.5 μg/ml in carbonate buffer (pH9.2) and the purified antibody was added to measure binding. After incubation and washing, peroxidase-labeled goat anti-mouse Fc chain (Jackson Immunoresearch; reference 115-036-071) was added and revealed by conventional methods.

Figure 1B:
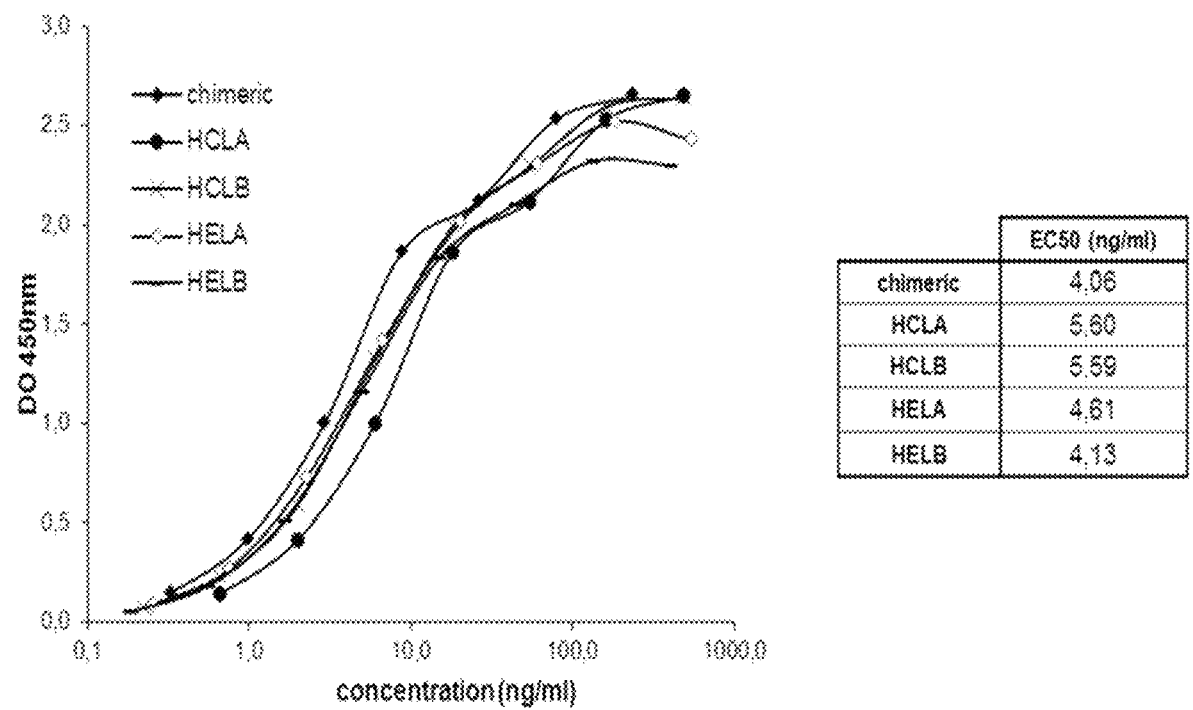
Figure 1C:
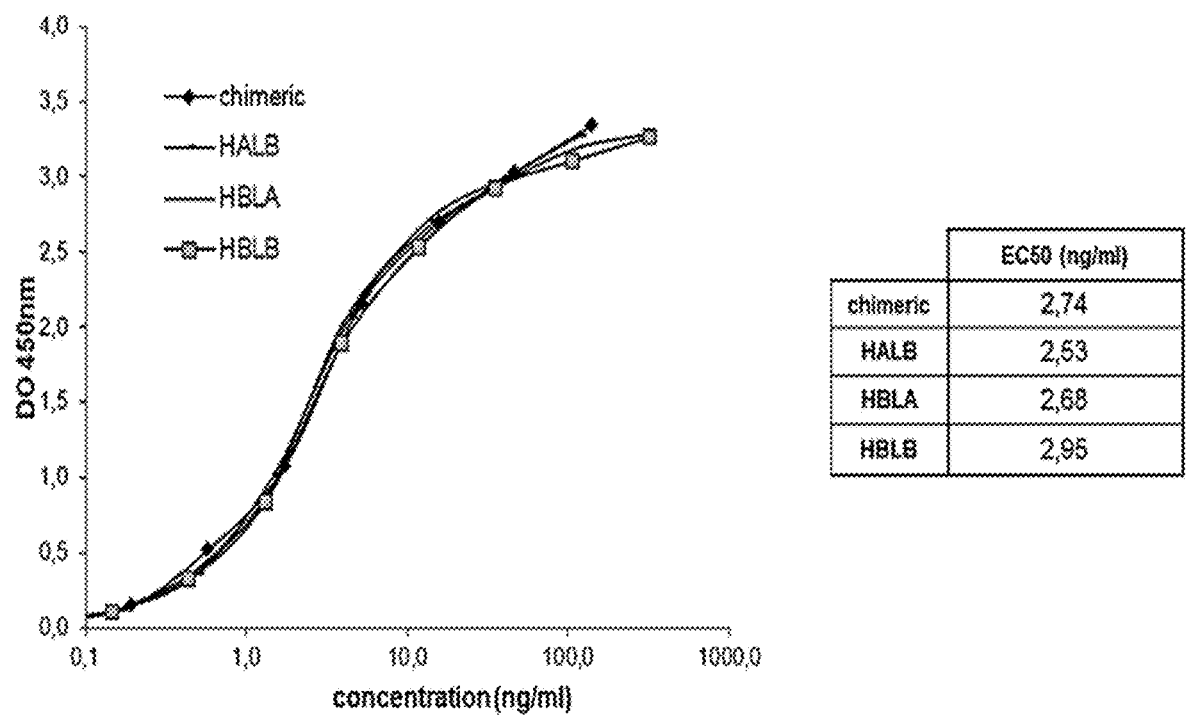

Results: As shown in FIG. 1A, 1B and 1C, the binding activity of the different anti-SIRPa antibodies on SIRPa as measured by ELISA showed effective concentrations (EC50) of 2.9 ng/ml for the chimeric antibody, 3.9 ng/ml for HALA, 5.1 ng/ml for HFLA, 4.0 ng/ml for HFLB, 7.1 ng/ml for HEFLA, 4.4 ng/ml HEFLB in a first experiment, 4.06 ng/ml for the chimeric antibody, 5.60 ng/ml for HCLA, 5.59 ng/ml for HCLB, 4.61 ng/ml for HELA, 4.13 ng/ml for HELB in a second experiment, and 2.74 ng/ml for the chimeric antibody, 2.53 ng/ml for HALB, 2.68 ng/ml for HBLA, 2.95 ng/ml for HBLB in a third experiment. Those results indicate that the antibodies of the invention tested are good SIRPa binders by ELISA as compared to other known anti-SIRPa antibodies SIRP29 (3.7 ng/ml) and Kwar23 (3.3 ng/ml). Those results indicate that the epitope recognized by all the antibodies of the invention is accessible when SIRPa is coated on a plastic well.

Figure 1D:
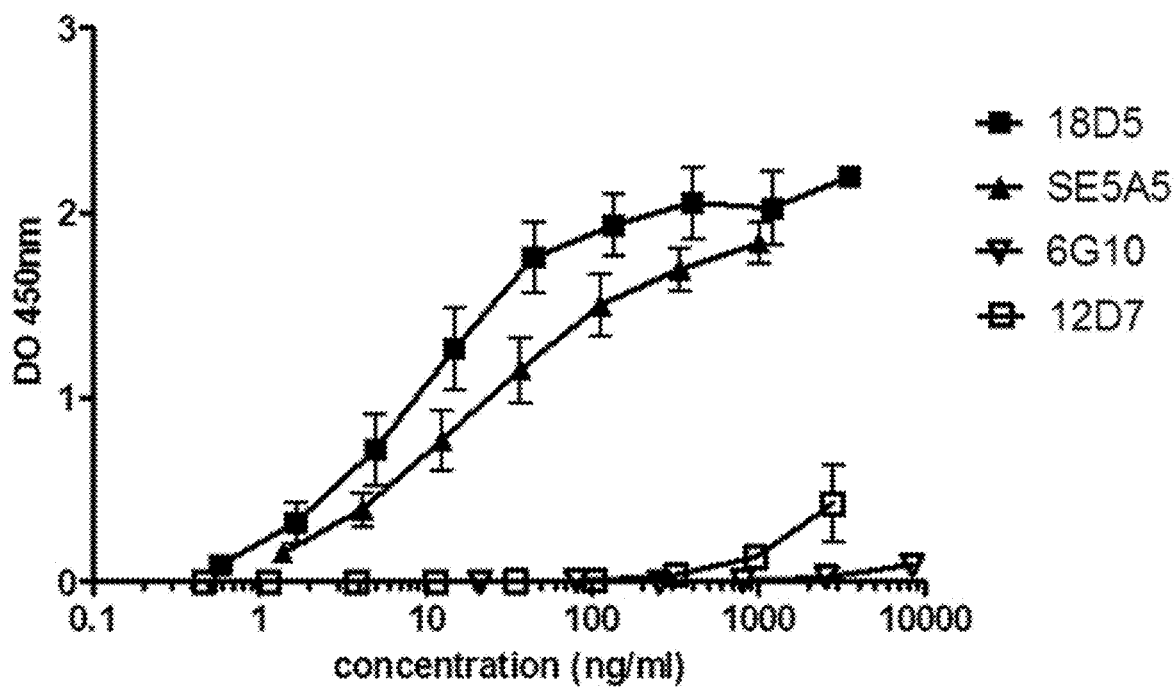

As shown in FIG. 1D, the binding activity of different anti-SIRPa antibodies on SIRPa as measured by ELISA showed an effective dose (ED50) of 0.16 nM (24 ng/ml) for SE5A5 and 0.06 nM (9 ng/ml) for the clone m18D5. The clones 6G10 and 12D7 did not seem to bind SIRPa by ELISA assay. Those results indicate that the clone m18D5 is a good SIRPa binder by ELISA compared to a commercial antibody and indicate that the epitope recognized by this clone is accessible when SIRPa is coated on a plastic well compared to clones 6G10 and 12D7.

Example 2

Biosensor Affinity Measurement of the Anti-SIRPa Antibodies for SIRPa

Method: Recombinant hSIRPa (Sino Biologicals, Beijing, China; reference 11612-H08H) was immobilized into a CM5 sensor chip (GeHealthcare; France) at 5 µg/ml (500 RU) and antibodies were applied at different concentrations with a flow rate of 40 µl/min. Analysis was performed with a BIAcore 3000 (Biacore, GeHealthcare). Values were measured after an association period (ka) of 3 min followed by a dissociation period of 10 min (kd) to determine affinity constant (KD).

Results: As shown in FIG. 2, the antibodies of the invention have a strong affinity (KD) for SIRPa (from 1.93e-10 M to 3.67e-10 M), which is equivalent to the affinity of the known anti-SIRPa antibodies SIRP29 and Kwar23 and better than the affinity of the commercial anti-SIRPa antibodies SE7C2 and SE5A5.

Example 3

SIRPa Binding Assay on Human Monocytes by Cytofluorometry

Method: To measure the binding of the anti-SIRPa antibodies on human monocytes, human Fc Receptor Binding Inhibitor (BD pharmingen; USA; reference 564220) was first added for 30 min at room-temperature to block human Fc receptors on human monocytes to reduce background. Then, an antibody was incubated for 30 min at 4° C., washed before stained 30 min at 4° C. with PE-labeled anti-human IgG Fc (Biolegend; USA; reference 409303). For the mouse antibodies, a PE-labeled anti-mouseIgG (Jackson Immunoresearch; reference 715-116-151) was used. Samples were analyzed on BD LSRII or Canto II cytofluorometer.

Results: As shown in FIG. 3, the results indicate a strong binding of the anti-SIRPa antibodies of the invention on human monocytes and a binder binding (as measured with the MFI (Median Fluorescent Intensity)) that the known anti-SIRPa antibodies Kwar23, SE7C2 and SE5A5.

Example 4

Competitive Analysis Between CD47 and the Anti-SIRPa Antibodies by Antagonist ELISA Assay Method: For competitive ELISA assay, recombinant hSIRPa (Sino Biologicals, Beijing, China; reference 11612-H08H) was immobilized on plastic at 0.5 µg/ml in carbonate buffer (pH9.2). For the chimeric antibody, the humanized antibodies, SIRP29 and Kwar23, a purified antibody (at different concentrations) was mixed with 6 µg/ml final (fix concentration) of biotinylated Human CD47Fc (AcroBiosystems interchim; France; reference: #CD7-H82F6) to measure competitive binding for 2 h at 37° C. After incubation and washing, peroxidase-labeled streptavidin (Vector laboratoring; USA; reference SA-5004) was added to detect Biotin-CD47Fc binding and revealed by conventional methods.

For the mouse antibodies, a purified antibody (at different concentrations) was mixed with 0.04 µg/ml of CD47Fc (Sino Biologicals, Beijing, China; reference 12283-H02H) to measure competitive binding for 2 h at 37° C. After incubation and washing, peroxidase-labeled donkey anti-human Fc chain (Jackson Immunoresearch; reference 709-035-149) was added to detect CD47Fc binding and revealed by conventional methods.

Figure 4B:
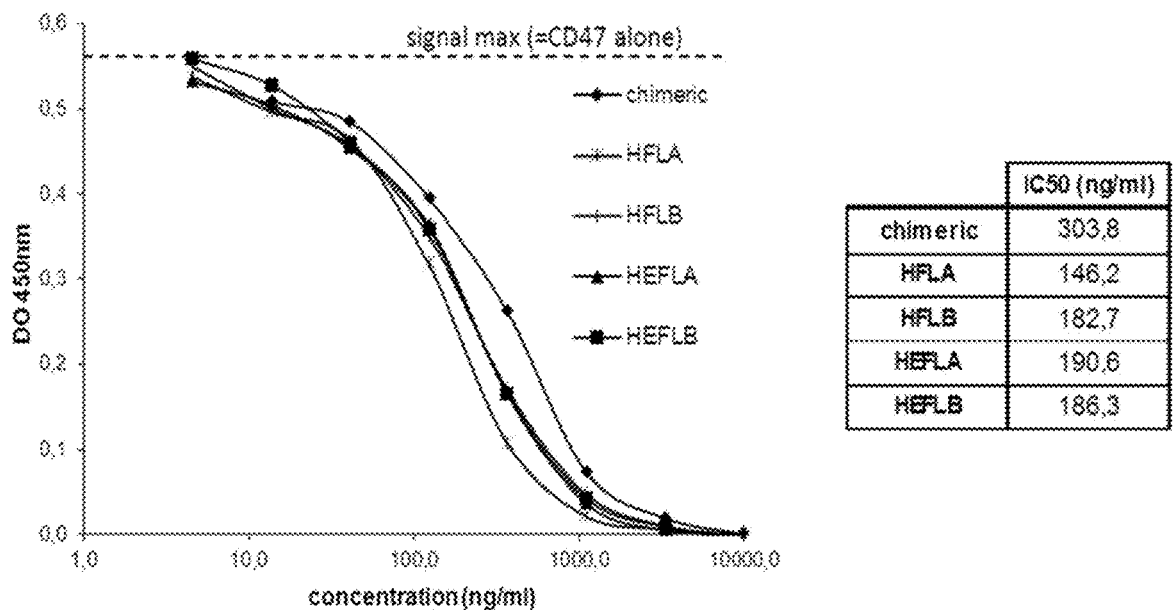
Figure 4C:
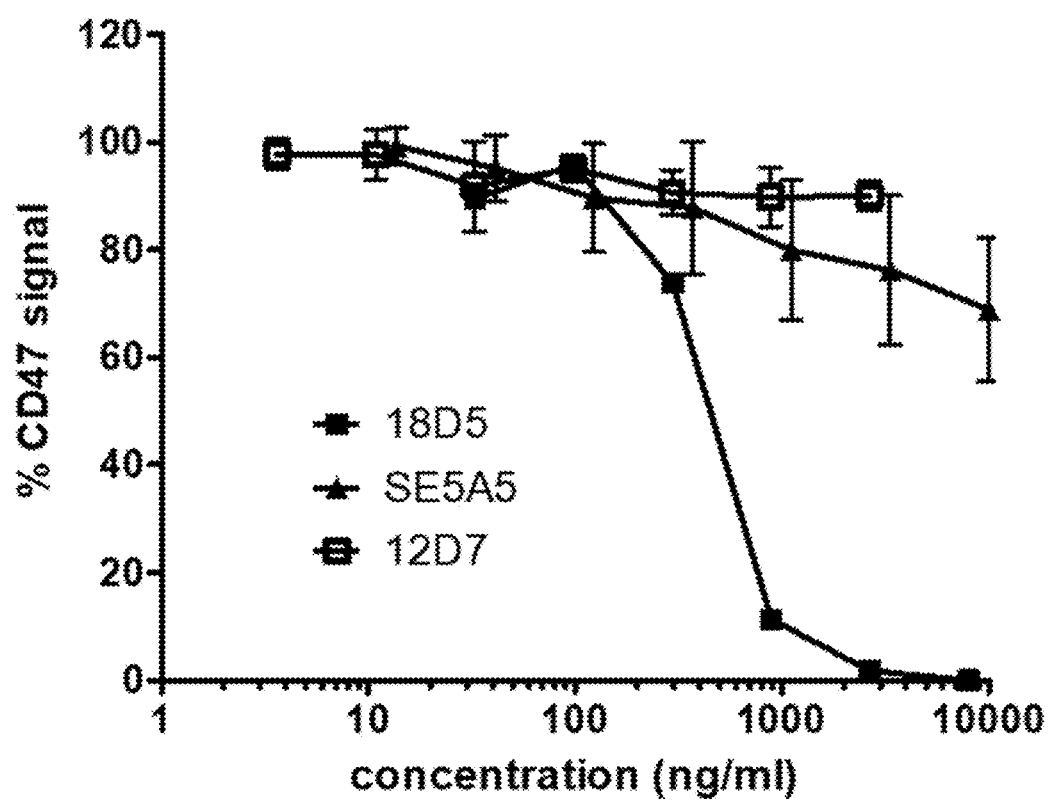

Results: As shown in FIG. 4, the antibodies of the invention have an antagonist activity on the SIRPa-CD47 interaction. In particular, it is observed that the chimeric antibody, HFLA, HFLB, HEFLA and HEFLB have a better antagonist activity as compared to the antagonist activity of SIRP29 and the commercial anti-SIRPa antibody SE5A5.

Example 5

Competitive Analysis Between CD47 and the Humanized Anti-SIRPa Antibodies on Human Monocytes by Antagonist Cytofluorometry Assay Method: To measure the competition between CD47 and the humanized anti-SIRPa antibodies on human monocytes, a purified antibody was added on monocytes for 15 min at 4° C., then mixed with 5 µg/ml final of biotinylated Human CD47Fc (AcroBiosystems interchim; France; reference: #CD7-H82F6) and incubated for 30 min at 4° C. to measure competitive binding antibody. After incubation and washing, PE-labeled streptavidin (BDBiosciences; USA; reference 554061) was added for 15 min at 4° C. to detect Biotin-CD47Fc binding and analyzed on BD LSRII or Canto II cytofluorometer.

To measure the competition between CD47 and the mouse anti-hSIRPa antibodies on human monocytes, a purified antibody was added on monocytes for 15 min at 4° C., then mixed with 5 µg/ml final of CD47Fc (Sino Biologicals, Beijing, China; reference 12283-H02H) and incubated for 15 min at 4° C. to measure competitive binding antibody. After incubation and washing, FITC-labeled anti-human Fc (Beckman Coulter; reference IM1627) was added for 15 min at 4° C. to detect CD47Fc binding and analyzed on BD LSRII or Canto II cytofluorometer.

Figure 5B:
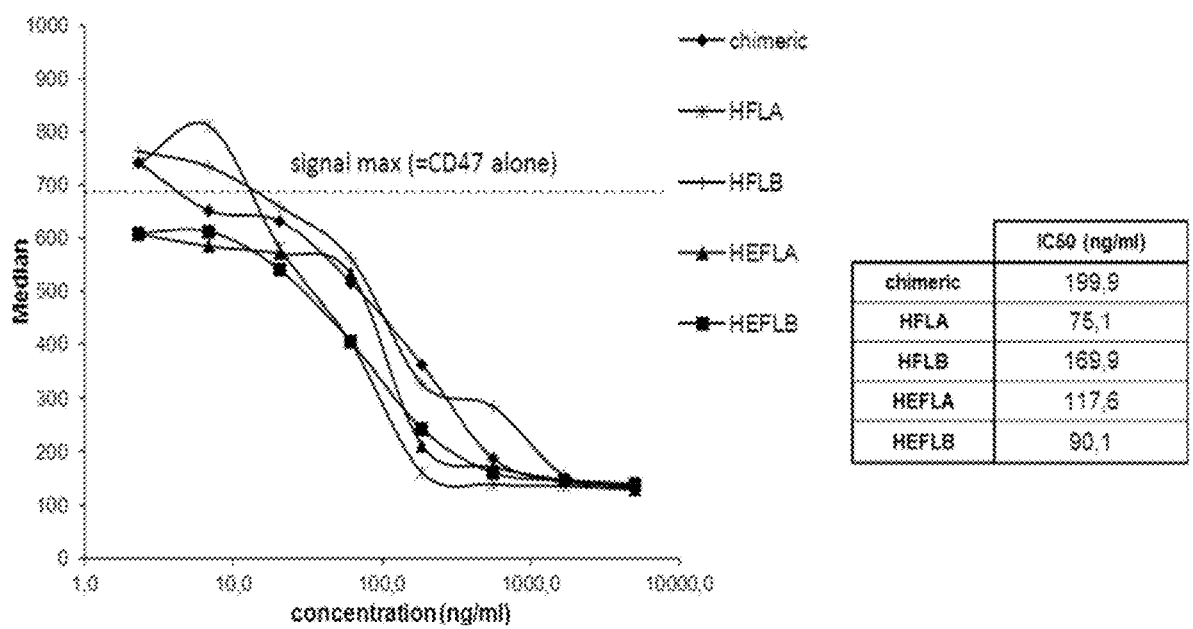
Figure 5C:
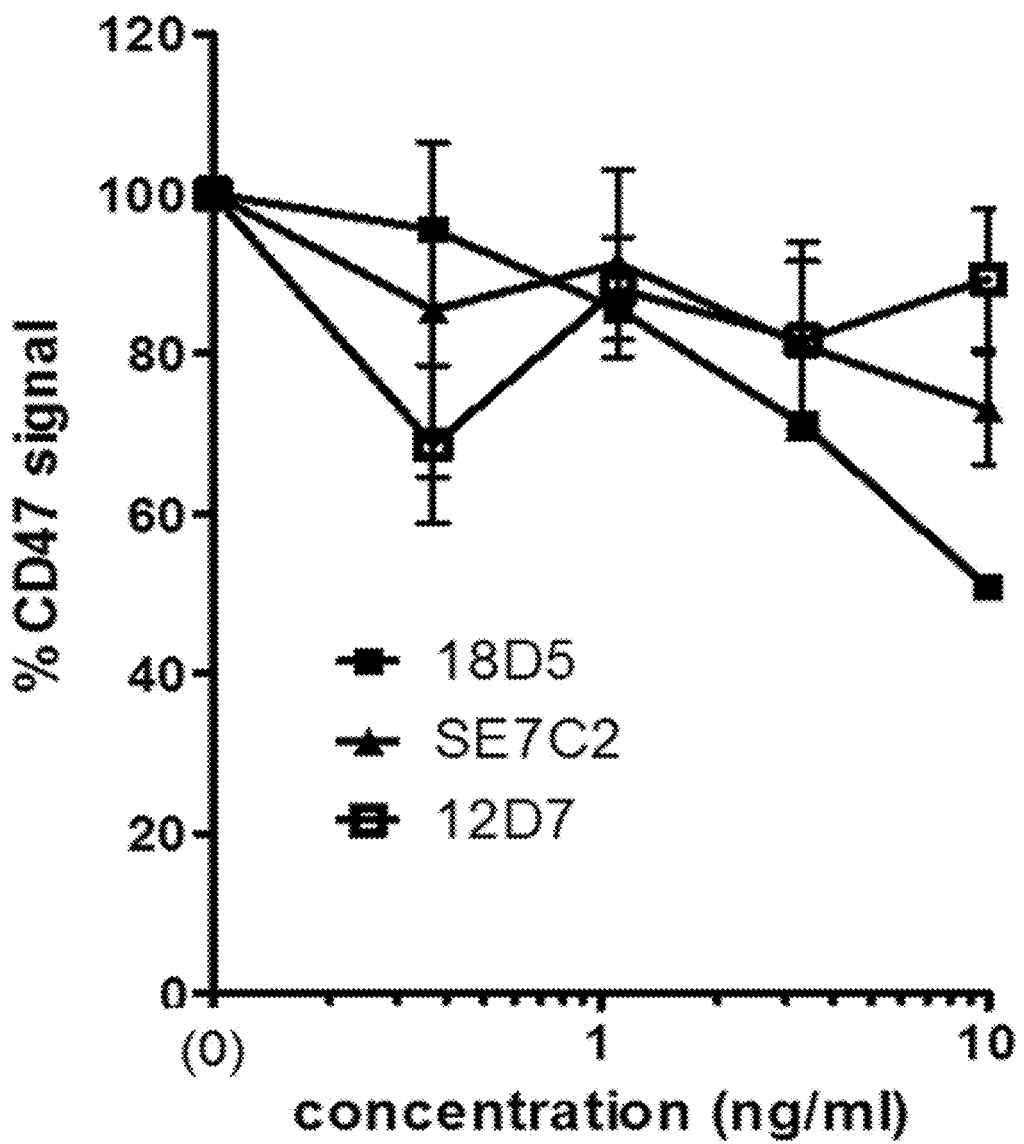

Results: As shown in FIG. 5, the antibodies of the invention have an antagonist activity on SIRPa-CD47 interaction on human monocytes.

Example 6

Blitz Method Competition with SP-D

Method: This method was performed with a Blitz (Forté Bio; USA; reference C22-2 No 61010-1).

Condition A: SIRPa+Anti-SIRPa antibody+Surfactant Protein D (SP-D). In a first step, SIRPa (His) recombinant protein (Sino Biologicals, Beijing, China; reference 11612-H08H) was immobilized at 10 µg/ml by histidine tail into a Ni-NTA biosensor (Forté Bio; USA; reference 18-0029) for 30 seconds. In a second step, anti-SIRPa antibodies were added at 20 µg/mL (saturating concentration) for 120 seconds. Then, human SP-D (R et D Systems; USA; reference 1920-SP-050) was associated at 100 µg/mL, in competition with anti-SIRPa antibodies, for 120 seconds. The dissociation of SP-D was made in kinetics buffer for 120 seconds. Analysis of data was made with the Blitz pro 1.2 software, which calculated association constant (ka) and dissociation constant (kd) and determined the affinity constant KD (ka/kd).

Condition B: SIRPa+Surfactant Protein D (SP-D)+Anti-SIRPa antibody. In a first step, Sirp-a (His) recombinant protein (Sino Biologicals, Beijing, China; reference 11612-H08H) was immobilized at 10 µg/ml by histidine tail into a Ni-NTA biosensor (Forté Bio; USA; reference 18-0029) for 30 seconds. In a second step, human SP-D (R et D Systems; USA; reference 1920-SP-050) was added at 100 µg/mL for 120 seconds. Then, anti-SIRPa antibodies were associated at 20 µg/mL (saturating concentration) for 120 seconds. The dissociation of anti-SIRPa antibody was made in kinetics buffer for 120 seconds. Analysis data was made with the Blitz pro 1.2 software, which calculated association constant (ka) and dissociation constant (kd) and determined the affinity constant KD (ka/kd).

Results: As shown in FIG. 6, the binding of the anti-SIRPa antibody 18D5 does not block the binding of SP-D to SIRPa and the binding of SP-D does not block the binding of 18D5 to SIRPa. Thus, the antibody of the invention does not inhibit the interaction between SIRPa and SP-D.

Example 7

Affinity of the Anti-SIRPa Antibodies for SIRPb by Blitz Method

Method: This method was performed with a Blitz (Forté Bio; USA; reference C22-2 No 61010-1). Recombinant hSIRPb-His (Antibodies-online; USA; reference ABIN3077231) was immobilized at 10 µg/ml by histidine tail into a Ni-NTA biosensor (Forté Bio; USA; reference 18-0029) for 30 seconds. Then, an anti-SIRPa antibody was associated at 20 µg/mL for 120 seconds. The dissociation of anti-SIRPa antibody was made in kinetics buffer for 120 seconds. Analysis of data was made with the Blitz pro 1.2 software, which calculated association constant (ka) and dissociation constant (kd) and determined the affinity constant KD (ka/kd).

Results: As shown in FIG. 7A, the antibodies of the invention have a lower affinity for SIRPb as compared to SIRPa. In particular, it is noted that the chimeric antibody, HFLA, HFLB, HEFLA, HEFLB have a reduced affinity for SIRPb as compared to SIRP29 and Kwar23.

Example 8

ELISA Binding of Anti-SIRP Antibodies on SIRPb

Method: For activity ELISA assay, recombinant hSIRPb-His (Antibodies-online; USA; reference ABIN1466557) was immobilized on plastic at 1 µg/ml in carbonate buffer (pH9.2) and a purified antibody was added to measure binding. After incubation and washing, peroxidase-labeled donkey anti-human IgG (Jackson Immunoresearch; USA; reference 709-035-149) was added and revealed by conventional methods.

Results: As shown in FIG. 7B, the anti-SIRPa antibodies have a low affinity for SIRPb. It must be indicated that the revelation was performed with a donkey anti-human antibody for all antibodies except for B4B6 (revealed with a mouse antibody), which may explain that the signal obtained for the anti-SIRPb antibody B4B6 is lower than the signal obtained for the anti-SIRPa antibodies.

Example 9

Affinity Analysis of the Anti-SIRPa Antibodies for SIRPg by Blitz Method

Method: This method was performed with a Blitz (Forté Bio; USA; reference C22-2 No 61010-1). Recombinant hSIRPg-His (Sino Biologicals, Beijing, China; reference 11828-H08H) was immobilized at 10 µg/ml by histidine tail into a Ni-NTA biosensor (Forté Bio; USA; reference 18-0029) for 30 seconds. Then, an anti-SIRPa antibody was associated at 20 µg/mL for 120 seconds. The dissociation of anti-SIRPa antibody was made in kinetics buffer for 120 seconds. Analysis of data was made with the Blitz pro 1.2 software, which calculated association constant (ka) and dissociation constant (kd) and determined the affinity constant KD (ka/kd).

Results: As shown in FIG. 8A, the anti-SIRPa antibodies of the invention have a low affinity for SIRPg. This affinity is slightly weaker than the affinity of the known anti-SIRPa antibodies SIRP29 and Kwar23. However, the kinetics properties differ between anti-SIRPa antibodies, SIRP29 and Kwar23, with a high dissociation rate constant (Kd) for anti-SIRPa antibodies as compared to SIRP29 and Kwar23. In particular, HFLB has the lowest affinity for SIRPg with a KD value of 1.036e-7 M that equals to a 2-log difference as compared to the KD values of SIRP29 and Kwar23.

Example 10

ELISA Binding of the Anti-SIRP Antibodies on SIRPg

Method: For activity ELISA assay, hSIRPg-His (Sino Biologicals, Beijing, China; reference 11828-H08H) was immobilized on plastic at 1 µg/ml in carbonate buffer (pH9.2) and purified antibody were added to measure binding. After incubation and washing, peroxidase-labeled donkey anti-human IgG (Jackson Immunoresearch; USA; reference 709-035-149) was added and revealed by conventional methods.

Results: As shown in FIG. 8B, the anti-SIRPa antibody HEFLB does not bind SIRPg while the known anti-SIRPa antibodies SIRP29 and Kwar23 show a significant binding to SIRPg.

Example 11

Blitz Method Competition with CD47 for SIRPg: SIRPg+Anti-SIRPa Antibody+CD47

Method: This method was performed with a Blitz (Forté Bio; USA; reference C22-2 No 61010-1). In a first step, hSIRPg-His (Sino Biologicals, Beijing, China; reference 11828-H08H) was immobilized at 10 µg/ml by histidine tail into a Ni-NTA biosensor (Forté Bio; USA; reference 18-0029) for 30 seconds. In a second step, an anti-SIRPa antibody was added at 20 µg/mL (saturating concentration) for 120 seconds. Then, human CD47Fc ((Sino Biologicals, Beijing, China; reference 12283-H02H) was associated at 100 µg/mL, in competition with anti-SIRPa antibodies, for 120 seconds. The dissociation of CD47Fc was made in kinetics buffer for 120 seconds. Analysis data was made with the Blitz pro 1.2 software, which calculated association constant (ka) and dissociation constant (kd) and determined the affinity constant KD (ka/kd).

Results: As shown in FIG. 9, the anti-SIRPa HEFLB of the invention does not compete with the binding of CD47 to SIRPg. At the opposite, the other known antibodies SIRP29 and, in particular, kwar23 compete with the binding of CD47 to SIRPg.

Example 12

Binding to Blood Cells by Flow Cytometry

Method: The experiment was realized to analyze the binding of the anti-SIRPa antibodies on human blood cells. CD3-positive T lymphocytes, red blood cells and platelets were extracted from purified blood from healthy volunteers. Cells were then stained for 30 min at 4° C. with 10 micrograms/ml of each tested antibody, washed and then stained with a secondary fluorescent anti-IgG antibody for another 30 min at 4° C. After washes, cells were analyzed on a CANTO II (BD Bioscience) flow cytometer.

Figure 10B:
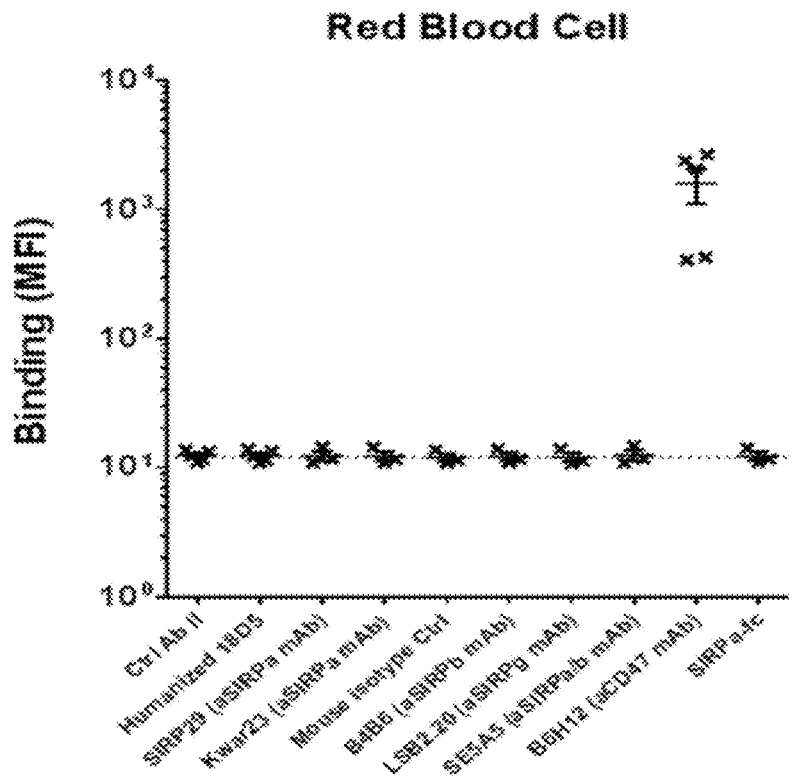
Figure 10C:
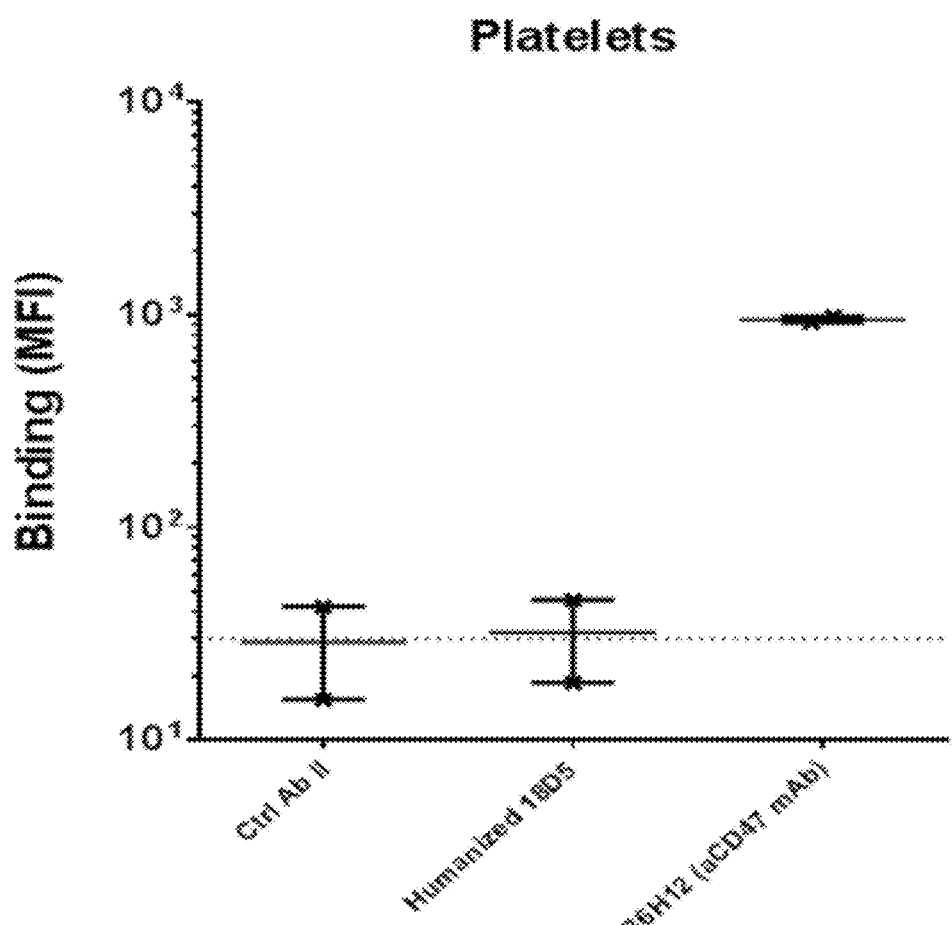

Results: As shown in FIG. 10, the T cells, the red blood cells and the platelets are positive for CD47, which is expressed ubiquitously, and they were stained with the B6H12 antibody. The SIRP29 and the Kwar23 antibodies, like LSB2.20 (specific anti-SIRPγ antibody), bind to T cells that are known to express SIRPγ. However, the anti-SIRPa humanized 18D5 antibody does not bind to the T cells (same results obtained with four different 18D5 humanized variants tested). Red blood cells and platelets do not express SIRPa and, thus, they were not revealed with the humanized 18D5 antibody and the other anti-SIRPa antibodies. This result shows the specificity of the humanized 18D5 antibody for SIRPa on live cells as compared to the known anti-SIRPa antibodies.

As shown in FIG. 11, the T-cells are not stained by the humanized 18D5 antibody (same results obtained with five different 18D5 humanized variants tested) and with the chimeric 18D5 (data not shown) whereas more than 70% of T cells are stained by SIRP29 and Kwar23.

Example 13

Human CD3+ T Cell Proliferation

Method: hPBMC were isolated from buffy coat of healthy volunteers. CD4 or CD8 T cells were selected by positive selection using an AutoMACS (Miltenyi) and plated in 96-round well plate (50 000 cells/well). The proliferative signals were provided by either anti-CD3/anti-CD28 coated microbeads (LifeTechnologies) at a 1 bead for 1 T cell ratio during three days, or allogeneic mature dendritic cells generated in vitro at a 5 T cell for 1 mDC during 5 days or with different concentrations of tuberculin unpurified protein derivative (PPD) for 5 days. Antibodies targeting the SIRPa/CD47 pathway were added from the beginning of the proliferation test at a saturating concentration (10 μg/mL). Proliferation was measured by incorporation of $H^3$-thymidine during the last 12 h of culture.

Results: As shown in FIG. 12, the anti-SIRPa antibody HALA and HEFLB variants do not inhibit the T cell proliferation when T cells are stimulated with anti-CD3+anti-CD28 beads (A) (C) or with allogenic dendritic cells (B) (D) or with PPD (E), whereas the anti-SIRPa Kwar23 inhibits T cell proliferation when T cells are stimulated with allogenic dendritic cells. As expected, the anti-CD47 antibodies and the anti-SIRPg antibody are inhibitors of the T cell proliferation.

Example 14

Mouse CD8+ T Cell Proliferation

Method: Splenocytes were isolated from naïve mice. CD8 T cells were selected by positive selection using an AutoMACS (Miltenyi) and plated in 96-round well plate (50 000 cells/well). The proliferative signals were provided by anti-CD3/anti-CD28 coated microbeads (LifeTechnologies) at a 1 bead for 1 T cell ratio during three days. A mouse anti-SIRPa antibody (P84) and an anti-CD47 antibody (MIAP310) targeting the SIRPa/CD47 pathway were added from the beginning of the proliferation test at a saturating concentration (10 μg/mL). Proliferation was measured by incorporation of $H^3$-thymidine during the last 12 h of culture.

Results: As shown in FIG. 13, there is no inhibition of the anti-SIRPa or anti-CD47 antibody on the proliferation of mouse T cells. This result is explained by the fact that mice does not express the SIRPg gene. Thus, mice can be used as a model to predict the in vivo effects of a specific anti-SIRPa antibody that does not bind SIRPg. In contrast, anti-CD47 or non-selective anti-SIRPa antibodies in vivo preclinical efficacy, in particular on adaptive immunity and generation of memory T lymphocytes, is not predictive of human situation.

Example 15

Human T Cell Proliferation

Method: hPBMC were isolated from buffy coat of healthy volunteers. CD4 or CD8 T cells were selected by positive selection using an AutoMACS (Miltenyi) and plated in 96-round well plate (50 000 cells/well). The proliferative signals were provided by either anti-CD3/anti-CD28 coated microbeads (LifeTechnologies) at a 1 bead for 1 T cell ratio during three days, or allogeneic mature dendritic cells generated in vitro at a 5 T cell for 1 mDC during 5 days. Antibodies were added from the beginning of the proliferation test at a saturating concentration (5 μg/mL for anti-CD47 and anti-SIRPa antibodies and 2.5 μg/mL for the anti-PD-1/PD-L1 antibodies and the recombinant 4-1BBL). Proliferation was measured by incorporation of $H^3$-thymidine during the last 12 h of culture.

Figure 14B:
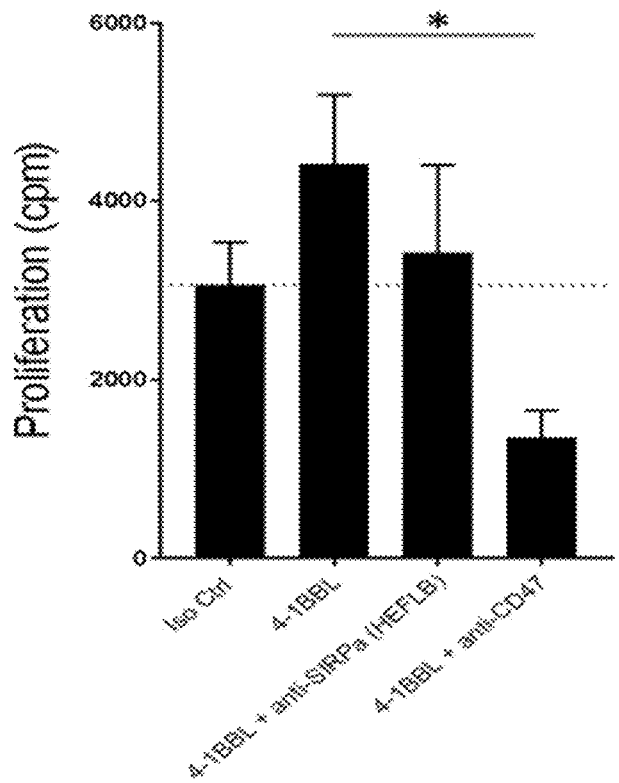

Results: As shown in FIG. 14, the anti-PD-1/PD-L1 antibodies and the recombinant 4-1BBL have a boost effect on the proliferation of human T cells, while anti-CD47 has a negative effect on the proliferation of human T cells. In particular, the anti-CD47 antibody prevents the human T-cell immunostimulatory efficacy of anti-PD-1/PD-L1 or 4-1BB agonist agents. The anti-SIRPa HEFLB has no significant effect on the proliferation of T cells.

Example 16

Anti-Tumor Effects in Mice

Method: Mice were anesthetized with a cocktail of xylazine/ketamine. After a laparotomy, tumoral Hepa 1.6 cells were injected through the portal vein ($2.5.10^6$ cells/100 μL) in PBS. The treatment was started 4 days after tumor injection. The agonistic anti-4-1BB monoclonal antibody (3H3) was injected two times at d4 and d8 after Hepa 1.6 cells (Hepatocarninoma cells, HCC) injection intraperitoneally in PBS (100 μg/injection). The anti-PDL1 monoclonal antibody was injected twice a week during 4 weeks intraperitoneally in PBS (200 μg/injection). The antagonistic anti-SIRPa antibody (P84) was injected three time a week during four weeks intraperitoneally in PBS (300 μg/injection).

The anti-tumor response was evaluated in the orthotopic model of HCC thirteen days after the tumor inoculation. At this time, the tumor and the spleen were collected in order to phenotype the immune cells that infiltrated the tumor or in the systemic way. Splenocytes and non-parenchymal cells (NPC) of the liver which are the infiltrating immune cells were stained with four different mixes for flow cytometry acquisition.

Results: As shown in FIG. 15A, the anti-SIRPa antibody alone significantly prolongs survival in a fraction of mice (28%). In combination with anti-4-1BB or anti-PDL1 antibodies, anti-SIRPa antibody allows a very high response rate of mice surviving even after treatment withdrawal.

Figure 15B:
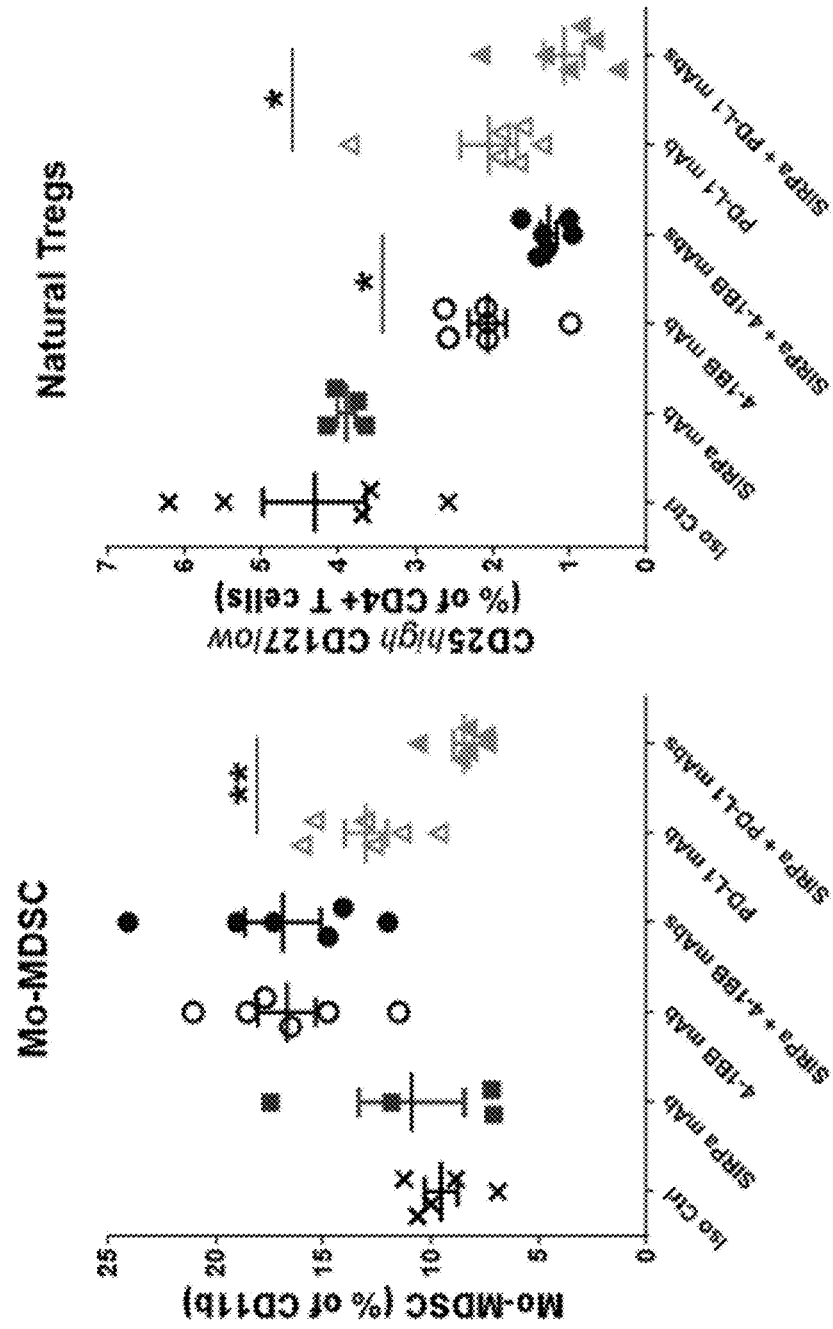
Figure 15B:
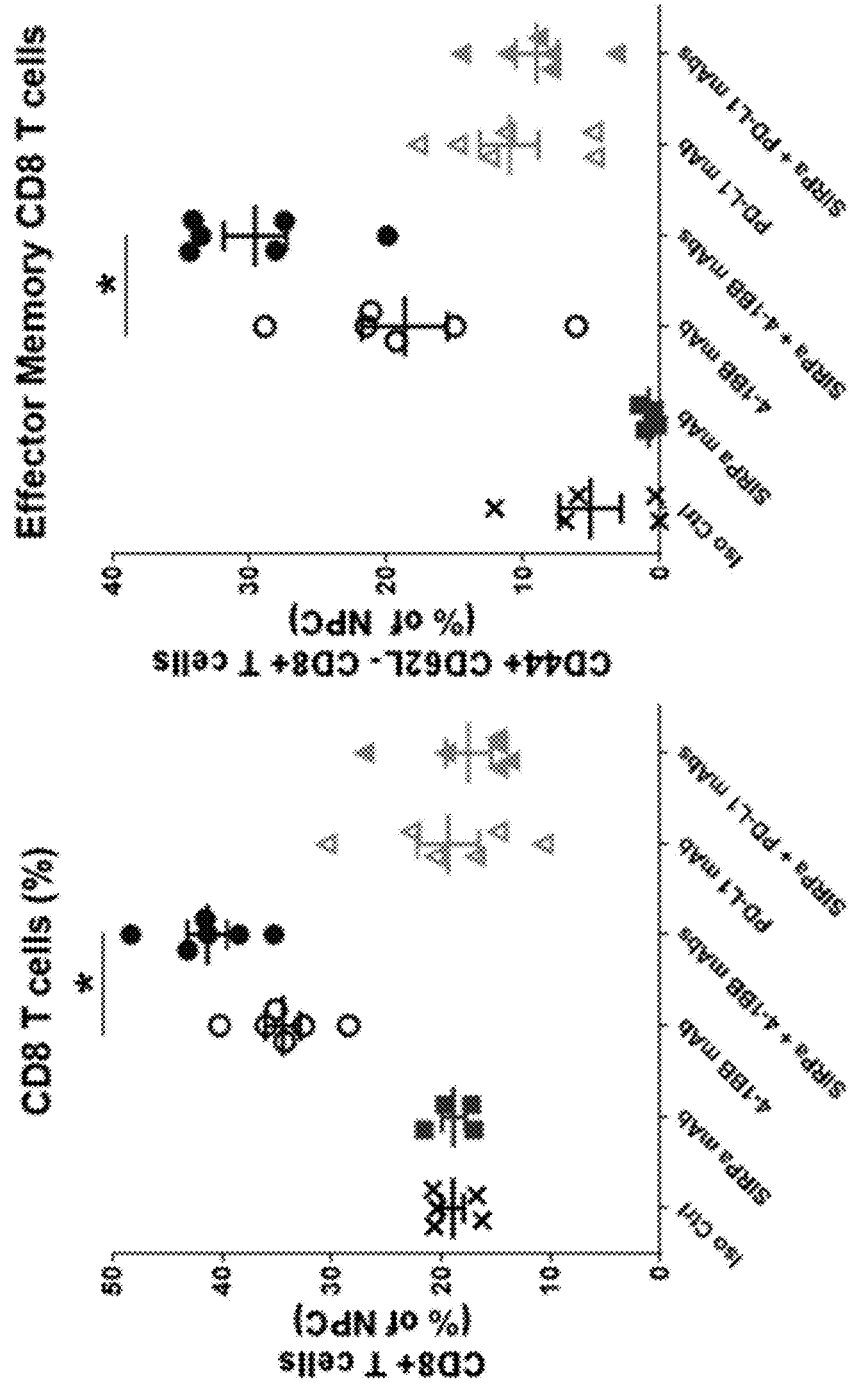

As shown in FIG. 15B, the combination of anti-SIRPa with a co-stimulatory agent (e.g. anti-4-1BB) or T-cell checkpoint inhibitor (e.g. anti-PDL1) modifies the tumor microenvironment by decreasing the regulatory and immunosuppressive immune cells (Tregs, Mo-MDSC) while increasing accumulation of effector memory CD8+ T cells in combination with anti-4-1BB. The Mo-MDSC are characterized by a high expression of Ly6C and no Ly6G among the CD11b positive- and MHC class II negative-population.

Figure 15C:
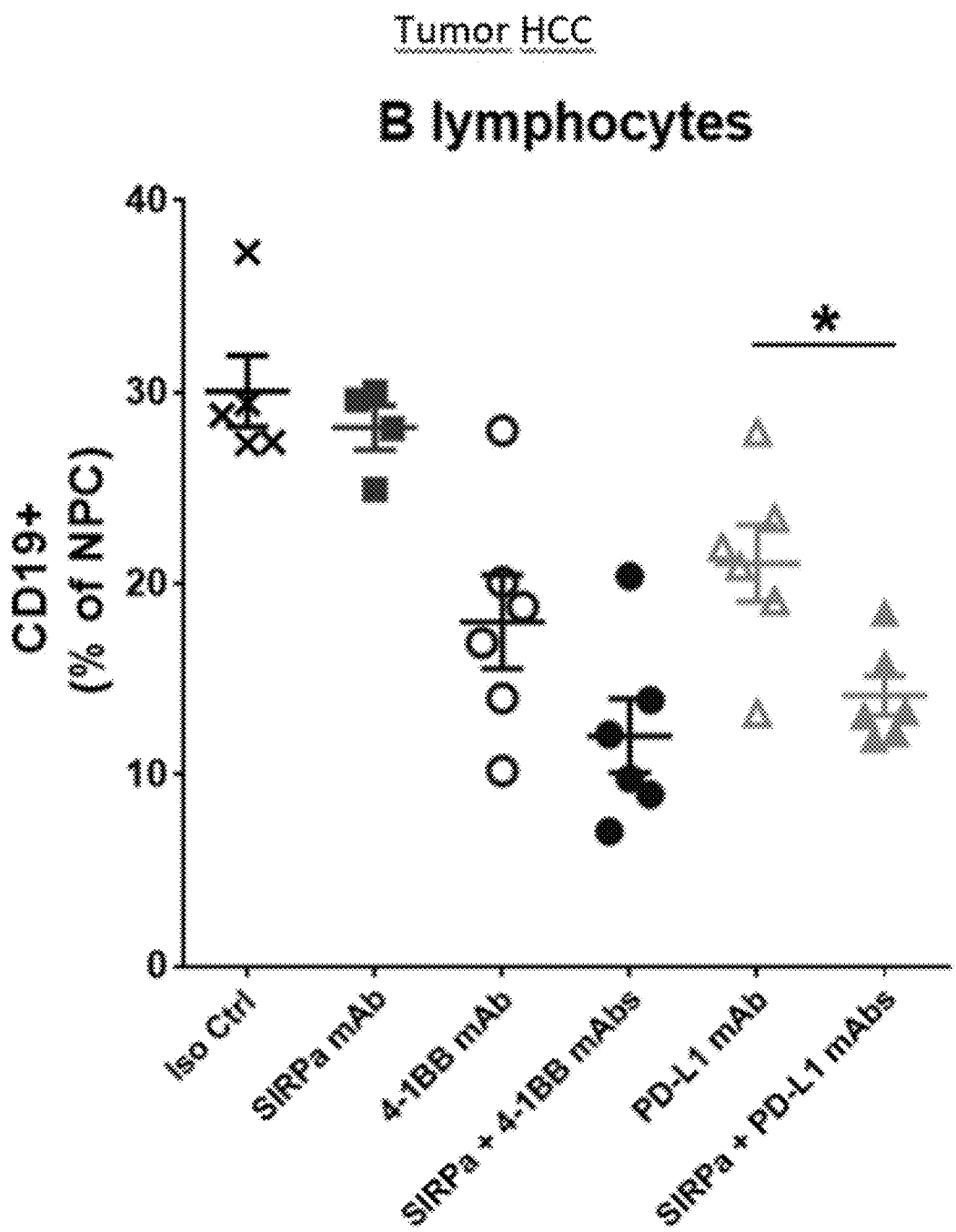
Figure 15C:
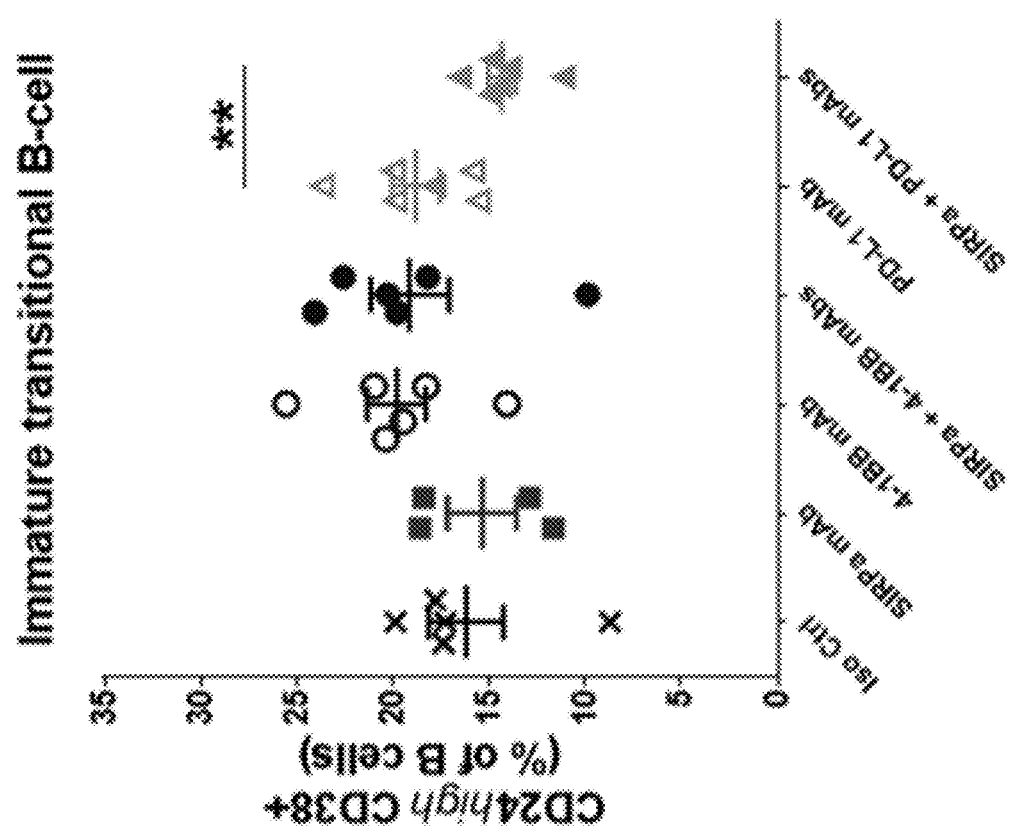
Figure 15C:
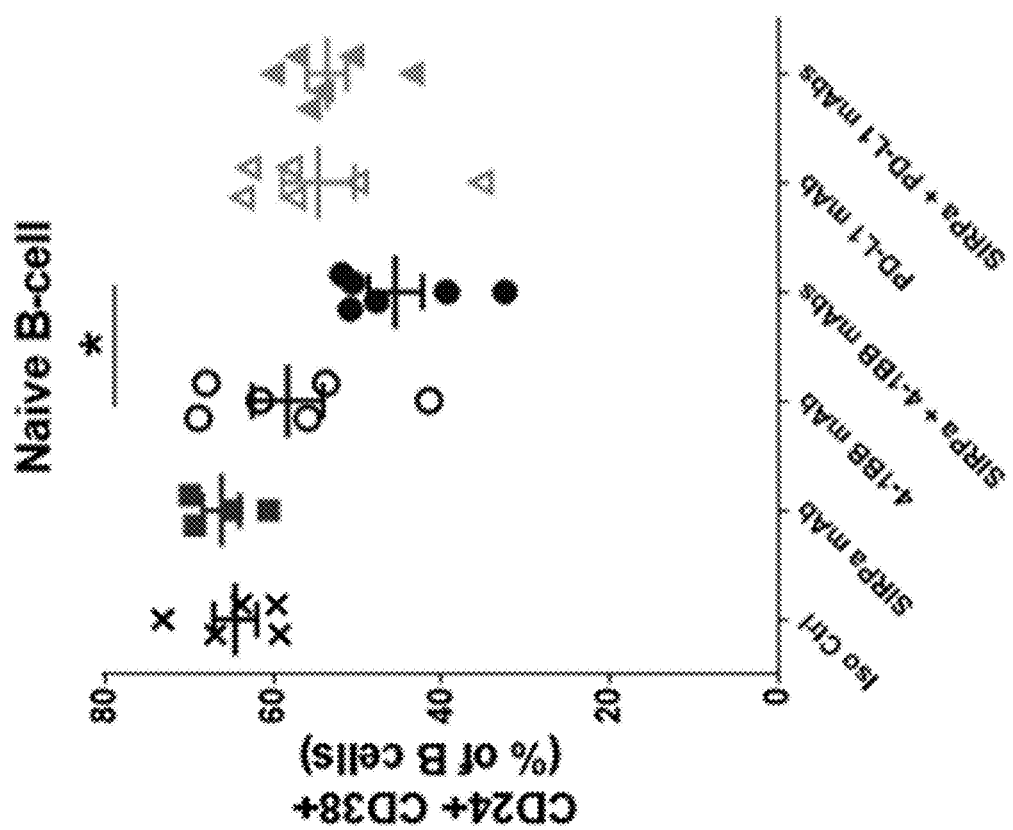
Figure 15C:
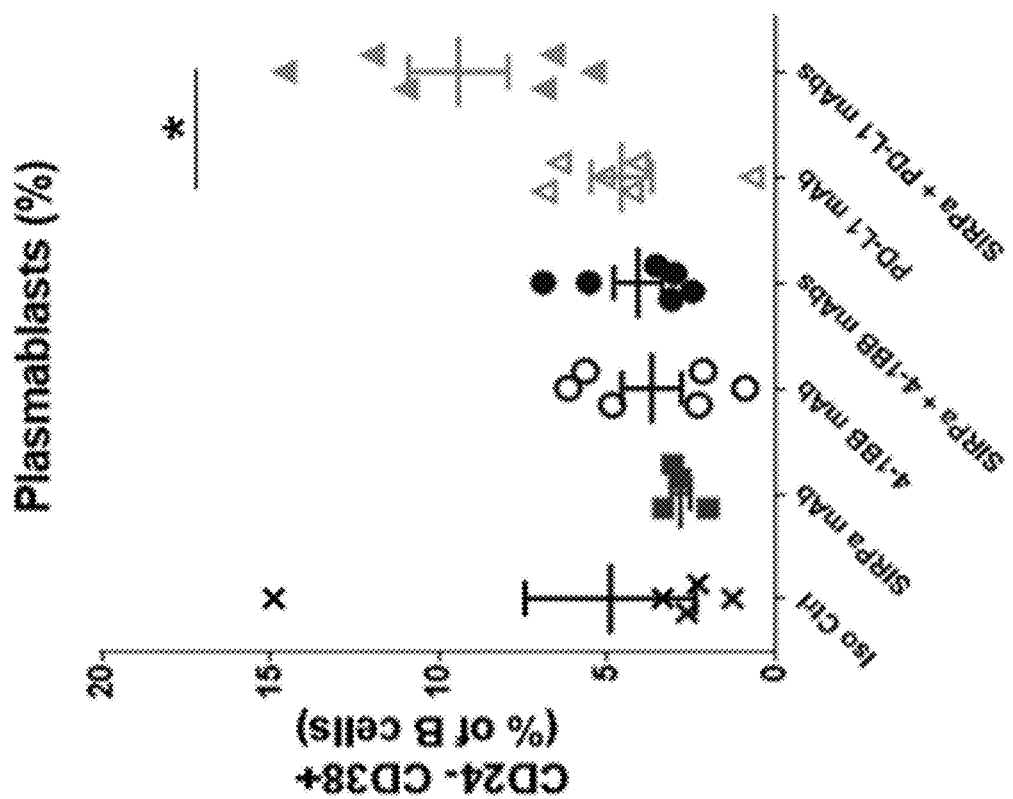
Figure 15C:
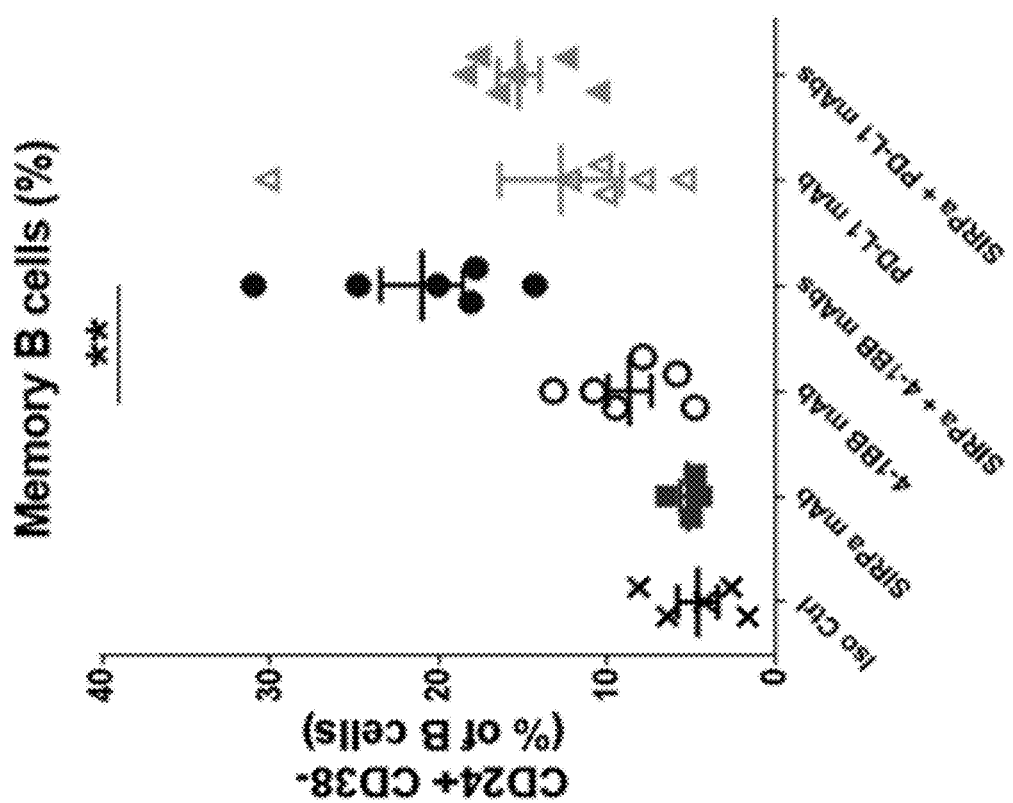
Figure 15C:
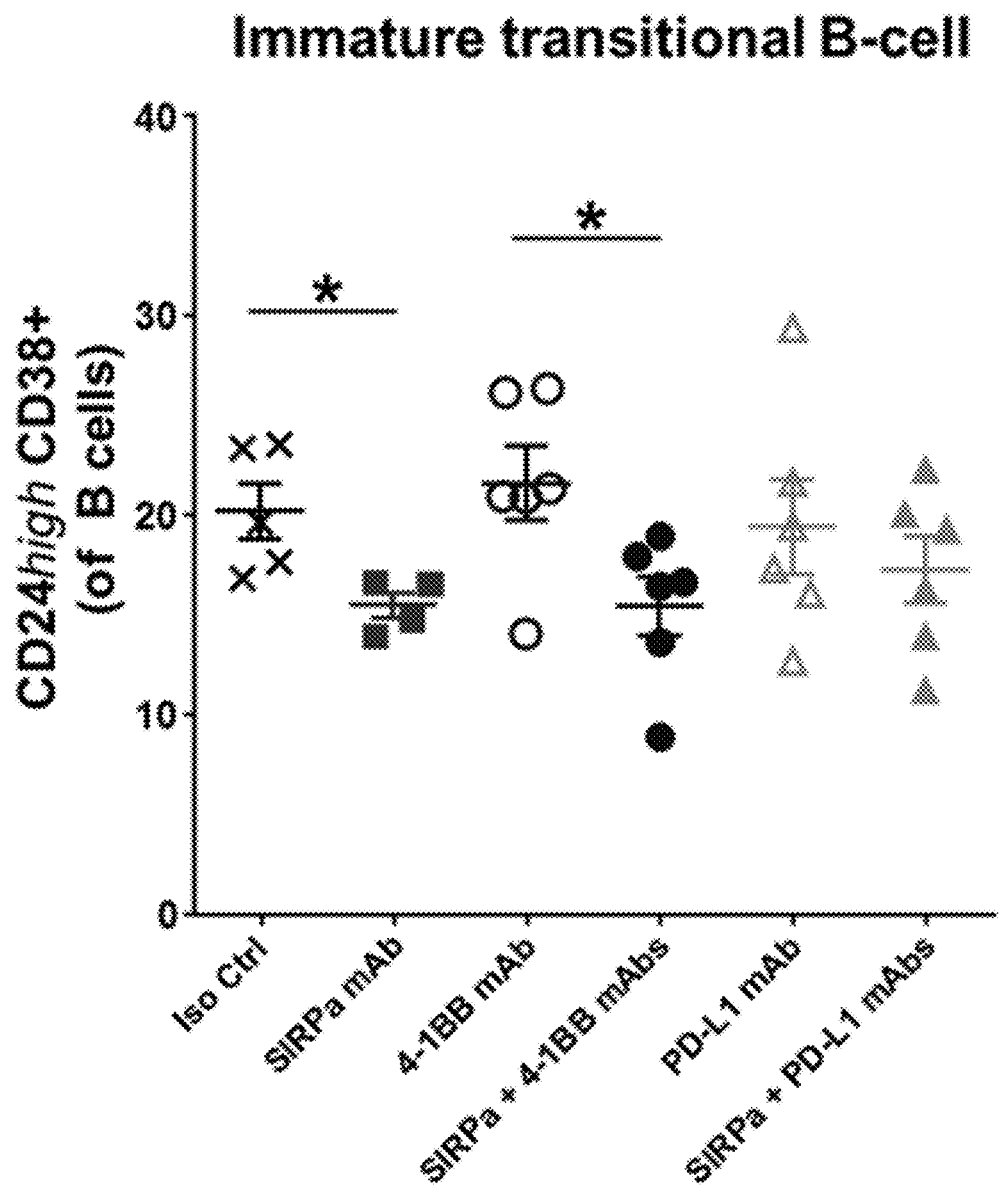
Figure 15C:
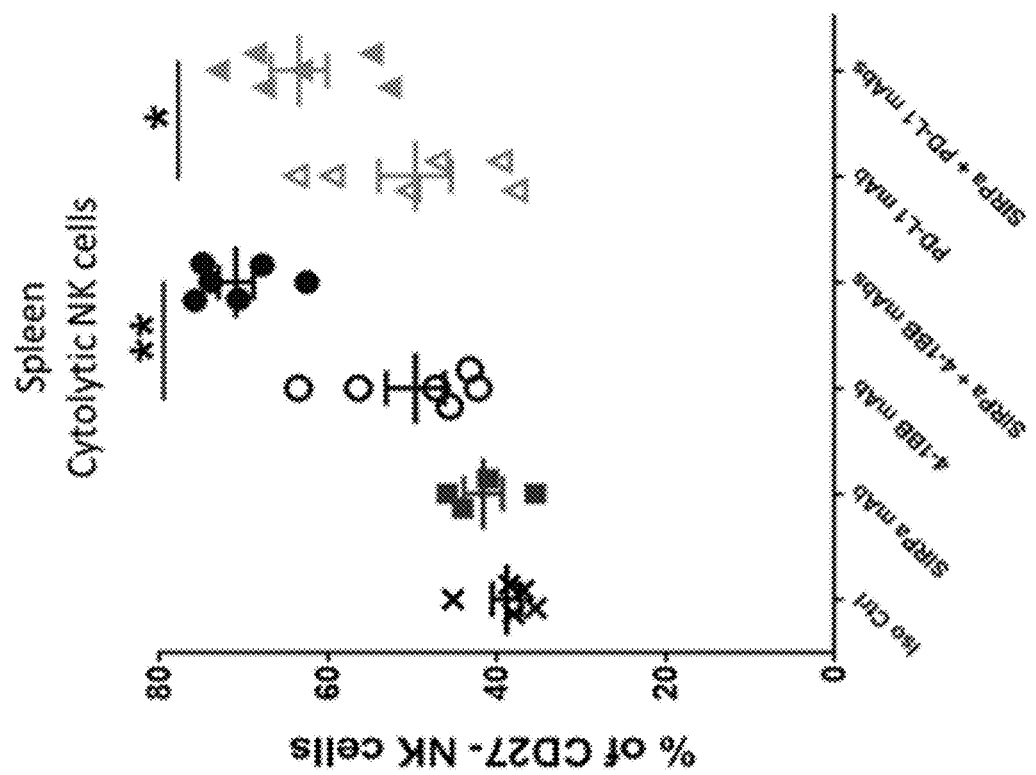
Figure 15C:
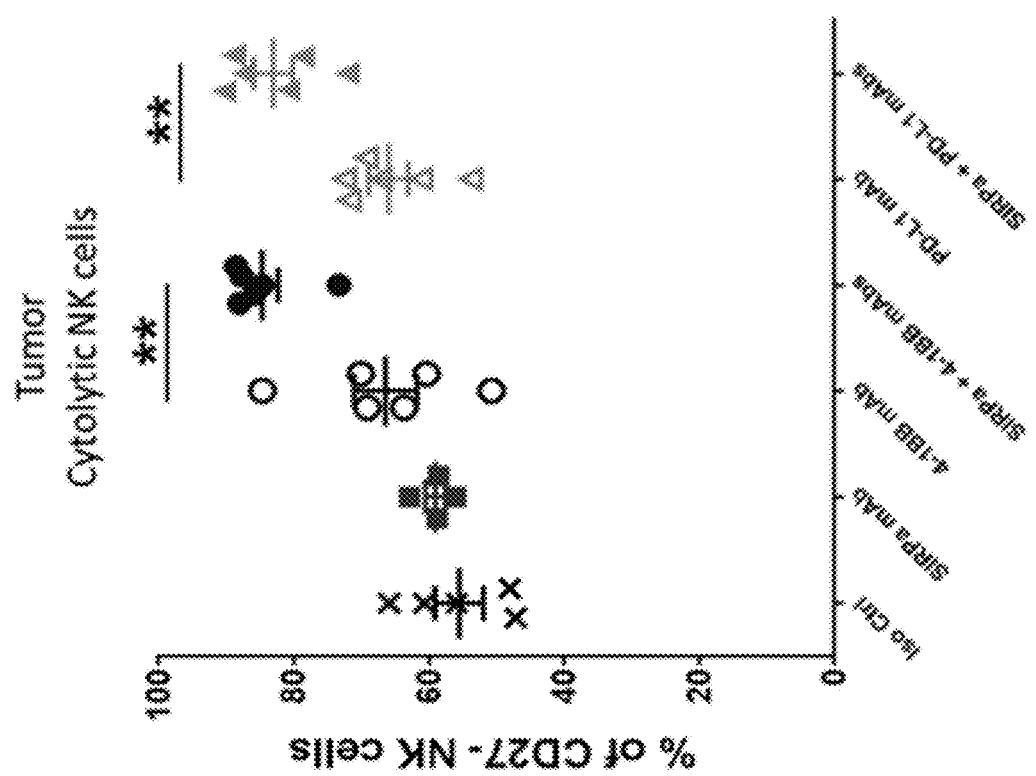

As shown in FIG. 15C, the combination of anti-SIRPa with a co-stimulatory agent (e.g. anti-4-1BB) or T-cell checkpoint inhibitor (e.g. anti-PDL1) modifies the cell composition of the tumor microenvironment and in periphery in the spleen, by decreasing the frequency of immature and naïve B cells while increasing accumulation of memory and plasmablast cells. Similarly, accumulation of cytolytic (CD27-negative) NK cells is induced the tumor and periphery by the anti-SIRPa combination with anti-41BB or anti-PDL1.

Altogether, anti-SIRPa modifies the tumor and peripheral immunity in particular adaptive (T-cell, Tregs, B-cells) and innate (MDSC, Macrophages, NK cells) immune cells contributing to tumor elimination and long-term protection.

Example 17

Anti-Tumor Effects in Mice Previously Cured

Method: Mice previously cured in the hepatoma model by anti-SIRPa+anti-4-1BB injection or SIRPa mutant mice treated with anti-4-1BB were rechallenged by Hepa 1.6 cells injection in the spleen (2.5.10^6 cells/mouse). Mice were anesthetized with 3% of isoflurane in the air. After incision on the flank of the mice and isolation of the spleen, tumoral Hepa 1.6 cells were injected into the spleen (2.5.10$^6$ cells/50 µL) in PBS. Naive mice were injected in parallel in the same route in order to compare tumor development with rechallenged mice.

Figure 15D:
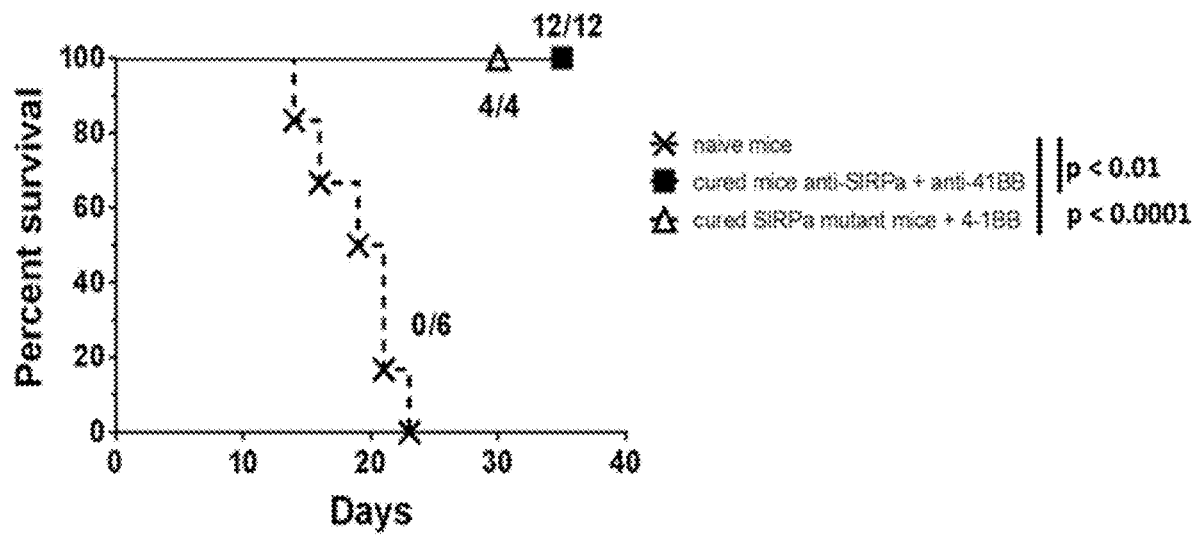

Results: As shown in FIG. 15D, all the cured mice survived when rechallenged and, at the opposite, all naïve mice died. This result demonstrates that memory T cells were induced under anti-SIRPa therapy or absence of SIRPa signals (SIRPa mutant mice) and still persist on the long-term in cured mice.

Example 18

Anti-Tumor Effects of T-Cell Splenocytes or Whole Splenocytes Collected from Mice Previously Cured Method: Cured anti-SIRPa+anti-4-1BB rechallenged mice were euthanized and the spleen was collected. After red blood cell lysis, splenocytes were extracted and CD3 positive T cells were isolated from a part of splenocytes with an AutoMACS. After anesthesia, mice were injected with either T-cell splenocytes (2.5.10$^6$ cells/100 µL) or whole splenocytes (10.10$^6$ cells/100 µL) or excipient alone (PBS) intravenously. All mice received Hepa 1.6 cells through the portal vein as described previously (2.5.10$^6$ cells/100 µL).

Figure 15E:
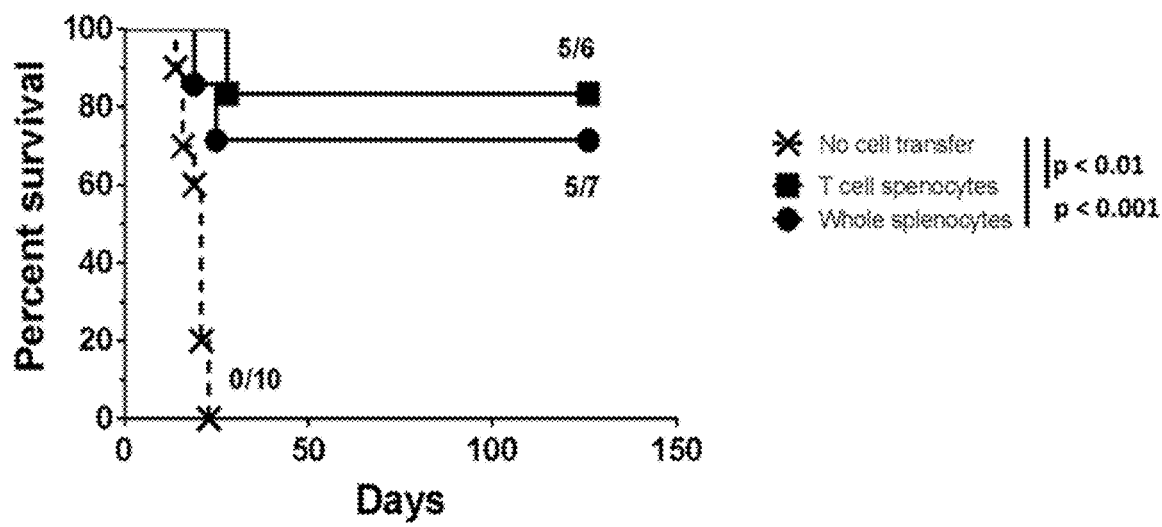

Results: As shown in FIG. 15E, the splenocytes and isolated T lymphocytes collected from cured mices has a high positive effect on the survival of mice. This results indicate that memory T cells are present in the splenocytes of the cured mice after treatment of the hepatoma and are responsible on the long-term adaptive immune memory.

Example 19

Anti-Tumor Effects in Mice Previously Cured

Method: Mice previously cured in the hepatoma model by anti-SIRPa+anti-PDL-1 injection were rechallenged by Hepa 1.6 cells injection in the spleen (2.5.10^6 cells/mouse). Mice were anesthetized with 3% of isoflurane in the air. After incision on the flank of the mice and isolation of the spleen, tumoral Hepa 1.6 cells were injected into the spleen (2.5.10$^6$ cells/50 µL) in PBS. Naive mice were injected in parallel in the same route in order to compare tumor development with rechallenged mice.

Results: As shown in FIG. 16, all the cured mice survived when rechallenged and, at the opposite, all naïve mice died. This result suggests that memory T cells are still present in cured mice. This result demonstrates that memory T cells were induced under anti-SIRPa therapy and still persist on the long-term in cured mice.

Example 20

Effects of the Growth of a Tumor in a Mammary Carcinoma Model

Method: Mice were anesthetized with 3% of isoflurane in the air. Mice were shaved on the abdomen and 4T1 cells were injected in the mammary gland with an insulinic syringe (30 Gauges) in 50 µL of PBS. The antagonistic anti-SIRPa antibody (P84) or a control antibody was injected three time a week during four weeks intraperitoneally in PBS (200 µg/injection).

Results: As shown in FIG. 17, the anti-SIRPa antibody significantly ($p<0.01$) reduces the growth of the tumor in the mammary carcinoma model as compared to a control antibody.

Figure 18B:
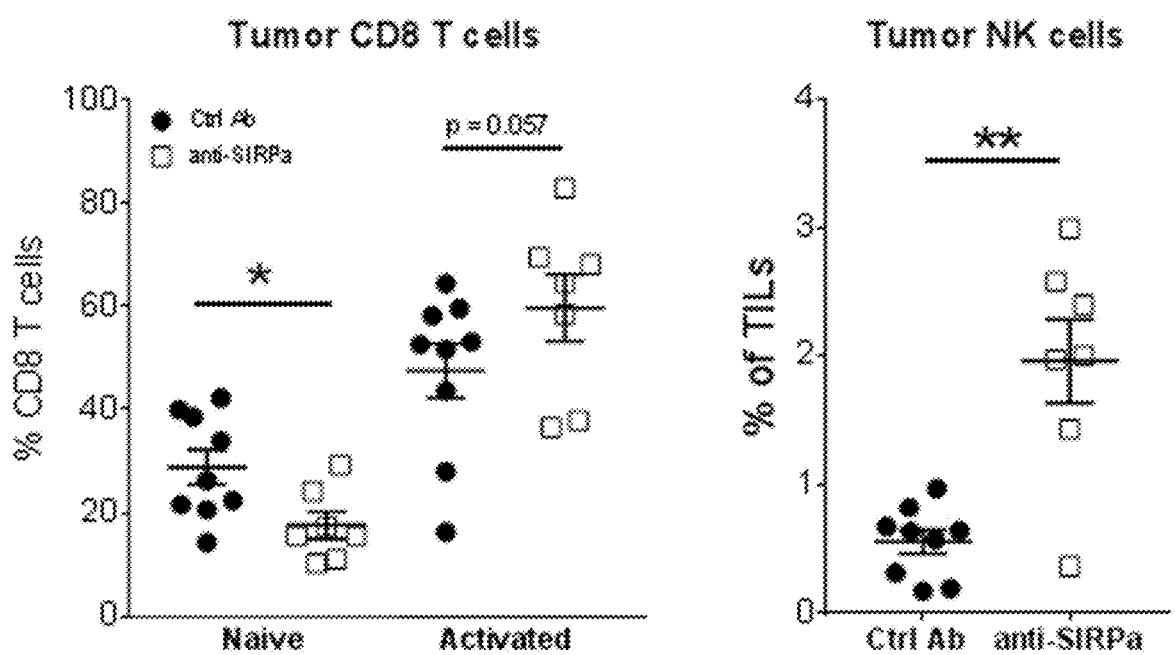
Figure 18C:
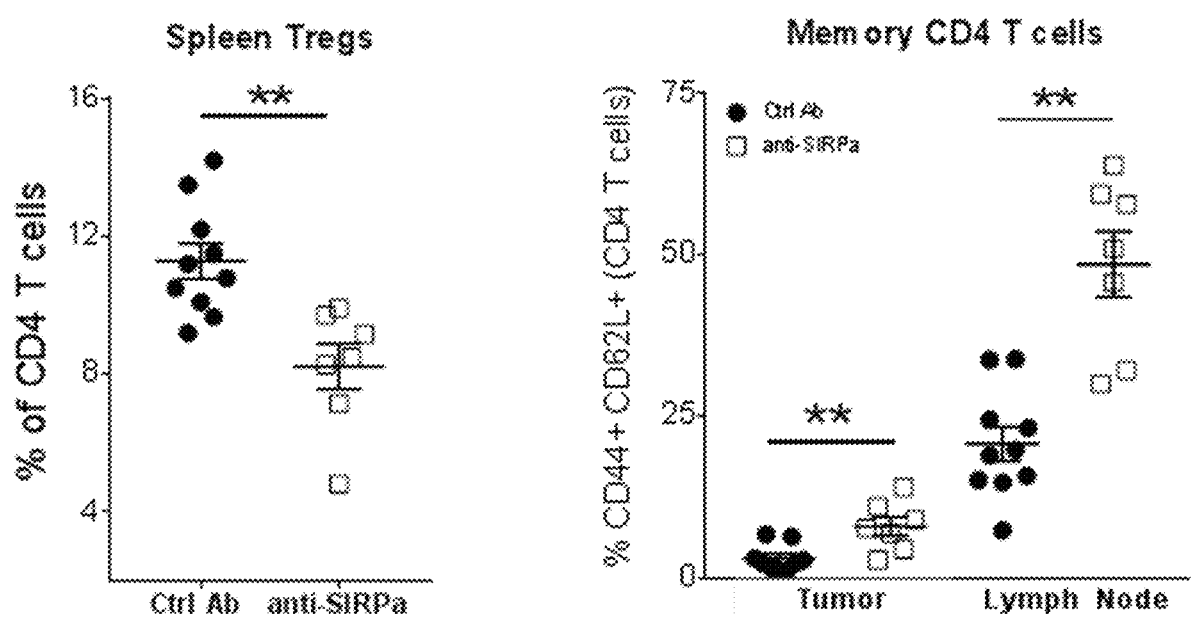

FIG. 18 shows the immune cell analysis two weeks after inoculation. Anti-SIRPa has a positive effect on myeloid and non-myeloid cells (T and NK cells) both in tumor and in periphery (spleen) with a dramatic decrease of Tregs and accumulation of memory T cells.

Example 21

Effects of SIRPa Antibodies on the Concentration of Hemoglobin and on the Hematocrit Method: Anti-SIRPa (P84 clone), anti-CD47 (MIAP410 clone) and irrelevant isotype control were administered intraperitoneally at day 0 and day 2 at 12 mg/kg in C57Bl/6 mice. Blood samples were collected at day 0 and day 3 in EDTA containing tubes and blood count was performed with a XS-800i haematology analyzer (Sysmex). The level of hemoglobin (left) and the percentage of hematocrit (right) were evaluated at day 3.

Figure 19B:
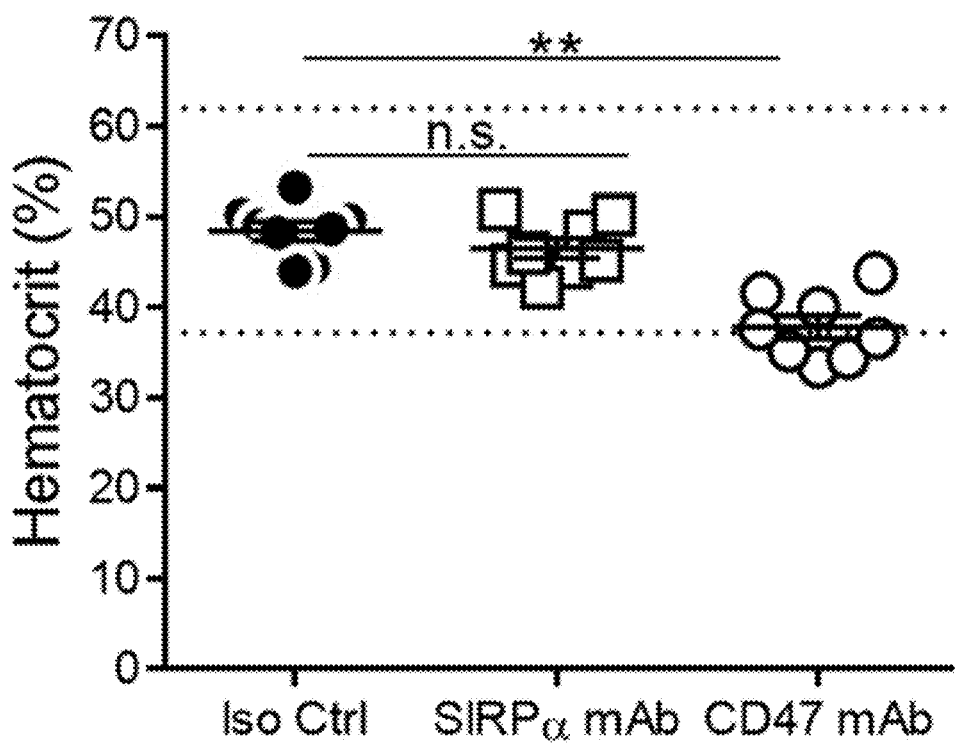

Results: As shown in FIG. 19, the anti-SIRPa antibody has no toxic effect on the concentration of hemoglobin and on the hematocrit. At the opposite, the anti-CD47 antibody induces a decrease of the concentration of hemoglobin and of the hematocrit in accordance with anemia observed during phase 1 in man.

Example 22

Platelet Aggregation

Method: Blood was collected from healthy donor volunteers into Vacuette collection tubes (Greiner Bio-One) buffered with sodium citrate. Platelet rich plasma (PRP) and platelet poor plasma (PPP) were obtained by centrifugation for 10 minutes at 200 g and 15 minutes at 3 500 g, respectively. The working PRP was adjusted to $3.10^8$ platelets.$L^{-1}$. Inhibition Assays: mAb were pre-incubated with PRP for a final concentration of 40 or 50 µg.$mL^{-1}$ test antibodies. After 3 minutes without stirring, platelet aggregation was initiated with ADP 5 µM addition. Aggregation was determined by measuring the transmission of light through the sample at 37° C. with continuous stirring using a standard optical aggregometer (TA-8V Thrombo-Aggregometer, SD Innovation SAS, Frouard, France). The transmission of PPP was set as 100%. Aggregation was recorded under stirring for a total of 5 minutes. Induction Assays: Platelet aggregation was directly initiated by mAb addition (50 µg.$mL^{-1}$). Aggregation was recorded under stirring for a total of max. 10 minutes.

Figure 20A:
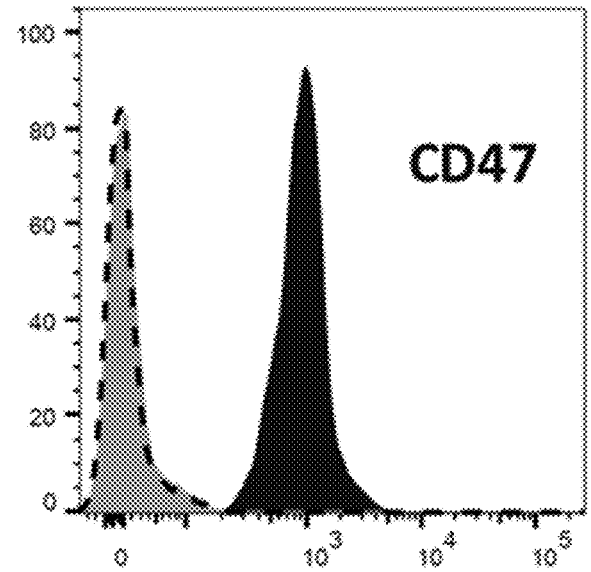
Figure 20B:
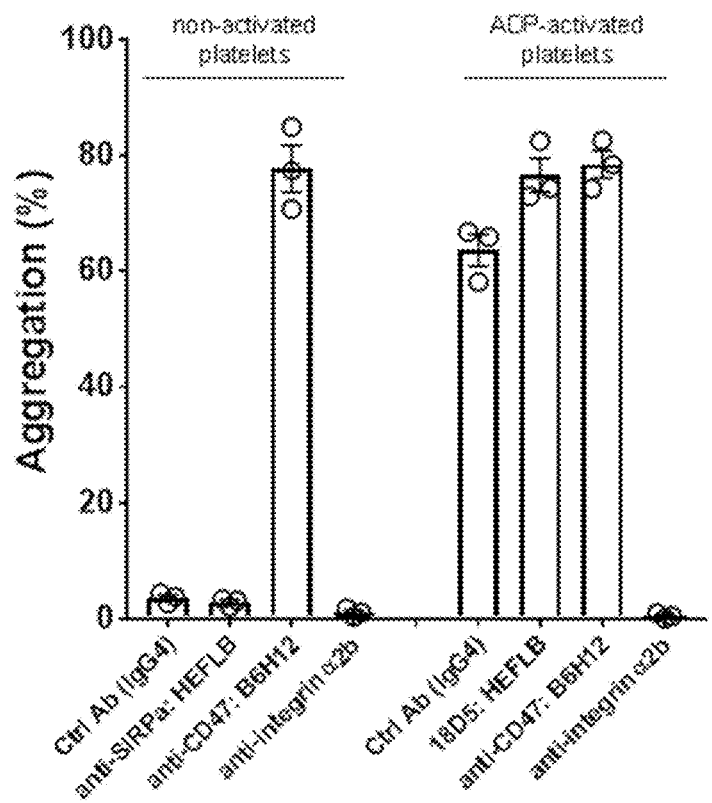

Results: As shown in FIG. 20, in contrast to anti-CD47 antibodies, anti-SIRPa antibodies does not bind to human red blood cells or platelets. Consequently, anti-CD47 induces in vitro human platelets aggregation while anti-SIRPa antibodies does not. Similarly, anti-SIRPa antibodies does not disturb reversible ADP-induced human platelets aggregation while anti-integrin alpha 2b completely abrogates it.

Example 23

Proliferation of Allogeneic T Cells by SIRPa-Blocking CD14+ Cells from a Cancer Ovarian Ascitis Method: Allogeneic CD4 T cells were isolated by positive selection using an AutoMACS (Miltenyi) from hPBMC of a buffy coat of a healthy volunteer. CD4 were plated in 96-round well plate (50 000 cells/well). CD14+ cells were isolated by the same method from the ascitis of a cancer ovarian patient. The CD14+ cells were plated with the allogeneic CD4 T cells at a 1:1 ratio for 5 days. In some conditions, human LPS-matured allogeneic monocyte-derived dendritic cells (moDC) were added at a 1:5 ratio to stimulate T cells and analyzed the immunosuppressive action of different ratio of CD14+ MDSC purified from the ascite. Antibodies targeting the SIRPa/CD47 pathway were added from the beginning of the proliferation test at a saturating concentration (10 µg/mL). Proliferation was measured by incorporation of $H^3$-thymidine during the last 12 h of culture.

Results: As shown in FIGS. 21A and 21B, Fresh and frozen human myeloid cells (TAM) purified from ovarian cancer ascites are hypo-stimulating allogeneic human T lymphocytes. In contrast to anti-CD47 antibodies, anti-SIRPa antibodies modifies myeloid cells properties allowing human T-cell activation and proliferation.

Figure 21C:
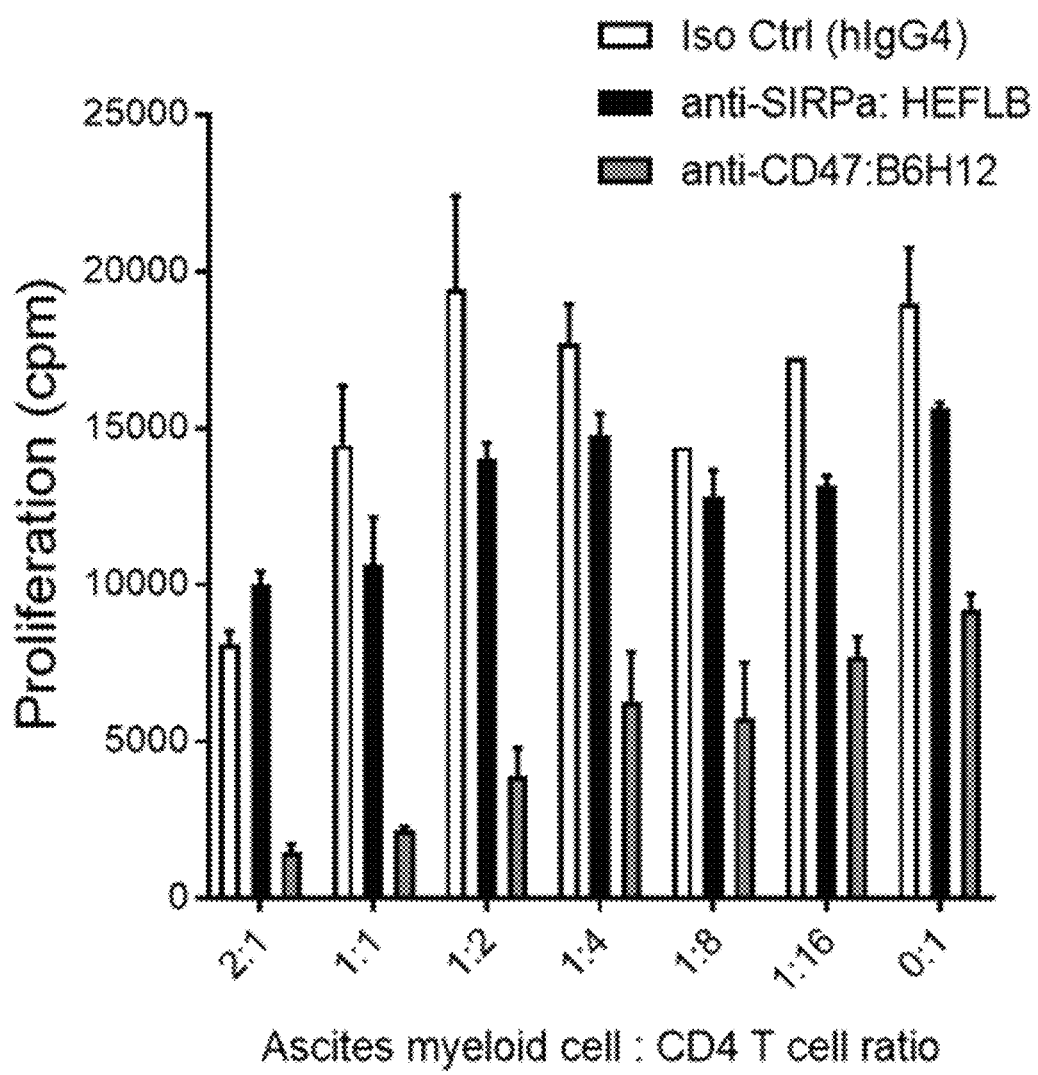

As shown in FIG. 21C, human myeloid cells (MDSC) purified from ovarian cancer ascites can suppress human T-cell proliferation induced by allogeneic moDC at 1:1 and 2:1 myeloid to T-cell ratio. In contrast to anti-CD47 antibodies, anti-SIRPa antibodies does not potentiates the immunosuppression induced by human MDSC.

The invention claimed is:

1. An isolated nucleic acid molecule encoding an antibody or antigen-binding fragment thereof or antigen-binding antibody mimetic, which comprises:
   a heavy chain variable domain comprising HCDR1, HCDR2 and HCDR3, and
   a light chain variable domain comprising LCDR1, LCDR2 and LCDR3,
   wherein:
   HCDR1 comprises the amino acid sequence set forth in SEQ ID NO: 14,
   HCDR2 comprises the amino acid sequence set forth in SEQ ID NO: 15 or SEQ ID NO: 16, and
   HCDR3 comprises the amino acid sequence set forth in SEQ ID NO: 17 SEQ ID NO: 18, SEQ ID NO: 19, or SEQ ID NO: 20, and wherein:
   LCDR1 comprises the amino acid sequence set forth in SEQ ID NO: 21,
   LCDR2 comprises the amino acid sequence set forth in SEQ ID NO: 22, and
   LCDR3 comprises the amino acid sequence set forth in SEQ ID NO: 23.

2. A vector comprising a nucleic acid molecule according to claim 1.

3. An isolated host cell comprising a vector according to claim 2.

4. The isolated nucleic acid molecule encoding an antibody or antigen-binding fragment thereof or antigen-binding antibody mimetic according to claim 1, comprising:
   a heavy chain variable domain comprising the amino acid sequence selected from the group consisting of SEQ ID NO: 24, SEQ ID NO: 25, SEQ ID NO: 26, SEQ ID NO: 27, SEQ ID NO: 28, SEQ ID NO: 29 and SEQ ID NO: 30, and
   a light chain variable domain comprising the amino acid sequence selected from the group consisting of SEQ ID NO: 31, SEQ ID NO: 32 and SEQ ID NO: 33.

5. The isolated nucleic acid molecule encoding an antibody or antigen-binding fragment thereof or antigen-binding antibody mimetic according to claim 1, comprising:
   a light chain variable domain comprising the amino acid sequence set forth in SEQ ID NO: 33, and
   a heavy chain variable domain comprising the amino acid sequence selected from the group consisting of SEQ ID NO: 24, SEQ ID NO: 25, SEQ ID NO: 26, SEQ ID NO: 27, SEQ ID NO: 28, SEQ ID NO: 29 and SEQ ID NO: 30.

6. The isolated nucleic acid molecule encoding an antibody or antigen-binding fragment thereof or antigen-binding antibody mimetic according to claim 1, comprising:
   a light chain variable domain comprising the amino acid sequence set forth in SEQ ID NO: 33, and
   a heavy chain variable domain comprising the amino acid sequence selected from the group consisting of SEQ ID NO: 29 and SEQ ID NO: 30.

7. The isolated nucleic acid molecule encoding an antibody or antigen-binding fragment thereof or antigen-binding antibody mimetic according to claim 1, comprising:
   a light chain variable domain comprising the amino acid sequence set forth in SEQ ID NO: 33, and
   a heavy chain variable domain comprising the amino acid sequence set forth in SEQ ID NO: 30.

8. The isolated nucleic acid molecule encoding an antibody or antigen-binding fragment thereof or antigen-binding antibody mimetic according to claim 1, comprising:
   (i) a heavy chain variable domain comprising the amino acid sequence set forth in SEQ ID NO: 24, and a light chain variable domain comprising the amino acid sequence set forth in SEQ ID NO: 31, or (ii) a heavy chain variable domain comprising the amino acid sequence set forth in SEQ ID NO: 25, and a light chain variable domain comprising the amino acid sequence set forth in SEQ ID NO: 32, or (iii) a heavy chain variable domain comprising the amino acid sequence set forth in SEQ ID NO: 25, and a light chain variable domain comprising the amino acid sequence set forth in SEQ ID NO: 33, or (iv) a heavy chain variable domain comprising the amino acid sequence set forth in SEQ ID NO: 26, and a light chain variable domain comprising the amino acid sequence set forth in SEQ ID NO: 32, or (v) a heavy chain variable domain comprising the amino acid sequence set forth in SEQ ID NO: 26, and a light chain variable domain comprising the amino acid sequence set forth in SEQ ID NO: 33, or (vi) a heavy chain variable domain comprising the amino acid sequence set forth in SEQ ID NO: 27, and a light chain variable domain comprising the amino acid sequence set forth in SEQ ID NO: 32, or (vii) a heavy chain variable domain comprising the amino acid sequence set forth in SEQ ID NO: 27, and a light chain variable domain comprising the amino acid sequence set forth in SEQ ID NO: 33, or (viii) a heavy chain variable domain comprising the amino acid sequence set forth in SEQ ID NO: 28, and a light chain variable domain comprising the amino acid sequence set forth in SEQ ID NO: 32, or (ix) a heavy chain variable domain comprising the amino acid sequence set forth in SEQ ID NO: 28, and a light chain variable domain comprising the amino acid sequence set forth in SEQ ID NO:

33, or (x) a heavy chain variable domain comprising the amino acid sequence set forth in SEQ ID NO: 29, and a light chain variable domain comprising the amino acid sequence set forth in SEQ ID NO: 32, or (xi) a heavy chain variable domain comprising the amino acid sequence set forth in SEQ ID NO: 29, and a light chain variable domain comprising the amino acid sequence set forth in SEQ ID NO: 33, or (xii) a heavy chain variable domain comprising the amino acid sequence set forth in SEQ ID NO: 30, and a light chain variable domain comprising the amino acid sequence set forth in SEQ ID NO: 32, or (xiii) a heavy chain variable domain comprising the amino acid sequence set forth in SEQ ID NO: 30, and a light chain variable domain comprising the amino acid sequence set forth in SEQ ID NO: 33.

9. The isolated nucleic acid molecule encoding an antibody or antigen-binding fragment thereof or antigen-binding antibody mimetic according to claim 1, wherein said antibody or fragment is a humanized monoclonal antibody or antigen-binding fragment thereof.

10. The isolated nucleic acid molecule encoding an antibody or antigen-binding fragment thereof or antigen-binding antibody mimetic according to claim 9, wherein the antibody light chain constant domain is derived from human kappa light chain constant domain or comprises the sequence of SEQ ID NO: 35.

11. The isolated nucleic acid molecule encoding an antibody or antigen-binding fragment thereof or antigen-binding antibody mimetic according to claim 9, wherein the antibody heavy chain constant domain is derived from a human IgG1, IgG2, IgG3, or IgG4 heavy chain constant domain or comprises the sequence of SEQ ID NO: 34.

12. The isolated nucleic acid molecule encoding an antibody or antigen-binding fragment thereof or antigen-binding antibody mimetic according to claim 1, wherein said antibody or fragment or mimetic does not specifically bind to human SIRPg.

13. The isolated nucleic acid molecule encoding an antibody or antigen-binding fragment thereof or antigen-binding antibody mimetic according to claim 1, wherein said antibody or fragment or mimetic does not inhibit the binding of human CD47 to human SIRPg.

14. The isolated nucleic acid molecule encoding an antibody or antigen-binding fragment thereof or antigen-binding antibody mimetic according to claim 1, wherein said antibody or fragment or mimetic does not specifically bind to human T-cells or to CD3+ T-cells.

15. The isolated nucleic acid molecule encoding an antibody or antigen-binding fragment thereof or antigen-binding antibody mimetic according to claim 1, wherein said antibody or fragment or mimetic does not inhibit the proliferation of human T-cells.

16. The isolated nucleic acid molecule encoding an antibody or antigen-binding fragment thereof or antigen-binding antibody mimetic according to claim 1, wherein the antibody or fragment or mimetic is an antagonist of SIRPa and inhibits the binding of human SIRPa to human CD47.

17. The isolated nucleic acid molecule encoding an antibody or antigen- binding fragment thereof or antigen-binding antibody mimetic according to claim 1, comprising:
a light chain variable domain consisting of the amino acid sequence set forth in SEQ ID NO: 33, and a heavy chain variable domain consisting of the amino acid sequence set forth in SEQ ID NO: 30.

18. The isolated nucleic acid molecule encoding an antibody or antigen-binding fragment thereof or antigen-binding antibody mimetic according to claim 1, comprising:
a light chain variable domain comprising the amino acid sequence set forth in SEQ ID NO: 32 and
a heavy chain variable domain comprising the amino acid sequence set forth in SEQ ID NO: 30.

19. The isolated nucleic acid molecule encoding an antibody or antigen-binding fragment thereof or antigen-binding antibody mimetic according to claim 1, comprising:
a heavy chain comprising the amino acid sequence set forth in SEQ ID NO: 42, and
a light chain comprising the amino acid sequence set forth in SEQ ID NO: 45.

20. The isolated nucleic acid molecule encoding an antibody or antigen-binding fragment thereof or antigen-binding antibody mimetic according to claim 1, comprising:
a heavy chain comprising the amino acid sequence set forth in SEQ ID NO: 42, and
a light chain comprising the amino acid sequence set forth in SEQ ID NO: 44.

21. The isolated nucleic acid molecule encoding an antibody or antigen-binding fragment thereof or antigen-binding antibody mimetic according to claim 1, wherein the antibody is a full-length antibody.

22. The isolated nucleic acid molecule encoding an antibody or antigen-binding fragment thereof or antigen-binding antibody mimetic according to claim 1, wherein the antibody or antigen-binding fragment thereof or mimetic is monoclonal.

23. The isolated nucleic acid molecule encoding an antibody or antigen-binding fragment thereof or antigen-binding antibody mimetic according to claim 1, wherein the antibody or antigen-binding fragment thereof or mimetic is recombinant.

* * * * *

SEQUENCE LISTING

```
<160> NUMBER OF SEQ ID NOS: 73

<210> SEQ ID NO 1
<211> LENGTH: 7
<212> TYPE: PRT
<213> ORGANISM: Homo sapiens

<400> SEQUENCE: 1

Ser Leu Ile Pro Val Gly Pro
1               5

<210> SEQ ID NO 2
<211> LENGTH: 12
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = G or A

<400> SEQUENCE: 2

Xaa Arg Glu Leu Ile Tyr Asn Gln Lys Glu Gly His
1               5                   10

<210> SEQ ID NO 3
<211> LENGTH: 10
<212> TYPE: PRT
<213> ORGANISM: Homo sapiens
<220> FEATURE:
<221> NAME/KEY: MISC_FEATURE
<223> OTHER INFORMATION: Xaa = DV or T
<220> FEATURE:
```

```
<221> NAME/KEY: misc_feature
<222> LOCATION: (9)..(9)
<223> OTHER INFORMATION: Xaa can be any naturally occurring amino acid

<400> SEQUENCE: 3

Lys Phe Arg Lys Gly Ser Pro Asp Xaa Glu
1               5                   10

<210> SEQ ID NO 4
<211> LENGTH: 23
<212> TYPE: PRT
<213> ORGANISM: Homo sapiens

<400> SEQUENCE: 4

Gln His Thr Val Ser Phe Thr Cys Glu Ser His Gly Phe Ser Pro Arg
1               5                   10                  15

Asp Ile Thr Leu Lys Trp Phe
            20

<210> SEQ ID NO 5
<211> LENGTH: 11
<212> TYPE: PRT
<213> ORGANISM: Homo sapiens

<400> SEQUENCE: 5

Ile Cys Glu Val Ala His Val Thr Leu Gln Gly
1               5                   10

<210> SEQ ID NO 6
<211> LENGTH: 11
<212> TYPE: PRT
<213> ORGANISM: Homo sapiens

<400> SEQUENCE: 6

Tyr Pro Gln Arg Leu Gln Leu Thr Trp Leu Glu
1               5                   10

<210> SEQ ID NO 7
<211> LENGTH: 12
<212> TYPE: PRT
<213> ORGANISM: Homo sapiens

<400> SEQUENCE: 7

Gly Arg Glu Leu Ile Tyr Asn Gln Lys Glu Gly His
1               5                   10

<210> SEQ ID NO 8
<211> LENGTH: 11
<212> TYPE: PRT
<213> ORGANISM: Homo sapiens

<400> SEQUENCE: 8

Lys Phe Arg Lys Gly Ser Pro Asp Asp Val Glu
1               5                   10

<210> SEQ ID NO 9
<211> LENGTH: 12
<212> TYPE: PRT
<213> ORGANISM: Homo sapiens

<400> SEQUENCE: 9

Ala Arg Glu Leu Ile Tyr Asn Gln Lys Glu Gly His
1               5                   10
```

```
<210> SEQ ID NO 10
<211> LENGTH: 10
<212> TYPE: PRT
<213> ORGANISM: Homo sapiens

<400> SEQUENCE: 10

Lys Phe Arg Lys Gly Ser Pro Asp Thr Glu
1               5                   10

<210> SEQ ID NO 11
<211> LENGTH: 7
<212> TYPE: PRT
<213> ORGANISM: Homo sapiens

<400> SEQUENCE: 11

Gly Arg Glu Leu Ile Tyr Asn
1               5

<210> SEQ ID NO 12
<211> LENGTH: 22
<212> TYPE: PRT
<213> ORGANISM: Homo sapiens

<400> SEQUENCE: 12

His Thr Val Ser Phe Thr Cys Glu Ser His Gly Phe Ser Pro Arg Asp
1               5                   10                  15

Ile Thr Leu Lys Trp Phe
            20

<210> SEQ ID NO 13
<211> LENGTH: 7
<212> TYPE: PRT
<213> ORGANISM: Homo sapiens

<400> SEQUENCE: 13

Ala Arg Glu Leu Ile Tyr Asn
1               5

<210> SEQ ID NO 14
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 14

Ser Tyr Trp Val His
1               5

<210> SEQ ID NO 15
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 15

Asn Ile Asp Pro Ser Asp Ser Asp Thr His Tyr Asn Gln Lys Phe Lys
1               5                   10                  15

Asp

<210> SEQ ID NO 16
<211> LENGTH: 17
<212> TYPE: PRT
<213> ORGANISM: Artificial Sequence
```

```
<220> FEATURE:
<223> OTHER INFORMATION: Heavy chain CDR2

<400> SEQUENCE: 16

Asn Ile Asp Pro Ser Asp Ser Asp Thr His Tyr Ser Pro Ser Phe Gln
1               5                   10                  15
Gly

<210> SEQ ID NO 17
<211> LENGTH: 11
<212> TYPE: PRT
<213> ORGANISM: Artificial Sequence
<220> FEATURE:
<223> OTHER INFORMATION: Heavy chain CDR3

<400> SEQUENCE: 17

Gly Gly Thr Gly Thr Met Ala Trp Phe Ala Tyr
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Heavy chain CDR3

<400> SEQUENCE: 18

Gly Gly Thr Gly Thr Leu Ala Trp Phe Ala Tyr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Heavy chain CDR3

<400> SEQUENCE: 19

Gly Gly Thr Gly Thr Met Ala Tyr Phe Ala Tyr
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Heavy chain CDR3

<400> SEQUENCE: 20

Gly Gly Thr Gly Thr Leu Ala Tyr Phe Ala Tyr
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Light chain CDR1

<400> SEQUENCE: 21

Arg Ser Ser Gln Ser Leu Val His Ser Tyr Gly Asn Thr Tyr Leu Tyr
1               5                   10                  15

<210> SEQ ID NO 22
<211> LENGTH: 7
<212> TYPE: PRT
```

```
<213> ORGANISM: Artificial Sequence
<220> FEATURE:
<223> OTHER INFORMATION: Light chain CDR2

<400> SEQUENCE: 22

Arg Val Ser Asn Arg Phe Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Light chain CDR3

<400> SEQUENCE: 23

Phe Gln Gly Thr His Val Pro Tyr Thr
1               5

<210> SEQ ID NO 24
<211> LENGTH: 120
<212> TYPE: PRT
<213> ORGANISM: Artificial Sequence
<220> FEATURE:
<223> OTHER INFORMATION: Heavy chain variable domain

<400> SEQUENCE: 24

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Val His Trp Val Lys Gln Arg Pro Ile Gln Gly Leu Glu Trp Ile
        35                  40                  45

Gly Asn Ile Asp Pro Ser Asp Ser Asp Thr His Tyr Asn Gln Lys Phe
    50                  55                  60

Lys Asp Lys Ala Ser Leu Thr Val Asp Lys Ser Ser Thr Ala Tyr
65                  70                  75                  80

Met Gln Leu Ser Ser Leu Thr Phe Glu Asp Ser Ala Val Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ala
        115                 120

<210> SEQ ID NO 25
<211> LENGTH: 120
<212> TYPE: PRT
<213> ORGANISM: Artificial Sequence
<220> FEATURE:
<223> OTHER INFORMATION: Heavy chain variable domain

<400> SEQUENCE: 25

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Thr Phe Thr Ser Tyr
            20                  25                  30

Trp Val His Trp Val Arg Gln Met Pro Gly Lys Gly Leu Glu Trp Ile
        35                  40                  45

Gly Asn Ile Asp Pro Ser Asp Ser Asp Thr His Tyr Asn Gln Lys Phe
    50                  55                  60

Lys Asp His Val Thr Leu Ser Val Asp Lys Ser Ile Ser Thr Ala Tyr
```

65                  70                  75                  80
Leu Gln Leu Ser Ser Leu Lys Ala Ser Asp Thr Ala Met Tyr Tyr Cys
                    85                  90                  95

Val Arg Gly Gly Thr Gly Thr Met Ala Trp Phe Ala Tyr Trp Gly Gln
                100                 105                 110

Gly Thr Leu Val Thr Val Ser Ser
                115                 120

<210> SEQ ID NO 26
<211> LENGTH: 120
<212> TYPE: PRT
<213> ORGANISM: Artificial Sequence
<220> FEATURE:
<223> OTHER INFORMATION: Heavy chain variable domain

<400> SEQUENCE: 26

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
                20                  25                  30

Trp Val His Trp Val Arg Gln Met Pro Gly Lys Gly Leu Glu Trp Met
            35                  40                  45

Gly Asn Ile Asp Pro Ser Asp Ser Asp Thr His Tyr Asn Gln Lys Phe
    50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                    85                  90                  95

Val Arg Gly Gly Thr Gly Thr Met Ala Trp Phe Ala Tyr Trp Gly Gln
                100                 105                 110

Gly Thr Leu Val Thr Val Ser Ser
                115                 120

<210> SEQ ID NO 27
<211> LENGTH: 120
<212> TYPE: PRT
<213> ORGANISM: Artificial Sequence
<220> FEATURE:
<223> OTHER INFORMATION: Heavy chain variable domain

<400> SEQUENCE: 27

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
                20                  25                  30

Trp Val His Trp Val Arg Gln Met Pro Gly Lys Gly Leu Glu Trp Met
            35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                    85                  90                  95

Val Arg Gly Gly Thr Gly Thr Met Ala Trp Phe Ala Tyr Trp Gly Gln
                100                 105                 110

Gly Thr Leu Val Thr Val Ser Ser
                115                 120

<210> SEQ ID NO 28
<211> LENGTH: 120
<212> TYPE: PRT
<213> ORGANISM: Artificial Sequence
<220> FEATURE:
<223> OTHER INFORMATION: Heavy chain variable domain

<400> SEQUENCE: 28

```
Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Trp Phe Ala Tyr Trp Gly Gln
            100                 105                 110

Gly Thr Leu Val Thr Val Ser Ser
        115                 120
```

<210> SEQ ID NO 29
<211> LENGTH: 120
<212> TYPE: PRT
<213> ORGANISM: Artificial Sequence
<220> FEATURE:
<223> OTHER INFORMATION: Heavy chain variable domain

<400> SEQUENCE: 29

```
Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Tyr Phe Ala Tyr Trp Gly Gln
            100                 105                 110

Gly Thr Leu Val Thr Val Ser Ser
        115                 120
```

<210> SEQ ID NO 30
<211> LENGTH: 120
<212> TYPE: PRT
<213> ORGANISM: Artificial Sequence
<220> FEATURE:
<223> OTHER INFORMATION: Heavy chain variable domain

<400> SEQUENCE: 30

Glu Val Gln Leu Val Gln Ser Gly Ala Glu Val Lys Lys Pro Gly Glu

-continued

```
                1               5                  10                 15
        Ser Leu Arg Ile Ser Cys Lys Ala Ser Gly Tyr Ser Phe Thr Ser Tyr
                        20                  25                 30

Trp Val His Val Arg Gln Met Pro Gly Lys Gly Leu Glu Trp Met
                        35                  40                 45

Gly Asn Ile Asp Pro Ser Ser Asp Thr His Tyr Ser Pro Ser Phe
                    50                  55                 60

Gln Gly His Val Thr Leu Ser Val Asp Lys Ser Ile Ser Thr Ala Tyr
        65                  70                  75                 80

Leu Gln Leu Ser Ser Leu Lys Ala Ser Asp Thr Ala Met Tyr Tyr Cys
                            85                  90                 95

Val Arg Gly Gly Thr Gly Thr Leu Ala Tyr Phe Ala Tyr Trp Gly Gln
                            100                 105                110

Gly Thr Leu Val Thr Val Ser Ser
                    115                 120
```

<210> SEQ ID NO 31
<211> LENGTH: 112
<212> TYPE: PRT
<213> ORGANISM: Artificial Sequence
<220> FEATURE:
<223> OTHER INFORMATION: Light chain variable domain

<400> SEQUENCE: 31

```
        Asp Val Val Met Thr Gln Thr Pro Leu Ser Leu Pro Val Ser Leu Gly
        1               5                   10                 15

Asp Gln Ala Ser Ile Ser Cys Arg Ser Ser Gln Ser Leu Val His Ser
                        20                  25                 30

Tyr Gly Asn Thr Tyr Leu Tyr Trp Tyr Leu Gln Lys Pro Gly Gln Ser
                        35                  40                 45

Pro Lys Leu Leu Ile Tyr Arg Val Ser Asn Arg Phe Ser Gly Val Pro
                    50                  55                 60

Asp Arg Phe Ser Gly Ser Gly Ser Gly Thr Asp Phe Thr Leu Lys Ile
        65                  70                  75                 80

Ser Arg Val Glu Ala Glu Asp Leu Gly Val Tyr Phe Cys Phe Gln Gly
                            85                  90                 95

Thr His Val Pro Tyr Thr Phe Gly Ser Gly Thr Lys Leu Glu Ile Lys
                            100                 105                110
```

<210> SEQ ID NO 32
<211> LENGTH: 112
<212> TYPE: PRT
<213> ORGANISM: Artificial Sequence
<220> FEATURE:
<223> OTHER INFORMATION: Light chain variable domain

<400> SEQUENCE: 32

```
        Asp Val Val Met Thr Gln Ser Pro Leu Ser Leu Pro Val Thr Leu Gly
        1               5                   10                 15

Gln Pro Ala Ser Ile Ser Cys Arg Ser Ser Gln Ser Leu Val His Ser
                        20                  25                 30

Tyr Gly Asn Thr Tyr Leu Tyr Trp Tyr Gln Gln Arg Pro Gly Gln Ser
                        35                  40                 45

Pro Arg Leu Leu Ile Tyr Arg Val Ser Asn Arg Phe Ser Gly Val Pro
                    50                  55                 60

Asp Arg Phe Ser Gly Ser Gly Ser Gly Thr Asp Phe Thr Leu Lys Ile
        65                  70                  75                 80
```

```
Ser Arg Val Glu Ala Glu Asp Val Gly Val Tyr Phe Cys Phe Gln Gly
                85                  90                  95

Thr His Val Pro Tyr Thr Phe Gly Gly Gly Thr Lys Val Glu Ile Lys
            100                 105                 110
```

<210> SEQ ID NO 33
<211> LENGTH: 112
<212> TYPE: PRT
<213> ORGANISM: Artificial Sequence
<220> FEATURE:
<223> OTHER INFORMATION: Light chain variable domain

<400> SEQUENCE: 33

```
Asp Val Val Met Thr Gln Ser Pro Leu Ser Leu Pro Val Thr Leu Gly
1               5                   10                  15

Gln Pro Ala Ser Ile Ser Cys Arg Ser Gln Ser Leu Val His Ser
            20                  25                  30

Tyr Gly Asn Thr Tyr Leu Tyr Trp Phe Gln Gln Arg Pro Gly Gln Ser
            35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr His Val Pro Tyr Thr Phe Gly Gly Gly Thr Lys Val Glu Ile Lys
            100                 105                 110
```

<210> SEQ ID NO 34
<211> LENGTH: 327
<212> TYPE: PRT
<213> ORGANISM: Artificial Sequence
<220> FEATURE:
<223> OTHER INFORMATION: Heavy chain constant domain-IgG4m-S228P

<400> SEQUENCE: 34

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Pro Gly Lys
            325

<210> SEQ ID NO 35
<211> LENGTH: 107
<212> TYPE: PRT
<213> ORGANISM: Artificial Sequence
<220> FEATURE:
<223> OTHER INFORMATION: Light chain constant domain-CLkappa

<400> SEQUENCE: 35

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 36
<211> LENGTH: 447
<212> TYPE: PRT
<213> ORGANISM: Artificial Sequence
<220> FEATURE:
<223> OTHER INFORMATION: Heavy chain sequence 18D5

<400> SEQUENCE: 36

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Val His Trp Val Lys Gln Arg Pro Ile Gln Gly Leu Glu Trp Ile
```

35                  40                  45
Gly Asn Ile Asp Pro Ser Asp Ser Asp Thr His Tyr Asn Gln Lys Phe
 50                  55                  60

Lys Asp Lys Ala Ser Leu Thr Val Asp Lys Ser Ser Thr Ala Tyr
 65                  70                  75                  80

Met Gln Leu Ser Ser Leu Thr Phe Glu Asp Ser Ala Val Tyr Tyr Cys
                 85                  90                  95

Val Arg Gly Gly Thr Gly Thr Met Ala Trp Phe Ala Tyr Trp Gly Gln
                100                 105                 110

Gly Thr Leu Val Thr Val Ser Ala Ala Ser Thr Lys Gly Pro Ser Val
                115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 37

<211> LENGTH: 447
<212> TYPE: PRT
<213> ORGANISM: Artificial Sequence
<220> FEATURE:
<223> OTHER INFORMATION: Heavy chain sequence HA

<400> SEQUENCE: 37

```
Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Thr Phe Thr Ser Tyr
            20                  25                  30

Trp Val His Trp Val Arg Gln Met Pro Gly Lys Gly Leu Glu Trp Ile
        35                  40                  45

Gly Asn Ile Asp Pro Ser Asp Ser Asp Thr His Tyr Asn Gln Lys Phe
    50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

```
Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 38
<211> LENGTH: 447
<212> TYPE: PRT
<213> ORGANISM: Artificial Sequence
<220> FEATURE:
<223> OTHER INFORMATION: Heavy chain sequence HB

<400> SEQUENCE: 38

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
                20                  25                  30

Trp Val His Trp Val Arg Gln Met Pro Gly Lys Gly Leu Glu Trp Met
            35                  40                  45

Gly Asn Ile Asp Pro Ser Asp Ser Asp Thr His Tyr Asn Gln Lys Phe
        50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300
```

```
Val Leu Thr Val Leu His Gln Asp Trp Leu Asn Gly Lys Glu Tyr Lys
305                 310                 315                 320

Cys Lys Val Ser Asn Lys Gly Leu Pro Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 39
<211> LENGTH: 447
<212> TYPE: PRT
<213> ORGANISM: Artificial Sequence
<220> FEATURE:
<223> OTHER INFORMATION: Heavy chain sequence HC

<400> SEQUENCE: 39

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220
```

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys
                435                 440                 445

<210> SEQ ID NO 40
<211> LENGTH: 447
<212> TYPE: PRT
<213> ORGANISM: Artificial Sequence
<220> FEATURE:
<223> OTHER INFORMATION: Heavy chain sequence HE

<400> SEQUENCE: 40

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Heavy chain sequence HF

<400> SEQUENCE: 41

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
                20                  25                  30

Trp Val His Trp Val Arg Gln Met Pro Gly Lys Gly Leu Glu Trp Met
            35                  40                  45

Gly Asn Ile Asp Pro Ser Asp Ser Asp Thr His Tyr Ser Pro Ser Phe
    50                  55                  60

```
Gln Gly His Val Thr Leu Ser Val Asp Lys Ser Ile Ser Thr Ala Tyr
 65                  70                  75                  80

Leu Gln Leu Ser Ser Leu Lys Ala Ser Asp Thr Ala Met Tyr Tyr Cys
                 85                  90                  95

Val Arg Gly Gly Thr Gly Thr Met Ala Tyr Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 42
<211> LENGTH: 447
<212> TYPE: PRT
<213> ORGANISM: Artificial Sequence
<220> FEATURE:
```

<223> OTHER INFORMATION: Heavy chain sequence HEF

<400> SEQUENCE: 42

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Tyr Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

-continued

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 43
<211> LENGTH: 219
<212> TYPE: PRT
<213> ORGANISM: Artificial Sequence
<220> FEATURE:
<223> OTHER INFORMATION: Light chain sequence 18D5

<400> SEQUENCE: 43

Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val His Ser
            20                  25                  30

Tyr Gly Asn Thr Tyr Leu Tyr Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 44
<211> LENGTH: 219
<212> TYPE: PRT
<213> ORGANISM: Artificial Sequence
<220> FEATURE:
<223> OTHER INFORMATION: Light chain sequence LA

<400> SEQUENCE: 44

Asp Val Val Met Thr Gln Ser Pro Leu Ser Leu Pro Val Thr Leu Gly
1               5                   10                  15

Gln Pro Ala Ser Ile Ser Cys Arg Ser Gln Ser Leu Val His Ser
            20                  25                  30

Tyr Gly Asn Thr Tyr Leu Tyr Trp Tyr Gln Gln Arg Pro Gly Gln Ser
        35                  40                  45

```
Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Thr His Val Pro Tyr Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215
```

<210> SEQ ID NO 45
<211> LENGTH: 219
<212> TYPE: PRT
<213> ORGANISM: Artificial Sequence
<220> FEATURE:
<223> OTHER INFORMATION: Light chain sequence LB

<400> SEQUENCE: 45

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Tyr Gly Asn Thr Tyr Leu Tyr Trp Phe Gln Gln Arg Pro Gly Gln Ser
        35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr His Val Pro Tyr Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

Lys His Lys Val Tyr Ala Cys Glu Val Thr His Gln Gly Leu Ser Ser
         195                 200                 205

Pro Val Thr Lys Ser Phe Asn Arg Gly Glu Cys
     210                 215

<210> SEQ ID NO 46
<211> LENGTH: 360
<212> TYPE: DNA
<213> ORGANISM: Artificial Sequence
<220> FEATURE:
<223> OTHER INFORMATION: Nucleic acid sequence coding the heavy chain
      variable domain 18D5

<400> SEQUENCE: 46
caggtgcagc tgcagcagcc aggagctgag ctggtgaggc ctggctccag cgtgaagctg      60
tcctgcaagg ctagcggcta caccttcaca agctattggg tgcactgggt gaagcagcgg     120
ccaatccagg gcctggagtg gatcggcaac atcgacccca gcgactctga tacccattac     180
aatcagaagt ttaaggacaa ggcctctctg accgtgcata agtcttccag cacagcttat     240
atgcagctgt cttccctgac attcgaggat ccgccgtgt actattgcgt gaggggagga     300
accggaacaa tggcttggtt tgcttactgg ggccagggca ccctggtgac agtgtctgct     360

<210> SEQ ID NO 47
<211> LENGTH: 360
<212> TYPE: DNA
<213> ORGANISM: Artificial Sequence
<220> FEATURE:
<223> OTHER INFORMATION: Nucleic acid sequence coding the heavy chain
      variable domain HA

<400> SEQUENCE: 47
gaggtgcagc tggtgcagag cggagctgag gtgaagaagc caggcgagtc tctgaggatc      60
tcctgcaagg ctagcggcta caccttcaca tcttattggg tgcactgggt gcggcagatg     120
ccaggcaagg gcctggagtg gatcggcaac atcgacccta gcgactctga tacccactac     180
aatcagaagt ttaaggacca tgtgaccctg tctgtggata gtccatcag cacagcctat     240 ctgcagctgt ccagcctgaa ggcctccgat acagctatgt actattgcgt gaggggagga     300
accggaacaa tggcttggtt cgcttactgg ggccagggca ccctggtgac agtgtcttcc     360

<210> SEQ ID NO 48
<211> LENGTH: 360
<212> TYPE: DNA
<213> ORGANISM: Artificial Sequence
<220> FEATURE:
<223> OTHER INFORMATION: Nucleic acid sequence coding the heavy chain
      variable domain HB

<400> SEQUENCE: 48
gaggtgcagc tggtgcagtc cggagctgag gtgaagaagc caggcgagtc tctgaggatc      60
tcctgcaagg cttctggcta ctccttcacc agctattggg tgcactgggt gcggcagatg     120
ccaggcaagg gcctggagtg gatgggcaac atcgacccta gcgactctga tacacactac     180
aatcagaagt ttaaggacca tgtgaccctg agcgtggata gtccatcag cacagcctat     240 ctgcagctgt ccagcctgaa ggcctctgat accgctatgt actattgcgt gaggggagga     300
accggaacaa tggcttggtt cgcttactgg ggccagggca ccctggtgac agtgtcttcc     360

<210> SEQ ID NO 49
<211> LENGTH: 360

```
<212> TYPE: DNA
<213> ORGANISM: Artificial Sequence
<220> FEATURE:
<223> OTHER INFORMATION: Nucleic acid sequence coding the heavy chain
      variable domain HC

<400> SEQUENCE: 49
gaggtgcagc tggtgcagtc tggcgccgag gtgaagaagc caggcgagag cctgaggatc      60
tcttgcaagg ctagcggcta ctctttcacc tcctattggg tgcactgggt gcggcagatg     120
ccaggcaagg gcctggagtg gatgggcaac atcgacccca gcgactctga tacacactac     180
tcccctagct ttcagggcca tgtgaccctg tccgtggaca agtctatctc cacagcctat     240
ctgcagctgt ccagcctgaa ggccagcgat accgctatgt actattgcgt gaggggagga     300
accggaacaa tggcttggtt cgcttactgg ggccagggca ccctggtgac agtgtcttcc     360

<210> SEQ ID NO 50
<211> LENGTH: 360
<212> TYPE: DNA
<213> ORGANISM: Artificial Sequence
<220> FEATURE:
<223> OTHER INFORMATION: Nucleic acid sequence coding the heavy chain
      variable domain HE

<400> SEQUENCE: 50
gaggtgcagc tggtgcagtc tggcgccgag gtgaagaagc caggcgagag cctgaggatc      60
tcttgcaagg ctagcggcta ctctttcacc tcctattggg tgcactgggt gcggcagatg     120
ccaggcaagg gcctggagtg gatgggcaac atcgacccca gcgactctga tacacactac     180
tcccctagct ttcagggcca tgtgaccctg tccgtggaca agtctatctc cacagcctat     240
ctgcagctgt ccagcctgaa ggccagcgat accgctatgt actattgcgt gaggggagga     300
accggcacac tggcttggtt cgcttactgg ggccagggca ccctggtgac agtgtcttcc     360

<210> SEQ ID NO 51
<211> LENGTH: 360
<212> TYPE: DNA
<213> ORGANISM: Artificial Sequence
<220> FEATURE:
<223> OTHER INFORMATION: Nucleic acid sequence coding the heavy chain
      variable domain HF

<400> SEQUENCE: 51
gaggtgcagc tggtgcagtc tggcgccgag gtgaagaagc caggcgagag cctgaggatc      60
tcttgcaagg ctagcggcta ctctttcacc tcctattggg tgcactgggt gcggcagatg     120
ccaggcaagg gcctggagtg gatgggcaac atcgacccca gcgactctga tacacactac     180
tcccctagct ttcagggcca tgtgaccctg tccgtggaca agtctatctc cacagcctat     240
ctgcagctgt ccagcctgaa ggccagcgat accgctatgt actattgcgt gaggggagga     300
accggaacaa tggcttactt cgcttattgg ggccagggca ccctggtgac agtgtcttcc     360

<210> SEQ ID NO 52
<211> LENGTH: 360
<212> TYPE: DNA
<213> ORGANISM: Artificial Sequence
<220> FEATURE:
<223> OTHER INFORMATION: Nucleic acid sequence coding the heavy chain
      variable domain HEF

<400> SEQUENCE: 52
gaggtgcagc tggtgcagtc tggcgccgag gtgaagaagc caggcgagag cctgaggatc      60
```

```
tcttgcaagg ctagcggcta ctctttcacc tcctattggg tgcactgggt gcggcagatg      120
ccaggcaagg gcctggagtg gatgggcaac atcgacccca gcgactctga tacacactac      180
tcccctagct ttcagggcca tgtgaccctg tccgtggaca gtctatctc cacagcctat       240 ctgcagctgt ccagcctgaa ggccagcgat accgctatgt actattgcgt gaggggagga      300
accggcacac tggcttactt cgcttattgg ggccagggca cctggtgac agtgtcttcc       360

<210> SEQ ID NO 53
<211> LENGTH: 336
<212> TYPE: DNA
<213> ORGANISM: Artificial Sequence
<220> FEATURE:
<223> OTHER INFORMATION: Nucleic acid sequence coding the light chain
      variable domain 18D5

<400> SEQUENCE: 53
gacgtggtca tgacccagac accactgagc ctgcccgtgt ccctgggcga tcaggcctct       60
atctcctgca ggtccagcca gtccctggtg cacagctatg caacacata cctgtattgg      120 tacctgcaga agccaggcca gtcccccaag ctgctgatct acagggtgtc taatcggttc      180
tccggcgtgc ctgacaggtt ctccggctct ggctccggca ccgatttcac actgaagatc      240
agcagggtgg aggctgagga cctgggcgtg tatttctgtt ttcagggcac ccatgtgcca      300
tacacatttg gctctggcac caagctggag atcaag                                336

<210> SEQ ID NO 54
<211> LENGTH: 336
<212> TYPE: DNA
<213> ORGANISM: Artificial Sequence
<220> FEATURE:
<223> OTHER INFORMATION: Nucleic acid sequence coding the light chain
      variable domain LA

<400> SEQUENCE: 54
gacgtggtca tgacacagag cccactgtct ctgcctgtga ccctgggaca gccagcctct       60
atctcctgca ggtccagcca gtccctggtg cacagctatg caacacata cctgtattgg      120 taccagcaga ggcccggaca gagcccaagg ctgctgatct acagggtgtc taatcggttc      180
tccggcgtgc ctgacaggtt tagcggctct ggctccggca ccgatttcac actgaagatc      240
tctagagtgg aggctgagga tgtgggcgtg tatttctgtt ttcagggcac ccatgtgcca      300
tacacatttg gcggcggcac caaggtggag atcaag                                336

<210> SEQ ID NO 55
<211> LENGTH: 336
<212> TYPE: DNA
<213> ORGANISM: Artificial Sequence
<220> FEATURE:
<223> OTHER INFORMATION: Nucleic acid sequence coding the light chain
      variable domain LB

<400> SEQUENCE: 55
gacgtggtca tgacacagag cccactgtct ctgcctgtga ccctgggaca gccagcctct       60
atctcctgca ggtccagcca gtccctggtg cacagctacg caacacata cctgtattgg      120 ttccagcaga ggcccggaca gagcccaagg ctgctgatct atagggtgtc taatcggttc      180
tccggcgtgc ctgacaggtt tagcggatct ggatccggaa ccgacttcac cctgaagatc      240
tctagagtgg aggctgagga tgtgggcgtg tactattgtt tccagggcac ccatgtgcca      300
tacacatttg gcggcggcac caaggtggag atcaag                                336
```

```
<210> SEQ ID NO 56
<211> LENGTH: 456
<212> TYPE: PRT
<213> ORGANISM: Mus musculus

<400> SEQUENCE: 56
```

| | | | | | | | | | | | | | | | |
|---|---|---|---|---|---|---|---|---|---|---|---|---|---|---|---|
| Gln | Val | Gln | Leu | Gln | Gln | Pro | Gly | Ala | Glu | Leu | Val | Arg | Pro | Gly | Ser |
| 1 | | | | 5 | | | | | 10 | | | | | 15 | |
| Ser | Val | Lys | Leu | Ser | Cys | Lys | Ala | Ser | Gly | Tyr | Thr | Phe | Thr | Ser | Tyr |
| | | | 20 | | | | | 25 | | | | | 30 | | |
| Trp | Val | His | Trp | Val | Lys | Gln | Arg | Pro | Ile | Gln | Gly | Leu | Glu | Trp | Ile |
| | | 35 | | | | | 40 | | | | | 45 | | | |
| Gly | Asn | Ile | Asp | Pro | Ser | Asp | Ser | Asp | Thr | His | Tyr | Asn | Gln | Lys | Phe |
| 50 | | | | | 55 | | | | | 60 | | | | | |
| Lys | Asp | Lys | Ala | Ser | Leu | Thr | Val | Asp | Lys | Ser | Ser | Thr | Ala | Tyr |
| 65 | | | | 70 | | | | | 75 | | | | | 80 |
| Met | Gln | Leu | Ser | Ser | Leu | Thr | Phe | Glu | Asp | Ser | Ala | Val | Tyr | Tyr | Cys |
| | | | | 85 | | | | | 90 | | | | | 95 | |
| Val | Arg | Gly | Gly | Thr | Gly | Thr | Met | Ala | Trp | Phe | Ala | Tyr | Trp | Gly | Gln |
| | | | 100 | | | | | 105 | | | | | 110 | | |
| Gly | Thr | Leu | Val | Thr | Val | Ser | Ala | Ala | Lys | Thr | Thr | Pro | Pro | Ser | Val |
| | | | 115 | | | | | 120 | | | | | 125 | | |
| Tyr | Pro | Leu | Ala | Pro | Gly | Cys | Gly | Asp | Thr | Thr | Gly | Ser | Ser | Val | Thr |
| | | 130 | | | | | 135 | | | | | 140 | | | |
| Leu | Gly | Cys | Leu | Val | Lys | Gly | Tyr | Phe | Pro | Glu | Ser | Val | Thr | Val | Thr |
| 145 | | | | | 150 | | | | | 155 | | | | | 160 |
| Trp | Asn | Ser | Gly | Ser | Leu | Ser | Ser | Val | His | Thr | Phe | Pro | Ala | Leu |
| | | | | 165 | | | | | 170 | | | | | 175 |
| Leu | Gln | Ser | Gly | Leu | Tyr | Thr | Met | Ser | Ser | Val | Thr | Val | Pro | Ser |
| | | | 180 | | | | | 185 | | | | | 190 | |
| Ser | Thr | Trp | Pro | Ser | Gln | Thr | Val | Thr | Cys | Ser | Val | Ala | His | Pro | Ala |
| | | | 195 | | | | | 200 | | | | | 205 | | |
| Ser | Ser | Thr | Thr | Val | Asp | Lys | Lys | Leu | Glu | Pro | Ser | Gly | Pro | Ile | Ser |
| | 210 | | | | | 215 | | | | | 220 | | | | |
| Thr | Ile | Asn | Pro | Cys | Pro | Pro | Cys | Lys | Glu | Cys | His | Lys | Cys | Pro | Ala |
| 225 | | | | | 230 | | | | | 235 | | | | | 240 |
| Pro | Asn | Leu | Glu | Gly | Gly | Pro | Ser | Val | Phe | Ile | Phe | Pro | Pro | Asn | Ile |
| | | | | 245 | | | | | 250 | | | | | 255 | |
| Lys | Asp | Val | Leu | Met | Ile | Ser | Leu | Thr | Pro | Lys | Val | Thr | Cys | Val | Val |
| | | | 260 | | | | | 265 | | | | | 270 | | |
| Val | Asp | Val | Ser | Glu | Asp | Asp | Pro | Asp | Val | Gln | Ile | Ser | Trp | Phe | Val |
| | | 275 | | | | | 280 | | | | | 285 | | | |
| Asn | Asn | Val | Glu | Val | His | Thr | Ala | Gln | Thr | Gln | Thr | His | Arg | Glu | Asp |
| 290 | | | | | 295 | | | | | 300 | | | | | |
| Tyr | Asn | Ser | Thr | Ile | Arg | Val | Val | Ser | Thr | Leu | Pro | Ile | Gln | His | Gln |
| 305 | | | | | 310 | | | | | 315 | | | | | 320 |
| Asp | Trp | Met | Ser | Gly | Lys | Glu | Phe | Lys | Cys | Lys | Val | Asn | Asn | Lys | Asp |
| | | | | 325 | | | | | 330 | | | | | 335 | |
| Leu | Pro | Ser | Pro | Ile | Glu | Arg | Thr | Ile | Ser | Lys | Ile | Lys | Gly | Leu | Val |
| | | | 340 | | | | | 345 | | | | | 350 | | |
| Arg | Ala | Pro | Gln | Val | Tyr | Ile | Leu | Pro | Pro | Ala | Glu | Gln | Leu | Ser |
| | | 355 | | | | | 360 | | | | | 365 | | |
| Arg | Lys | Asp | Val | Ser | Leu | Thr | Cys | Leu | Val | Val | Gly | Phe | Asn | Pro | Gly |
| | 370 | | | | | 375 | | | | | 380 | | | | |

```
Asp Ile Ser Val Glu Trp Thr Ser Asn Gly His Thr Glu Glu Asn Tyr
385                 390                 395                 400

Lys Asp Thr Ala Pro Val Leu Asp Ser Asp Gly Ser Tyr Phe Ile Tyr
                405                 410                 415

Ser Lys Leu Asn Met Lys Thr Ser Lys Trp Glu Lys Thr Asp Ser Phe
            420                 425                 430

Ser Cys Asn Val Arg His Glu Gly Leu Lys Asn Tyr Tyr Leu Lys Lys
                435                 440                 445

Thr Ile Ser Arg Ser Pro Gly Lys
            450                 455

<210> SEQ ID NO 57
<211> LENGTH: 219
<212> TYPE: PRT
<213> ORGANISM: Mus musculus

<400> SEQUENCE: 57

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Tyr Gly Asn Thr Tyr Leu Tyr Trp Tyr Leu Gln Lys Pro Gly Gln Ser
        35                  40                  45

Pro Lys Leu Leu Ile Tyr Arg Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
            100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
210                 215

<210> SEQ ID NO 58
<211> LENGTH: 15
<212> TYPE: DNA
<213> ORGANISM: Artificial Sequence
<220> FEATURE:
<223> OTHER INFORMATION: Sequence coding HCDR1

<400> SEQUENCE: 58
agctattggg tgcac                                                    15
```

```
<210> SEQ ID NO 59
<211> LENGTH: 15
<212> TYPE: DNA
<213> ORGANISM: Artificial Sequence
<220> FEATURE:
<223> OTHER INFORMATION: Sequence coding HCDR1

<400> SEQUENCE: 59
tcttattggg tgcac                                                           15

<210> SEQ ID NO 60
<211> LENGTH: 15
<212> TYPE: DNA
<213> ORGANISM: Artificial Sequence
<220> FEATURE:
<223> OTHER INFORMATION: Sequence coding HCDR1

<400> SEQUENCE: 60
tcctattggg tgcac                                                           15

<210> SEQ ID NO 61
<211> LENGTH: 51
<212> TYPE: DNA
<213> ORGANISM: Artificial Sequence
<220> FEATURE:
<223> OTHER INFORMATION: Sequence coding HCDR2

<400> SEQUENCE: 61
aacatcgacc ccagcgactc tgatacccat tacaatcaga agtttaagga c                   51

<210> SEQ ID NO 62
<211> LENGTH: 51
<212> TYPE: DNA
<213> ORGANISM: Artificial Sequence
<220> FEATURE:
<223> OTHER INFORMATION: Sequence coding HCDR2

<400> SEQUENCE: 62
aacatcgacc ccagcgactc tgatacacac tactccccta gctttcaggg c                   51

<210> SEQ ID NO 63
<211> LENGTH: 33
<212> TYPE: DNA
<213> ORGANISM: Artificial Sequence
<220> FEATURE:
<223> OTHER INFORMATION: Sequence coding HCDR3

<400> SEQUENCE: 63
ggaggaaccg gaacaatggc ttggtttgct tac                                       33

<210> SEQ ID NO 64
<211> LENGTH: 33
<212> TYPE: DNA
<213> ORGANISM: Artificial Sequence
<220> FEATURE:
<223> OTHER INFORMATION: Sequence coding HCDR3

<400> SEQUENCE: 64
ggaggaaccg gcacactggc ttggttcgct tac                                       33

<210> SEQ ID NO 65
<211> LENGTH: 33
<212> TYPE: DNA
<213> ORGANISM: Artificial Sequence
<220> FEATURE:
<223> OTHER INFORMATION: Sequence coding HCDR3
```

```
<400> SEQUENCE: 65
ggaggaaccg gaacaatggc ttacttcgct tat                           33

<210> SEQ ID NO 66
<211> LENGTH: 33
<212> TYPE: DNA
<213> ORGANISM: Artificial Sequence
<220> FEATURE:
<223> OTHER INFORMATION: Sequence coding HCDR3

<400> SEQUENCE: 66
ggaggaaccg gcacactggc ttacttcgct tat                           33

<210> SEQ ID NO 67
<211> LENGTH: 48
<212> TYPE: DNA
<213> ORGANISM: Artificial Sequence
<220> FEATURE:
<223> OTHER INFORMATION: Sequence coding LCDR1

<400> SEQUENCE: 67
aggtccagcc agtccctggt gcacagctat ggcaacacat acctgtat           48

<210> SEQ ID NO 68
<211> LENGTH: 21
<212> TYPE: DNA
<213> ORGANISM: Artificial Sequence
<220> FEATURE:
<223> OTHER INFORMATION: Sequence coding LCDR2

<400> SEQUENCE: 68
agggtgtcta atcggttctc c                                       21

<210> SEQ ID NO 69
<211> LENGTH: 27
<212> TYPE: DNA
<213> ORGANISM: Artificial Sequence
<220> FEATURE:
<223> OTHER INFORMATION: Sequence coding LCDR3

<400> SEQUENCE: 69
tttcagggca cccatgtgcc atacaca                                 27

<210> SEQ ID NO 70
<211> LENGTH: 13
<212> TYPE: PRT
<213> ORGANISM: Homo sapiens

<400> SEQUENCE: 70

Glu Leu Ile Tyr Asn Gln Lys Glu Gly His Phe Pro Arg
1               5                   10

<210> SEQ ID NO 71
<211> LENGTH: 12
<212> TYPE: PRT
<213> ORGANISM: Homo sapiens

<400> SEQUENCE: 71

Arg Asn Asn Met Asp Phe Ser Ile Arg Ile Gly Asn
1               5                   10

<210> SEQ ID NO 72
<211> LENGTH: 9
<212> TYPE: PRT
<213> ORGANISM: Homo sapiens
```

```
<400> SEQUENCE: 72

Ser Pro Arg Asp Ile Thr Leu Lys Trp
1               5

<210> SEQ ID NO 73
<211> LENGTH: 4
<212> TYPE: PRT
<213> ORGANISM: Homo sapiens

<400> SEQUENCE: 73

Tyr Asn Gln Lys
1
```